US007268096B2

(12) United States Patent
Small et al.

(10) Patent No.: US 7,268,096 B2
(45) Date of Patent: Sep. 11, 2007

(54) DIIMINE METAL COMPLEXES, METHODS OF SYNTHESIS, AND METHODS OF USING IN OLIGOMERIZATION AND POLYMERIZATION

(75) Inventors: Brooke L. Small, Kingwood, TX (US); Michael Carney, Eau Claire, WI (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 11/186,306

(22) Filed: Jul. 21, 2005

(65) Prior Publication Data

US 2007/0027334 A1 Feb. 1, 2007

(51) Int. Cl.
*B01J 31/18* (2006.01)
*C08F 4/80* (2006.01)
*C07F 15/02* (2006.01)

(52) U.S. Cl. ......................... 502/167; 526/161; 556/23

(58) Field of Classification Search ................ 526/161; 502/167; 556/23
See application file for complete search history.

(56) References Cited

U.S. PATENT DOCUMENTS

| | | | |
|---|---|---|---|
| 4,971,986 | A | 11/1990 | Stanek et al. |
| 5,811,618 | A | 9/1998 | Wu |
| 5,880,241 | A | 3/1999 | Brookhart et al. |
| 5,955,555 | A | 9/1999 | Bennett |
| 6,103,946 | A | 8/2000 | Brookhart, III et al. |
| 6,184,428 | B1 | 2/2001 | Zahoor et al. |
| 6,214,761 | B1 | 4/2001 | Bennett |
| 6,281,303 | B1 | 8/2001 | Lavoie et al. |
| 6,489,497 | B1 | 12/2002 | Brookhart, III et al. |
| 6,545,108 | B1 * | 4/2003 | Moody et al. .............. 526/161 |
| 6,683,141 | B1 | 1/2004 | Gibson et al. |
| 6,720,468 | B2 | 4/2004 | Elomari et al. |
| 6,818,715 | B1 | 11/2004 | Kristen et al. |
| 6,825,297 | B1 | 11/2004 | Devore et al. |
| 6,894,134 | B2 | 5/2005 | Brookhart et al. |
| 2002/0016425 | A1 | 2/2002 | De Boer et al. |
| 2002/0028941 | A1 | 3/2002 | De Boer et al. |
| 2002/0061987 | A1 | 5/2002 | Lenges |
| 2003/0036615 | A1 | 2/2003 | Brookhart, III et al. |
| 2003/0050494 | A1 | 3/2003 | Brookhart, III et al. |
| 2003/0119921 | A1 | 6/2003 | De Boer et al. |
| 2004/0068154 | A1 | 4/2004 | Small |
| 2004/0180778 | A1 | 9/2004 | Small |

FOREIGN PATENT DOCUMENTS

| | | |
|---|---|---|
| CN | 1306014 | 8/2001 |
| CN | 1374281 | 10/2002 |
| DE | 198 12 066 A1 | 1/1999 |
| EP | 1 325 924 A1 | 7/2003 |
| JP | 2002371062 | 12/2002 |
| JP | 2003147009 | 5/2003 |
| WO | WO96/11193 | 4/1996 |
| WO | WO 00/58320 | 10/2000 |
| WO | WO 00/66638 | 11/2000 |
| WO | WO 00/68280 | 11/2000 |
| WO | WO 01/10875 A1 | 2/2001 |
| WO | WO 01/58874 A1 | 8/2001 |
| WO | WO 01/74830 A1 | 10/2001 |
| WO | WO 02/00339 A2 | 1/2002 |
| WO | WO 02/28805 A2 | 4/2002 |
| WO | WO 02/34701 A1 | 5/2002 |
| WO | WO 02/34746 A2 | 5/2002 |
| WO | WO 02/090365 A1 | 11/2002 |
| WO | WO 02/096919 A1 | 12/2002 |
| WO | WO 03/010207 A1 | 2/2003 |
| WO | WO 03/011876 A1 | 2/2003 |
| WO | WO 03/022889 A1 | 3/2003 |
| WO | WO 03/053890 A1 | 7/2003 |
| WO | WO 03/053891 A1 | 7/2003 |
| WO | WO 2004/026795 A2 | 4/2004 |
| WO | WO 2004/029012 A1 | 4/2004 |
| WO | WO 2004/033398 A1 | 4/2004 |
| WO | WO 2004/056477 A1 | 7/2004 |
| WO | WO 2004/056478 A1 | 7/2004 |
| WO | WO 2004/056479 A1 | 7/2004 |
| WO | WO 2004/056480 A1 | 7/2004 |

OTHER PUBLICATIONS

Wang et al. "Catalytic Sulfoxidation and Epoxidation with a Mn(III) Triazacorrole: Evidence for A "Third Oxidant" in High-Valent Porphyrinoid Oxidations" Journal of the American Chemical Society 2004, vol. 126, pp. 18-19.*

Small et al. "Highly Active Iron and Cobalt Catalysts for the Polymerization of Ethylene" Journal of the American Chemical Society 1998, vol. 120, pp. 4049-4050.*

DuBois, Thomas D. "Four- and Five-Coordinate Nickel(II) Complexes of 2,3-Butanedionebis)2-diphenylphosphinoethylamine)" Inorganic Chemistry 1972, vol. 11, pp. 718-722.*

Chang et al., "Model Complexes of the Active Site in Peptide Deformylase: A New Family of Mononuclear N2S-M(II) Complexes" Inorganic Chemistry 2001, vol. 40, pp. 194-195.*

Nelson, S. Martin, "Metal-ion Controlled Reactions of 2,6-Diacetylpyridine with 1,2-Di-aminoethane and 2,6-Diformylpyridine wit o-Phenylenediamine and the Crystal and Molecular Structure of a Pentagonal Pyramidal Cadmium (II) Complex containing Unidentate o-Phenylenediamine," 1982, pp. 407-415.

(Continued)

*Primary Examiner*—Kamal A. Saeed
*Assistant Examiner*—Joseph R. Kosack
(74) *Attorney, Agent, or Firm*—Conley Rose, P.C.; Rodney B. Carroll; K. KaRan Reed

(57) ABSTRACT

Novel α-diimine metal complexes, particularly iron complexes are disclosed. The α-diimine metal complexes are produced by forming one of the α-diimine metal complex imine bonds in the presence of a metal salt or an α-acylimine metal complex. α-diimine metal complexes having two different α-diimine nitrogen groups may be produced. The α-diimine metal complexes are useful for polymerizing or oligomerizing olefins.

15 Claims, 2 Drawing Sheets

OTHER PUBLICATIONS

Britovsek, George J. P., et al., "Novel olefin polymerization catalysts based on iron and cobalt," Chem Comm, 1998, pp. 849-850.
Small, Brooke L., et al., "New Iron and Cobalt Catalysts for the Polymerization of Olefins," Dallas ACS, Mar. 1998, p. 213, vol. 39.
Small, Brooke L., et al., "Highly Active Iron and Cobalt Catalysts for the Polymerization of Ethylene," American Chemical Society, Apr. 14, 1998, pp. 4049-4050, vol. 120.
Small, Brooke L., et al., "Iron-Based Catalysts with Exceptionally High Activities and Selectivities for Oligomerization of Ethylene to Linear a-Olefins," American Chemical Society, Jul. 7, 1998, pp. 7143-7144, vol. 120.
Kumar, R.N., et al., "Mononuclear and Binuclear Complexes of Fe(II) and Cu(II) with 2,6-Diacetyl Pyridine Monoxime and Phenylene Diamine," Asian Journal of Chemistry, Jul.-Sep. 1999, pp. 964-969, vol. 11, No. 3.
Bennett, Alison M. A., "Novel, highly active iron and cobalt catalysts for olefin polymerization," Enabling Science-American Chemical Society, Chemtech, Jul. 1999, pp. 24-28, vol. 29, No. 7.
Britovsek, George J.P., et al., "Iron and Cobalt Ethylene Polymerization Catalysts Bearing 2,6-Bis(lmino) Pyridyl Ligands: Synthesis, Structures, and Polymerization Studies," American Chemical Society, Sep. 11, 1999, pp. 8728-8740, vol. 121.
Britovsek, George J.P., et al., "Oligomerisation of Ethylene by Bis(imino)pyridyliron and—cobalt Complexes," Full Paper—Chem. Eur. J., 2000, pp. 2221-2231, vol. 6, No. 12.
Katritzky, Alan R., et al., "Syntheses of 1,4-Benzothiazepines and 1,4-Benzoxazepines via Cyclizations of 1-[2-Arylthio(oxy)ethyl]-5-benzotriazolyl-2-pyrrolidinones and 3-Benzotriazolyl-2-[2-arylthio(oxy)ethyl]-1-isoindolinones," J.Org.Chem.—American Chemical Society, Jul. 18, 2001, pp. 5590-5594, vol. 66.
Small, Brooke L., et al., "Iron Catalysts for the Head-to-Head Dimerization of a-Olefins and Mechanistic Implications for the Production of Linear a-Olefins," Organometallics—American Chemical Society, Nov. 22, 2001, pp. 5738-5744, vol. 20.
Carter, Anthea, et al., "High activity ethylene trimerisation catalysts based on diphosphine ligands," Chem.Commun.-The Royal Society of Chemistry, Mar. 20, 2002, pp. 858-859 & Supplementary Information (2 pgs.).
Esteruelas, Miguel A., et al., "Preparation, Structure, and Ethylene Polymerization Behavior of Bis (imino) pyridyl Chromium(III) Complexes," Organometallics—American Chemical Society, Jan. 1, 2003, pp. 395-406, vol. 22.
McGuinness, David S., et al., "Novel Cr-PNP complexes as catalysts for the trimerisation of ethylene," ChemComm, Jan. 2, 2003, pp. 334-335.
Chen, Yaofeng, et al., "Fluoro-Substituted 2,6-Bis(imino)pyridyl Iron and Cobalt Complexes: High-Activity Ethylene Oligomerization Catalysts," Organometallics—American Chemical Society, Feb. 15, 2003, pp. 1231-1236, vol. 22.
McGuinness, David S., et al., "First Cr(III)-SNS Complexes and Their Use as Highly Efficient Catalysts for the Trimerization of Ethylene to 1-Hexene," JACS Communications—American Chemical Society, Apr. 15, 2003, pp. 5272-5273.
Small, Brooke L., et al., "Comparative Dimerization of 1-Butene with a Variety of Metal Catalysts, and the Investigation of a New Catalyst for C-H Bond Activation," Full Paper—Chem. Eur. J., 2004, pp. 1014-1020, vol. 10 & Supporting Information (2 pgs.).
Small, Brooke L., et al., "New Chromium Complexes for Ethylene Oligomerization: Extended Use of Tridentate Ligands in Metal-Catalyzed Olefin Polymerization," Macromolecules—American Chemical Society, May 18, 2004, pp. 4375-4386, vol. 37.
Rosenberger, Volker, et al.; "Diazadien-Komplexe des Rutheniums, XIII. Bis(diazadien) ruthenium: Isomerisierung, Hydrierung, Metaillierung; Struktur eines Kalium(tmeda)2-ruthenats(0)," Journal of Organometallic Chemistry, vol. 411, Elsevier Sequoia, 1991, pp. 445-456.
Tempel, Daniel J., et al.; "Mechanistic Studies of Pd(II)-a-Diimine-Catalyzed Olefin Polymerizations," J. Am. Chem. Soc., vol. 122, American Chemical Society, 2000, pp. 6686-6700.
Stojcevic, Goran, et al.; "Coordination insertion reactions of acrylonitrile into Pd-H and Pd-methyl bonds in a diimine-palladium(II) system," Journal of Organometallic Chemistry, vol. 690, Elsevier, 2005, pp. 4349-4355.
Invitation to Pay Additional Fees and Partial Search Report of PCT/US2006/028068, Jan. 5, 2007, 6 pgs.

* cited by examiner

Figure 1 – ORTEP Diagram of the X-Ray Crystal Structure for the α-Diimine Metal Complex Produced in Example 5
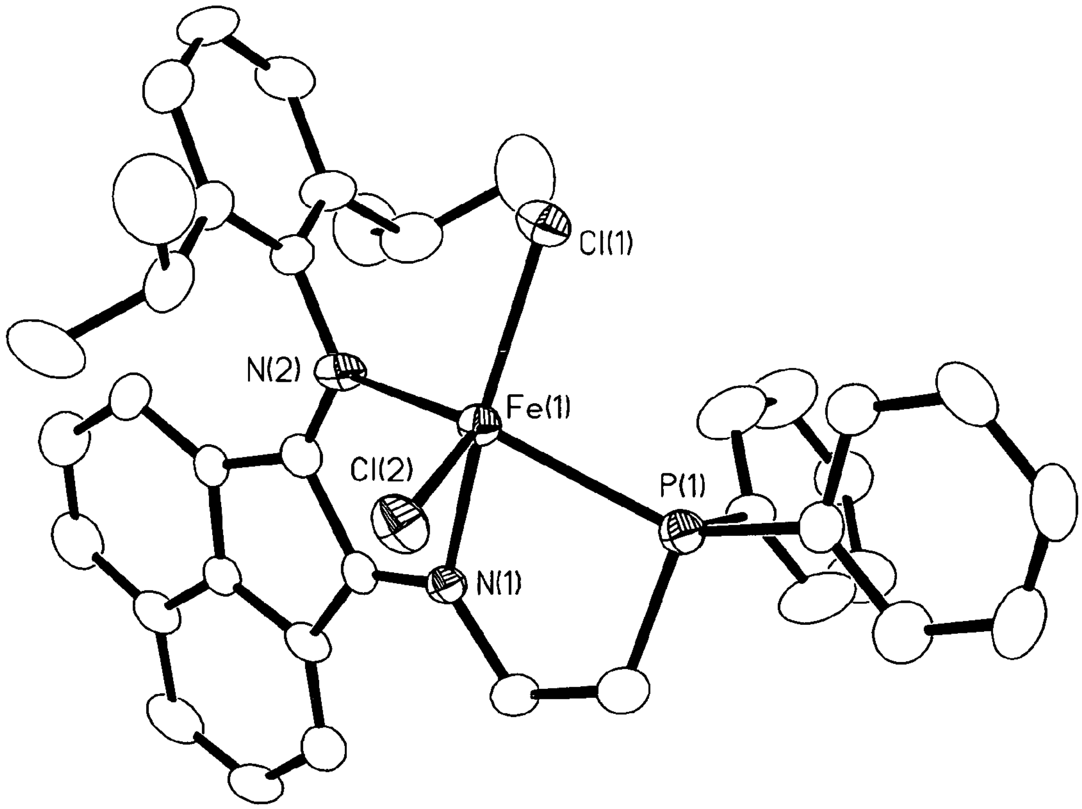

Figure 2 – ORTEP Diagram of the X-Ray Crystal Structure for the α-Diimine Metal Complex Produced in Example 7
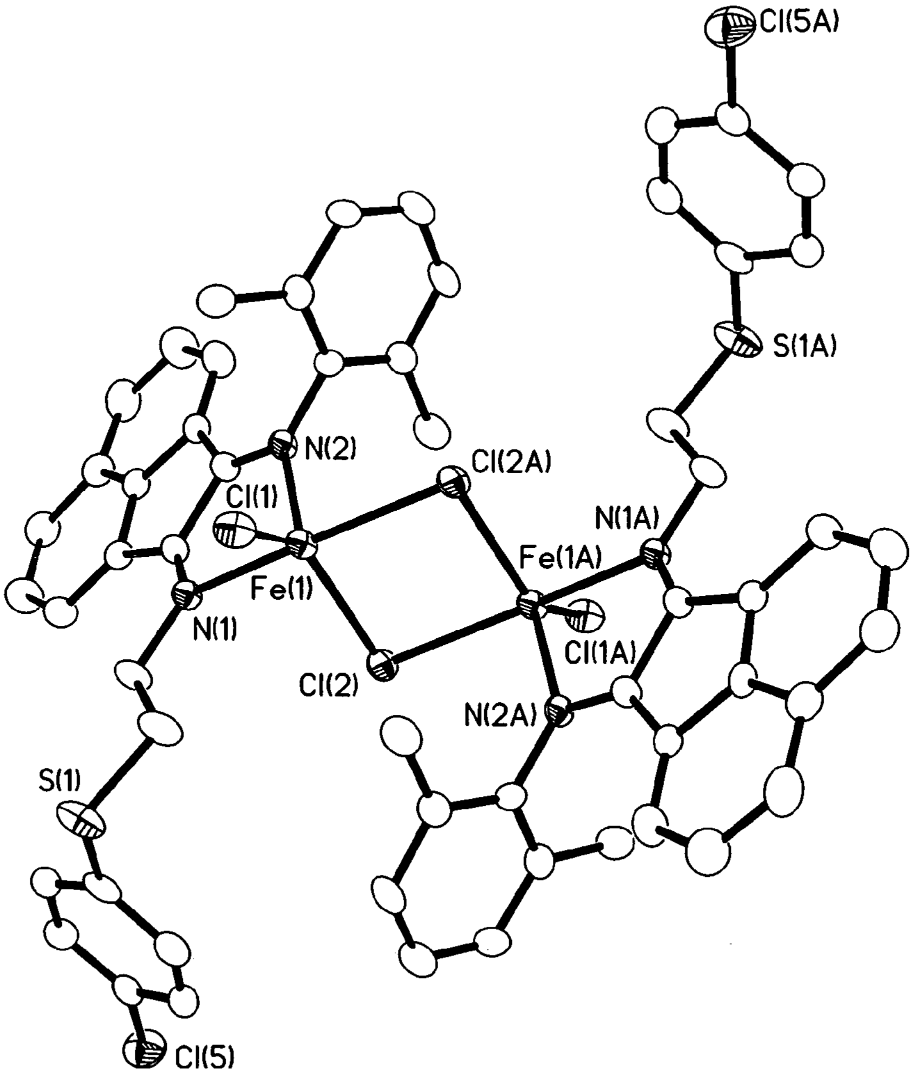

DIIMINE METAL COMPLEXES, METHODS OF SYNTHESIS, AND METHODS OF USING IN OLIGOMERIZATION AND POLYMERIZATION

CROSS-REFERENCE TO RELATED APPLICATIONS

The present application is related to U.S. patent application Ser. No. 11/186,039 and U.S. patent application Ser. No. 11/186,038 (now U.S. Pat. No. 7,129,304 issued Oct. 31, 2006), each having like title and filed on Jul. 21, 2005.

FIELD OF THE INVENTION

The present application relates generally to olefin oligomerization. More particularly, the present application relates to α-diimine metal complexes, methods of producing α-diimine metal complexes, and the use of α-diimine metal complexes in the oligomerization and/or polymerization of olefins.

BACKGROUND OF THE INVENTION

Olefins, also commonly known as alkenes, are important items of commerce. Their many applications include employment as intermediates in the manufacture of detergents, as more environmentally friendly replacements where refined oils might otherwise be used, as monomers, and as intermediates for many other types of products. An important subset of olefins are olefin oligomers, and one method of making olefin oligomers is via oligomerization of ethylene, which is a catalytic reaction involving various types of catalysts. Examples of catalysts used commercially in polymerization and oligomerization of olefins include alkylaluminum compounds, certain nickel-phosphine complexes, and a titanium halide with a Lewis acid, such as diethyl aluminum chloride.

Another group of olefin polymerization catalysts is derived from pyridine bis-imines. With catalysts of this type, a nitrogen-based ligand engages in a coordination reaction with a transition metal salt. The coordination reaction forms a metal complex, which is a catalyst precursor. The metal complex further reacts with another precursor or activator to generate a metal alkyl or metal hydride species. The catalyst resulting from the generation of the metal alkyl or metal hydride species polymerizes olefins.

Applications and demand for olefin polymers and oligomers continue to multiply, and competition to supply them correspondingly intensifies. Thus, additional novel and improved catalysts and methods for olefin polymerization and oligomerization are desirable.

SUMMARY OF THE INVENTION

In an aspect the present invention provides a method for producing an α-diimine metal complex comprising forming at least one imine bond in the presence of a metal salt, metal complex, or combinations thereof. In embodiments, the method for producing an α-diimine metal complex comprises: a) contacting an α-acylimine compound, a metal salt, and a primary amine; and b) recovering the α-diimine metal complex. In some embodiments, the α-acylimine compound comprises an α-acylimine group and an α-acylimine nitrogen group consisting of an organyl group consisting of inert functional groups or a hydrocarbyl group and the primary amine comprises an —$NH_2$ group, a metal salt complexing group and a linking group linking the metal salt complexing group to the —$NH_2$ group. In another embodiment, the α-acylimine compound comprises an α-acylimine group and an α-acylimine nitrogen group comprising a metal salt complexing group and a linking group linking the metal salt complexing group to the α-acylimine nitrogen atom, and the primary amine consists of an —$NH_2$ group and an organyl group consisting of an inert functional group or a hydrocarbyl group. In yet another embodiment, the method for producing an α-diimine metal complex comprises: a) contacting an α-acylimine metal complex and a primary amine; and b) recovering the α-diimine metal complex.

In another aspect, the present invention provides for an α-diimine metal complex composition comprising a metal salt complexed to a bidentate or tridentate α-diimine compound wherein the α-diimine compound comprises an α-diimine group, a first imine nitrogen group, and a second imine nitrogen group which is different from the first imine nitrogen group. In embodiments, the α-diimine compound is tridentate, the α-diimine group is derived from an α-diacyl compound, the first imine nitrogen group consists of a $C_1$ to $C_{30}$ organyl group consisting of inert functional groups or a $C_1$ to $C_{30}$ hydrocarbyl group, and the second imine nitrogen group comprises a metal salt complexing group and a linking group linking the metal salt complexing group to the imine nitrogen group. In another embodiment, the α-diimine compound is bidentate, the α-diimine group is derived from an α-diacyl compound, the first imine nitrogen group consists of a $C_1$ to $C_{30}$ organyl group consisting of inert functional groups or a $C_1$ to $C_{30}$ hydrocarbyl group, and the second imine nitrogen group consists of a $C_1$ to $C_{30}$ organyl group consisting of inert functional groups or a $C_1$ to $C_{30}$ hydrocarbyl group. In further embodiments, the α-diimine metal complex comprises a metal salt comprising iron complexed to a tridentate α-diimine compound comprising: 1) an α-diimine group derived from acenaphthenequinone, phenanthrenequinone, or pyrenequinone; 2) a first imine nitrogen group consisting of a 2,6-dimethylphenyl group, a 2,6-diethylphenyl group, a 2,6-diisopropylphenyl group, or a 2,6-di-tert-butylphenyl group; and 3) a second imine nitrogen group comprising a metal salt complexing group and a linking group linking the metal salt complexing group to the second imine nitrogen atom.

In yet another aspect, the present invention provides a process for producing alpha olefins comprising: a) contacting ethylene, an α-diimine metal complex, and a cocatalyst; and forming an oligomerized ethylene product comprising alpha olefins. In embodiments, the α-diimine metal complex comprises a metal salt complexed to an α-diimine compound, wherein the α-diimine compound comprises: 1) an α-diimine group derived from an α-diacyl compound; 2) a first imine nitrogen group consisting of a $C_1$ to $C_{30}$ organyl group consisting of inert functional groups or a $C_1$ to $C_{30}$ hydrocarbyl group; and 3) a second imine nitrogen group comprising a metal salt complexing group and a linking group linking the metal salt complexing group to the imine nitrogen group. In other embodiments, the α-diimine metal complex comprises a metal salt comprising iron complexed to an α-diimine compound comprising; 1) an α-diimine group derived from acenaphthenequinone, phenanthrenequinone, or pyrenequinone; 2) a first imine nitrogen group consisting of a 2,6-dimethylphenyl group, a 2,6-diethylphenyl group, or a 2,6-diisopropylphenyl group; and 3) a second imine nitrogen group comprising a metal salt complexing group and a linking group linking the metal salt complexing group to the second imine nitrogen atom.

DESCRIPTION OF THE DRAWINGS

FIG. 1 represents the ORTEP diagram of the X-ray crystal structure for the α-diimine metal complex produced in Example 5.

FIG. 2 represents the ORTEP diagram of the X-ray crystal structure for the α-diimine metal complex produced in Example 7.

DETAILED DESCRIPTION OF EMBODIMENTS

The present application discloses α-diimine metal complexes, methods for producing α-diimine metal complexes, and the use of α-diimine metal complexes in the oligomerization and/or polymerization of olefins.

Definitions

For the purpose of this application the designation "α-" represents a relational designation that when preceding a chemical name, either general or specific, indicates that the two functional groups are on adjacent carbon atoms. Non-limiting examples using the relational α-designation include, α-dione where the two ketone oxygen atoms are bonded to adjacent carbon atoms, α-diimine where the two imine nitrogen atoms are bonded to adjacent carbon atoms, and α-acylimine where the acyl group oxygen atom and the imine nitrogen atom are bonded to adjacent carbon atoms. The α-relational designation may also be used to describe other compounds described herein.

For purposes of this application, an "acyl group" is represented by the structure

wherein the undesignated valences may be hydrogen, an organyl group, a hydrocarbyl group, and/or any other group as indicated herein. Thus, the term acyl group may include ketones and/or aldehydes. The present application may also refer to substituent(s)/group(s)/atom(s) attached to the acyl group carbon atom (an acyl carbon group).

For the purpose of this application, the term "imine group" is represented by the structure

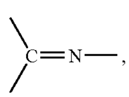

wherein the undesignated valences can be hydrogen, an organyl group, a hydrocarbyl group, and/or any other group as indicated herein. The term imine group comprises both aldimines and ketimines. The present application may also refer to substituent(s)/group(s)/atom(s) attached to the imine carbon atom (an imine carbon group) and/or substituent(s)/group(s)/atom(s) attached to the imine nitrogen atom (an imine nitrogen group). Additionally, the present application may refer to substituents/groups/atoms attached to the acyl carbon atom of the α-acylimine group (an α-acylimine acyl carbon group), substituents/groups/atoms attached to the imine carbon atom of the α-acylimine group (an α-acylimine imine carbon group), and/or substituent(s)/group(s)/atom(s) attached to the imine nitrogen atom of the α-acylimine group (an α-acylimine nitrogen group). For the purpose of this application the —C═N— portion of a pyridine ring, or pyridine containing ring system (shown in its localized or delocalized form) does not constitute an imine group.

For purposes of this application, a "hydrocarbyl group" has the definition specified by IUPAC: a univalent group formed by removing a hydrogen atom from a hydrocarbon (i.e. a group containing only carbon and hydrogen). A hydrocarbyl group can include the term "alkyl" or "alkyl group." A hydrocarbyl group can include rings, ring systems, aromatic rings, and aromatic ring systems which contain only carbon and hydrogen.

For purposes of this application, an "organyl group" has the definition specified by IUPAC: an organic substituent group, regardless of functional type, having one free valence at a carbon atom. Thus, an organyl group can contain organic functional groups and/or atoms other than carbon and hydrogen (i.e. an organic group that can comprise functional groups and/or atoms in addition to carbon and hydrogen). For example, non-limiting examples of atoms other than carbon and hydrogen include halogens, oxygen, nitrogen, and phosphorus, among others. Non-limiting examples of functional groups include ethers, aldehydes, ketones, aldehydes, esters, sulfides, amines, and phosphines, among others. Included in the organyl group definition are heteroatom containing rings, heteroatom containing ring systems, heteroaromatic rings, and heteroaromatic ring systems. Finally, it should be noted that the organyl group definition includes the organyl group consisting of inert functional groups, and the hydrocarbyl group as a members.

For the purposes of this application, the term or variations of the term "organyl group consisting of inert functional groups" refers to an organyl group wherein the organic functional groups and/or atoms other than carbon and hydrogen present in the functional group are restricted to those functional group and/or atoms other than carbon and hydrogen which do not complex with a metal salt and/or are inert under the process conditions defined herein. Thus, the term or variation of the term "organyl groups consisting of inert functional groups" further defines the particular organyl groups that can be present within the organyl group consisting of inert functional groups. Additionally, the term "organyl group consisting of inert functional groups" can refer to the presence of one or more inert functional groups within the organyl group. The term or variation of the "organyl group consisting of inert functional group" definition includes the hydrocarbyl group as a member.

For purposes of this application, an "inert functional group" is a group which does not substantially interfere with any process described herein in which it takes part and/or does not complex with the metal salt of an α-diimine metal complex. The term "does not complex with the metal salt" can include groups that could complex with a metal salt but in particular molecules described herein can not complex with a metal salt due to its positional relationship within a complexing α-diimine group. For example, while an ether group can complex with a metal salt, an ether group located at a para position of a substituted phenyl imine nitrogen group is an inert functional group because a single metal salt molecule can not complex with both the ether group and the imine group of the α-diimine compound within the same molecule. Thus, the inertness of a particular functional group is not only related to its functional group's inherent inability to complex the metal salt but can also be related to the functional group's position within the metal complex. Non-limiting examples of inert functional groups which due not substantially interfere with any process described herein can include halo (fluoro, chloro, bromo and iodo), ethers (alkoxy group or etheryl group), sulfides (sulfidyl group), and/or hydrocarbyl groups.

The terms "polymerized product having X carbon atoms" and "oligomerized product having X carbon atoms," wherein X can be any integer, refers to materials produced in a reactor by monomer polymerization or monomer oligomerization that has X carbon atoms. Thus, the term polymerized product having X carbon atoms and oligomerized product having X carbon atoms excludes materials in the reactor effluent having X carbon atoms which were not polymerized or oligomerized (e.g. solvent).

For purposes of this application, a primary carbon group is —$CH_3$.

For purposes of this application, a secondary carbon group includes a group of the formula —$CH_2$—, wherein the one free valence (-) is to an atom other than a hydrogen atom (the bond represented by the dash, —, is to atom and/or group to which the secondary carbon group is attached). Thus, the free valence can be bonded to a halogen atom, carbon atom, oxygen atom, sulfur atom, etc. In other words, the free valence can be to an organyl group, an organyl group consisting of inert functional groups, a hydrocarbyl group, a functional group, or an inert functional group. Non-limiting examples of secondary carbon groups include —$CH_2CH(CH_3)_2$, —$CH_2Cl$, —$CH_2C_6H_5$, and —$CH_2OCH_3$.

For purposes of this application, a tertiary carbon group includes a group of the formula —CH═, wherein the two free valences (═) are to atoms other than a hydrogen atom (the bond represented by the dash, —, is to atom and/or group to which the tertiary carbon group is attached). Thus, the two free valences can be independently bonded to a halogen atom, carbon atom, oxygen atom, sulfur atom, etc. In other words, each of the two free valences can be to an organyl group, an organyl group consisting of inert functional groups, a hydrocarbyl group, a functional group, or an inert functional group. Non-limiting examples of secondary carbon groups include —$CH(CH_3)_2$, —$CHCl_2$, —$CH(C_6H_5)_2$, -cyclohexyl, —$CH(CH_3)OCH_3$, and —CH═$CHCH_3$.

For purposes of this application, a quaternary carbon group includes a group of the formula —C≡, wherein the three free valences, ≡, are to atoms other than a hydrogen atom (the bond represented by the dash, —, is to atom and/or group to which the quaternary carbon group is attached). Thus, each of the three free valences can be independently bonded to a halogen atom, carbon atom, oxygen atom, sulfur atom, etc. In other words, each of the three free valences can be to an organyl group, an organyl group consisting of inert functional groups, a hydrocarbyl group, a functional group, or an inert functional group. Non-limiting examples of tertiary carbon groups include: —$C(CH_3)_3$, —$C(C_6H_5)_3$, —$CCl_3$, —$C(CH_3)_2OCH_3$, —C≡CH, —$C(CH_3)CH$═$CH_2$, —$C_6H_5$, —$CF_3$, and -1-adamantyl.

α-Diimine Metal Complex, Starting Materials, and Intermediates

Generally, the α-diimine metal complexes can be prepared from α-diacyl compounds, two primary amines, and a metal salt. Within the methods to prepare the α-diimine metal complexes, additional compounds including α-acylimine compounds and α-acylimine metal complexes can be intermediates and/or starting materials in the synthesis of the α-diimine metal complexes. The α-diacyl compounds, primary amines, α-acylimine compounds, α-acylimine metal complexes, and metal salts are independent elements within the α-diimine metal complex synthesis and further described herein.

α-Diacyl Compounds

Generally, α-diacyl compounds utilized in the production of the α-diimine metal complexes comprise two acyl groups capable of forming an imine group when contacted with a primary amine. Appropriate α-diacyl compounds can be those capable of reacting with two primary amines to form an α-diimine compound. Within in this specification, the term "capable of reacting with two primary amines to form an α-diimine compound" should not be construed to mean that two primary amines are necessarily added in the same step. Nor should the term be construed to mean that an α-diimine compound is necessarily formed as an intermediate to an α-diimine metal complex. Further, defining an α-diacyl compound as one capable of forming an imine group when contacted with a primary amine is not necessarily indicative of methods of forming an imine group. The term "capable of reacting with two primary amines to form an α-diimine compound" is intended to describe to one skilled in the art the particular α-diacyl compounds which can be utilized in the synthesis of the α-diimine metal complexes described herein. The α-diimine metal complexes can be produced utilizing any method as described herein.

One class of α-diacyl compounds that can be used in preparing α-diimine metal complexes is an α-ketoaldehyde, which is a compound wherein a ketone oxygen atom and an aldehyde oxygen atom are bonded to adjacent carbon atoms. The α-ketoaldehydes utilized in the production of the α-diimine metal complexes can be any α-ketoaldehyde capable of reacting with two primary amines to form an α-diimine compound. The α-ketoaldehyde can be saturated, unsaturated, linear, branched, acyclic, cyclic, aromatic, and/or heteroaromatic.

Generally, the α-ketoaldehyde will have the structure $R^{ka}$—C(═O)C(═O)H wherein $R^{ka}$ can be an organyl group, an organyl group consisting of inert functional groups, or a hydrocarbyl group. In some embodiments, $R^{ka}$ is an organyl group; alternatively, an organyl group consisting of inert functional groups; or alternatively, a hydrocarbyl group. Generally, $R^{ka}$ can be a $C_1$ to $C_{30}$ organyl group; alternatively, a $C_1$ to $C_{30}$ organyl group consisting of inert functional groups; alternatively, a $C_1$ to $C_{30}$ hydrocarbyl group; alternatively, a $C_1$ to $C_{20}$ organyl group; alternatively, a $C_1$ to $C_{20}$ organyl group consisting of inert functional groups; alternatively, a $C_1$ to $C_{20}$ hydrocarbyl group; alternatively, a $C_1$ to $C_{10}$ organyl group; alternatively, a $C_1$ to $C_{10}$ organyl group consisting of inert functional groups; alternatively, a $C_1$ to $C_{10}$ hydrocarbyl group; alternatively, a $C_1$ to $C_5$ organyl group; alternatively, a $C_1$ to $C_5$ organyl group consisting of inert functional groups; or alternatively, a $C_1$ to $C_5$ hydrocarbyl group. Generally the organyl group, organyl group consisting of inert functional groups, or hydrocarbyl group of the α-ketoaldehyde can be saturated, unsaturated, acyclic, cyclic, linear, branched, and/or aromatic.

In some embodiments, $R^{ka}$ represents an acyclic organyl group, an acyclic organyl group consisting of inert functional groups, or an acyclic hydrocarbyl group. In other embodiments, $R^{ka}$ represents a cyclic organyl group, a cyclic organyl group consisting of inert functional groups, or cyclic hydrocarbyl group. Regardless of the structure of the organyl group, organyl group consisting of inert functional groups, or hydrocarbyl group, $R^{ka}$ can have any number of carbon atoms as indicated herein. In some embodiments, the α-ketoaldehyde is a $C_3$ to $C_{20}$ glyoxal; alternatively, a $C_3$ to $C_{10}$ glyoxal; or alternatively, a $C_3$ to $C_6$ glyoxal. In some embodiments, the α-ketoaldehyde is phenylglyoxal or a substituted phenylglyoxal. In other embodiments, the α-ketoaldehyde is phenylglyoxal. Within substituted phenylglyoxal, each substituent can be a $C_1$ to $C_5$ organyl groups, a $C_1$ to $C_5$ organyl groups consisting of inert functional groups, and/or a $C_1$ to $C_5$ hydrocarbyl groups. In other embodiments, each phenyl substituents can be a $C_1$ to $C_5$ organyl groups consisting of inert functional groups; or alternatively, a $C_1$ to $C_5$ hydrocarbyl groups.

A second class of α-diacyl compounds which can be used in preparing α-diimine metal complexes is an α-dione (a compound wherein two ketone oxygen atoms are bonded to adjacent carbon atoms). The α-diones utilized in the production of the α-diimine metal complexes can be any α-dione compound capable of reacting with two primary amines to form an α-diimine compound. The α-dione can be saturated, unsaturated, acyclic, cyclic, linear, branched, aromatic, and/or heteroaromatic.

Generally, the α-dione will have the structure $R^{k1}$—C(═O)—C(═O)—$R^{k2}$ wherein the structures of $R^{k1}$ and $R^{k2}$ are independent of each other and can be an organyl group, an organyl group consisting of inert functional groups, or a hydrocarbyl group. In embodiments, $R^{k1}$ and/or $R^{k1}$ can be a $C_1$ to $C_{30}$ organyl group; alternatively, a $C_1$ to $C_{30}$ organyl group consisting of inert functional groups; alternatively, a $C_1$ to $C_{30}$ hydrocarbyl group; alternatively, a $C_1$ to $C_{20}$ organyl group; alternatively, a $C_1$ to $C_{20}$ organyl group consisting of inert functional groups; alternatively, a $C_1$ to $C_{20}$ hydrocarbyl group; alternatively, a $C_1$ to $C_{10}$ organyl group; alternatively, $C_1$ to $C_{10}$ organyl group consisting of inert functional groups; alternatively, a $C_1$ to $C_{10}$ hydrocarbyl group; alternatively, a $C_1$ to $C_5$ organyl group; alternatively, a $C_1$ to $C_5$ organyl group consisting of inert functional groups; or alternatively, a $C_1$ to $C_5$ hydrocarbyl group.

In some embodiments, the α-dione is an acyclic α-dione; both $R^{k1}$ and $R^{k2}$ are acyclic. In other embodiments, α-dione can be a semi-cyclic α-dione; $R^{k1}$ and/or $R^{k2}$ are, or comprise, a cyclic structure but are not connected through a ring or ring system. In yet other embodiments, the α-dione is a cyclic α-dione; $R^{k1}$ and $R^{k2}$ are connected to form a ring or ring system containing both carbon atoms of the α-dione group. In some semi-cyclic and/or cyclic α-dione embodiments, the ring or ring system can be saturated. In other semi-cyclic and/or cyclic α-dione embodiments, the ring or ring system can contain carbon-carbon double bonds. In further semi-cyclic and/or cyclic α-dione embodiments, the ring system can be a bicyclic ring system. In yet other semi-cyclic and/or cyclic α-dione embodiments, the ring or ring system can comprise an aromatic ring or an aromatic ring structure.

In acyclic α-dione embodiments, the α-dione can be 2,3-butanedione, a substituted 2,3-butanedione, 2,3-pentanedione, a substituted 2,3-pentanedione, 2,3-hexanedione, a substituted 2,3-hexanedione, 3,4-hexanedione, or a substituted 3,4-hexanedione. In some embodiments, the α-dione can be 2,3-butanedione, 2,3-pentanedione, 2,3-hexanedione, or 3,4-hexanedione. In further embodiments, the α-dione can be 2,3-butanedione; alternatively, 2,3-pentanedione; alternatively, 2,3-hexanedione; or alternatively, 3,4-hexanedione.

In aromatic semi-cyclic α-dione embodiments, the α-dione can be benzil or a substituted benzil. In other embodiments, the α-dione can be benzil.

In saturated cyclic α-dione embodiments, the α-dione can be 1,2-cyclobutanedione, a substituted 1,2-cyclobutanedione, 1,2-cyclopentanedione, a substituted 1,2-cyclopentanedione, 1,2-cyclohexanedione, a substituted 1,2-cyclohexanedione, 1,2-cycloheptanedione, and a substituted 1,2-cycloheptanedione. In some saturated cyclic α-dione embodiments, the α-dione can be 1,2-cyclopentanedione, a substituted 1,2-cyclopentanedione, 1,2-cyclohexanedione, or a substituted 1,2-cyclohexanedione. In some saturated cyclic α-dione embodiments, the α-dione can be 1,2-cyclopentanedione, or 1,2-cyclohexanedione. In yet other embodiments, the α-dione can be 1,2-cyclopentanedione; or alternatively, 1,2-cyclohexanedione.

In saturated ring system α-dione embodiments, the α-dione can be bicyclo[2.2.1]hepta-1,2-dione, a substituted bicyclo[2.2.1]hepta-1,2-dione, bicyclo[2.2.2]octa-1,2-dione, a substituted bicyclo[2.2.2]octa-1,2-dione, or camphorquinone. In some saturated ring system embodiments, the α-dione can be bicyclo[2.2.1]hepta-1,2-dione, bicyclo[2.2.2]octa-1,2-dione, or camphorquinone. In yet other saturated ring system α-dione embodiments, the α-dione can be camphorquinone.

In unsaturated cyclic α-dione embodiments, the α-dione can be 1,2-benzoquinone, a substituted 1,2-benzoquinone, cyclohex-3-ene-1,2-dione, a substituted cyclohex-3-ene-1,2-dione, cyclopent-3-ene-1,2-dione, a substituted cyclopent-3-ene-1,2-dione, a cyclohex-4-ene-1,2-dione, a substituted cyclohex-4-ene-1,2-dione, 3,4-dihydro-1,2-naphthoquinone, a substituted 3,4-dihydro-1,2-naphthaquinone, 1,4-dihydronaphthoquinone, or a substituted 1,4-dihydronaphthoquinone. In some unsaturated cyclic α-dione embodiments, the α-dione can be 1,2-benzoquinone, cyclohex-3-ene-1,2-dione, cyclopent-3-ene-1,2-dione, cyclohex-4-ene-1,2-dione, 3,4-dihydronaphthoquinone, or 1,4-dihydronaphthoquinone. In other unsaturated ring α-dione embodiments, the α-dione can be 1,2-benzoquinone; alternatively, 3,4-dihydronaphthoquinone; or alternatively, 1,4-dihydronaphthano-quinone.

In aromatic ring system α-dione embodiments, the α-dione can be a 1,2-naphthoquinone, a substituted 1,2-naphthoquinone, 2,3-naphthoquinone, a substituted 2,3-naphthoquinone, acenaphthenequinone, a substituted acenaphthenequinone, phenanthrenequinone, a substituted phenanthrenequinone, pyrenequinone, or a substituted pyrenequinone. In some aromatic ring system α-dione embodiments, the α-dione can be 1,2-naphthoquinone, 2,3-naphthoquinone, acenaphthenequinone, phenanthrenequinone, or pyrenequinone. In other aromatic ring system α-dione embodiments, the α-dione can be acenaphthenequinone, phenanthrenequinone, or pyrenequinone. In yet other aromatic ring system α-dione embodiments, the α-dione can be 1,2-naphthoquinone; alternatively, 2,3-naphthoquinone; alternatively, acenaphthenequinone; alternatively, phenanthrenequinone; or alternatively, pyrenequinone.

Within the substituted α-dione embodiments, each substituent can independently be an organyl group, an organyl group consisting of inert functional groups, a hydrocarbyl group, or an inert functional group. In some embodiments, the organyl substituent(s) can be a $C_1$ to $C_{20}$ organyl group, a $C_1$ to $C_{20}$ organyl group consisting of inert functional groups, or a $C_1$ to $C_{20}$ hydrocarbyl group. In some substituted α-dione embodiments, the substituents can be a $C_1$ to $C_{10}$ organyl group, a $C_1$ to $C_{10}$ organyl group consisting of inert functional groups, or a $C_1$ to $C_{10}$ hydrocarbyl group. In other substituted α-dione embodiments, the substituent(s) can be a $C_1$ to $C_5$ organyl group, a $C_1$ to $C_5$ organyl group consisting of inert functional groups, or a $C_1$ to $C_5$ hydrocarbyl group. In further substituted α-dione embodiments, the substituent(s) can be a $C_1$ to $C_{20}$ organyl group; alternatively, a $C_1$ to $C_{10}$ organyl group; alternatively, a $C_1$ to $C_5$ organyl group; alternatively, a $C_1$ to $C_{20}$ organyl group consisting of inert functional groups; alternatively, a $C_1$ to $C_{10}$ organyl group consisting of inert functional groups; alternatively, a $C_1$ to $C_5$ organyl group consisting of inert functional groups; alternatively, a $C_1$ to $C_{20}$ hydrocarbyl group; alternatively, a $C_1$ to $C_{10}$ hydrocarbyl group; alternatively, a $C_1$ to $C_5$ hydrocarbyl group; or alternatively, an inert functional group. Independent of the carbon number of the organyl group, organyl group consisting of inert functional groups, and hydrocarbyl group, each organyl group, organyl group consisting of inert functional groups, and hydrocarbyl group substituent can be a primary, secondary, tertiary, or quaternary hydrocarbyl group. In some embodiments, each organyl group, organyl group consisting of inert functional groups, and hydrocarbyl group can be a primary group; alternatively, a secondary group; alternatively, a tertiary group; or alternatively, a quaternary group. Independent of the carbon number of the organyl group consisting of inert functional groups, the organyl group consisting of inert functional groups can comprise a halides, ether groups, or sulfide groups. In some embodiments, the organyl group consisting of inert functional groups can be a trifluoromethyl group; or alternatively, a trichloromethyl group. Independent of the carbon number of the hydrocarbyl group, each hydrocarbyl group substituent can independently be a methyl, ethyl, n-propyl (1-propyl), isopropyl (2-propyl), n-butyl (1-butyl), sec-butyl (2-butyl), isobutyl (2-methyl-1-propyl), tert-butyl (2-methyl-2-propyl), n-pentyl (1-pentyl), 2-pentyl, 3-pentyl, 2-methyl-1-butyl, tert-pentyl (2-methyl-2-butyl), 3-methyl-1-butyl, 3-methyl-2-butyl, neo-pentyl (2,3-dimethyl-1-propyl), or n-hexyl (1-hexyl) group. In embodiments, the inert functional group can be a halogen atom or an alkoxy group; alternatively, a halogen atom; or alternatively, an alkoxy group. In some embodiments, the halogen atom may be fluorine, chlorine, bromine or iodine; alternatively, chlorine; or alternatively, fluorine. In some embodiments, the alkoxy group can be a methoxy group; alternatively, an ethoxy group; alternatively, an isopropoxy group; or alternatively, a tert-butoxy group.

In embodiments, the α-diacyl compounds can have any Structure as indicated in Table 1. In other embodiments, the diacyl compound can have Structure 2, 3, 4, or 5; alternatively, Structure 6; alternatively, Structure 7, 8, or 9; alternatively, structure 10, 11, or 12; or alternatively, Structure 10.

TABLE 1

Example α-Diacyl Compounds

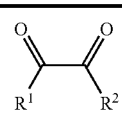

Structure 1

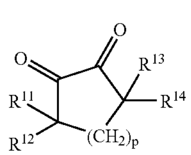

Structure 2

TABLE 1-continued

Example α-Diacyl Compounds

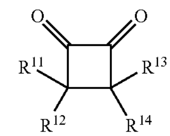

Structure 3

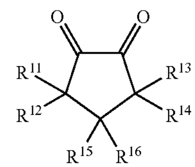

Structure 4

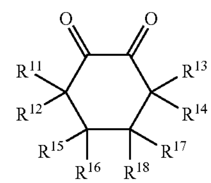

Structure 5

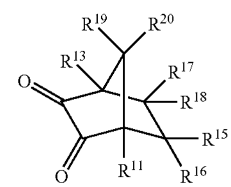

Structure 6

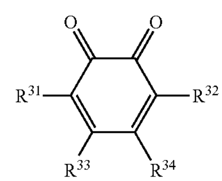

Structure 7

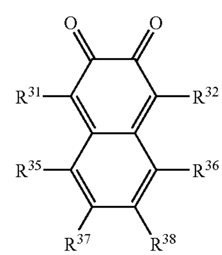

Structure 8

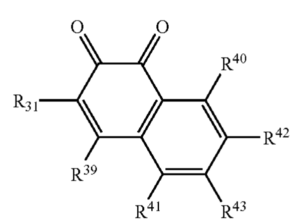

Structure 9

TABLE 1-continued

| Example α-Diacyl Compounds |
| --- |
| 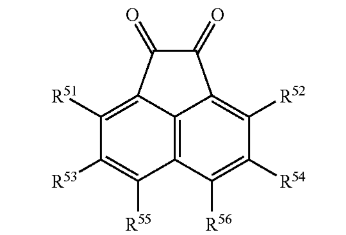 Structure 10 |
| 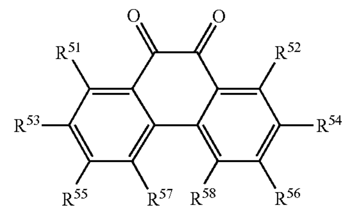 Structure 11 |
| 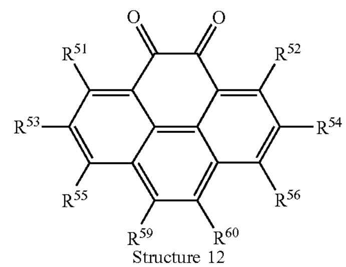 Structure 12 |

Within the Structures of Table 1, $R^1$, $R^2$, $R^{11}$ to/through $R^{20}$, $R^{31}$ to/through $R^{43}$, and $R^{51}$ to/through $R^{60}$ can each independently be hydrogen, an organyl group, an organyl group consisting of inert functional groups, or a hydrocarbyl group. The organyl group, organyl group consisting of inert functional groups, and hydrocarbyl group are generally described within the description of the α-diacyl compounds and can have any embodiment as described therein. In Structure 2, "p" can be a whole integer ranging from 1 to 10; alternatively, a whole integer ranging from 1 to 3; alternatively, 1; alternatively, 2; or alternatively, 3. In some embodiments, $R^1$, $R^2$, $R^{11}$ to/through $R^{20}$, $R^{31}$ to/through $R^{43}$, and $R^{51}$ to/through $R^{60}$ can be hydrogen. In some embodiments, the α-diacyl compound may have Structure 1 where $R^1$ is an organyl group, an organyl group consisting of inert functional groups, or a hydrocarbyl group, and $R^2$ is hydrogen.

Primary Amines

The primary amine(s) that can be utilized in the synthesis of the α-diimine metal complexes (and/or the intermediate α-acylimine compounds, α-acylimine metal complexes) can be any primary amine capable of forming an imine group when contacted with an acyl group. It should be noted that while the applicable primary amines are described in terms of the ability to form an imine group when contacted with an acyl group, such description is not intended to imply a method by which an imine group of an α-acylimine compound, α-acylimine metal complex, α-diimine compound, and/or α-diimine metal complex described herein are made. The language is intended to describe, to one skilled in the art, the particular primary amine(s) that can be utilized in the synthesis of an α-acylimine compound, α-acylimine metal complex, α-diimine compound, and/or α-diimine metal complex as described herein. The α-acylimine compound, α-acylimine metal complex, α-diimine compound, and/or α-diimine metal complexes can be produced using any method described herein.

Minimally, the primary amine comprises an —$NH_2$ group. In a further embodiment, the primary amine comprises an —$NH_2$ group and an organyl group; alternatively, comprises an —$NH_2$ group and a metal salt complexing group; alternatively, comprises an —$NH_2$ group, a metal salt complexing group and a linking group linking the metal salt complexing group to the —$NH_2$ group; alternatively, comprises an —$NH_2$ group and an organyl group consisting of inert functional groups; or alternatively, comprises an —$NH_2$ group and a hydrocarbyl group. In yet other embodiments, the primary amine consists of an —$NH_2$ group and an organyl group; alternatively, consists of an —$NH_2$ group, a metal salt complexing group and a linking group linking the metal salt complexing group to the —$NH_2$ group; alternatively, consists of an —$NH_2$ group and an organyl group consisting of inert functional groups; or alternatively, consists of an —$NH_2$ group and a hydrocarbyl group. The primary amines can be saturated, unsaturated, linear, branched, acyclic, cyclic, aromatic, and/or heteroaromatic.

In an aspect, the primary amine can comprise an —$NH_2$ group and organyl group; or alternatively, the primary amine can consist of an —$NH_2$ group and an organyl group. In the embodiments wherein the primary amine can comprise or consist of an —$NH_2$ group and organyl group, the organyl group can be a $C_1$ to $C_{30}$ organyl group; alternatively, a $C_1$ to $C_{20}$ organyl group; alternatively, a $C_1$ to $C_{10}$ organyl group; or alternatively, a $C_1$ to $C_5$ organyl group. The organyl group can be saturated, unsaturated, linear, branched, acyclic, cyclic, aromatic, and/or heteroaromatic. In some embodiments, the primary amine comprising or consisting of an —$NH_2$ group and organyl groups can have Structure 1a indicated below:

$$R^{a1}NH_2 \qquad \text{Structure 1a}$$

wherein $R^{a1}$ represents the organyl group. In embodiments, that utilize a second primary amine comprising or consisting of an —$NH_2$ group and organyl groups, the second primary amine comprising or consisting of an —$NH_2$ group and organyl groups can be designated as having Structure 2a indicated below:

$$R^{a1'}NH_2 \qquad \text{Structure 2a}$$

wherein $R^{a1'}$ represents the organyl group.

In an aspect, the primary amine can comprise an —$NH_2$ group and an organyl group consisting of inert functional groups; or alternatively, the primary amine can consist of an —$NH_2$ group and an organyl group consisting of inert functional groups. In the embodiments wherein the primary amine can comprise or consist of an —$NH_2$ group and an organyl group consisting of inert functional groups, the organyl group consisting of inert functional groups can be a $C_1$ to $C_{30}$ organyl group consisting of inert functional groups; alternatively, a $C_1$ to $C_{20}$ organyl group consisting of inert functional groups; alternatively, a $C_1$ to $C_{10}$ organyl group consisting of inert functional groups; or alternatively, a $C_1$ to $C_5$ organyl group consisting of inert functional groups. The organyl group consisting of inert functional groups can be saturated, unsaturated, linear, branched, acyclic, cyclic, aromatic, and/or heteroaromatic. In some embodiments, the inert functional groups can be ether groups; alternatively, sulfide groups; alternatively, halide atoms; or alternatively, hydrocarbyl groups. In some embodiments, the primary amine comprising or consisting of an —$NH_2$ group and an organyl group consisting of inert functional groups can have Structure 1a wherein $R^{a1}$ represents the organyl group consisting of inert functional groups. In embodiments that utilize a second primary amine comprising or consisting of an —$NH_2$ group and an organyl group consisting of inert functional groups, the second primary amine comprising or consisting of an —$NH_2$ group and an organyl group consisting of inert functional groups can be designated as having Structure 2a wherein $R^{a1'}$ represents the organyl group consisting of inert functional groups.

In some embodiments, the organyl group consisting of inert functional groups can be an aromatic ring or aromatic ring system having one or more inert functional group substituent(s). In these embodiments, the aromatic ring or aromatic ring system can be a substituted benzene ring (a substituted phenyl group); or alternatively, a substituted naphthalene ring (a substituted naphthyl group). The aromatic ring or aromatic ring system inert functional group substituent(s) can be an organyl group having halogen atoms, an ether group (alkoxy group or etheryl group), or a sulfide group (sulfidyl group). In some embodiments, the aromatic ring inert functional group substituent(s) can be a trifluoromethyl group, a $C_1$ to $C_5$ ether group a $C_1$ to $C_5$ sulfide group or a halogen atom. In some embodiments, the halogen atom may be fluorine, chlorine, bromine or iodine; alternatively, chlorine; or alternatively, fluorine. In some embodiments, the alkoxy group can be a methoxy group; alternatively, an ethoxy group; alternatively, an isopropoxy group; or alternatively, a tert-butoxy group. Non-limiting examples of a primary amine consisting of an aromatic ring having one or more inert functional groups include substituted anilines wherein the substituents can be the substituents as described above. Non-limiting examples are primary amines consisting of an aromatic ring or aromatic ring systems having one or more inert functional groups such as 2-methoxyaniline, 3-methoxyaniline, 4-methoxyanaline, 2-chloroaniline, 3-chloroaniline, 4-chloroanaline, 2-fluoroaniline, 3-fluoroaniline, 4-fluoroanaline, 2,6-trifluoromethylaniline, or dimethyl-4-methoxyaniline.

In some embodiments, a primary amine comprising or consisting of an —$NH_2$ group and an organyl group consisting of inert functional groups can have Structure 3a as indicated below:

Structure 3a

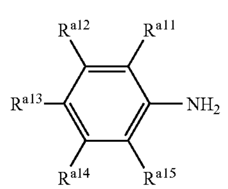

wherein $R^{a11}$ to/through $R^{a15}$ represent the substituents of the aromatic ring. In embodiments that utilize a second primary amine comprising or consisting of an —$NH_2$ group and an organyl group consisting of inert functional groups, the second primary amine comprising or consisting of an —$NH_2$ group and an organyl group consisting of inert functional groups can be designated as having Structure 4a indicated below:

Structure 4a

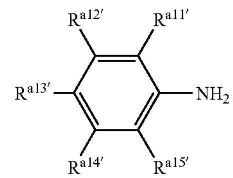

wherein $R^{a11'}$ to/through $R^{a15'}$ represent the substituents of the aromatic ring.

In an aspect, the primary amine can comprise an —$NH_2$ group and hydrocarbyl group; or alternatively, the primary amine can consist of an —$NH_2$ group and a hydrocarbyl group. In embodiments wherein the primary amine can comprise or consist of an —$NH_2$ group and hydrocarbyl group, the hydrocarbyl group can be a $C_1$ to $C_{30}$ hydrocarbyl group; alternatively, a $C_1$ to $C_{20}$ hydrocarbyl group; alternatively, a $C_1$ to $C_{10}$ hydrocarbyl group; or alternatively, a $C_1$ to $C_5$ hydrocarbyl group. Independently, the hydrocarbyl group can be a saturated, unsaturated, acyclic, cyclic, linear, branched, and/or aromatic. In some embodiments, the primary amine comprising or consisting of an —$NH_2$ group and a hydrocarbyl group can have Structure 1a wherein $R^{a1}$ represents the hydrocarbyl group. In embodiments that utilize a second primary amine comprising or consisting of an —$NH_2$ group and an hydrocarbyl group, the second primary amine comprising or consisting of an —$NH_2$ group and an hydrocarbyl group can be designated as having Structure 2a wherein $R^{a1'}$ represents the hydrocarbyl group.

Acyclic hydrocarbyl group embodiments can include $C_1$ to $C_{30}$ acyclic hydrocarbyl groups; alternatively, $C_1$ to $C_{20}$ acyclic hydrocarbyl groups; alternatively, $C_1$ to $C_{10}$ acyclic hydrocarbyl groups; or alternatively, $C_1$ to $C_5$ acyclic hydrocarbyl groups. The acyclic hydrocarbyl groups can be linear; or alternatively, branched. Independent of the carbon number of the acyclic hydrocarbyl group, the acyclic hydrocarbyl group can be a primary, secondary, tertiary, or quaternary hydrocarbyl group. In some embodiments, the acyclic hydrocarbyl group can be a primary hydrocarbyl group; alternatively, a secondary hydrocarbyl group; alternatively, a tertiary hydrocarbyl group; or alternatively, a quaternary hydrocarbyl group. In an aspect, the acyclic hydrocarbyl groups can be a methyl, ethyl, n-propyl (1-propyl), isopropyl (2-propyl), n-butyl (1-butyl), sec-butyl (2-butyl), isobutyl (2-methyl-1-propyl), tert-butyl (2-methyl-2-propyl), n-pentyl (1-pentyl), 2-pentyl, 3-pentyl, 2-methyl-1-butyl, tert-pentyl (2-methyl-2-butyl), 3-methyl-1-butyl, 3-methyl-2-butyl, neo-pentyl (2,3-dimethyl-1-propyl), or n-hexyl (1-hexyl) group. Specific, non-limiting, examples of primary amines consisting of an —$NH_2$ group and an acyclic hydrocarbyl groups include methyl amine, ethyl amine, n-propylamine, isopropyl amine, n-butyl amine, sec-butylamine (2-butylamine), isobutylamine (2-methyl-1-propylamine), tert-butylamine (2-methyl-2-propylamine), n-pentylamine, neopentylamine, and n-hexylamine. One skilled in the art will readily recognize which hydrocarbyl groups belong (and which amines have a hydrocarbyl group that belongs) to the primary, secondary, tertiary, or quaternary hydrocarbyl group classes.

Cyclic hydrocarbyl group embodiments can include embodiments wherein the hydrocarbyl group is cyclic (the —$NH_2$ group is attached to a carbon that is a member of a ring or ring system) or embodiments wherein the hydrocarbyl group comprises a cyclic group (the —$NH_2$ group is attached to a carbon atom that is not a member of a ring or ring system). Regardless of whether the cyclic hydrocarbyl group is cyclic or comprises a cyclic group, the cyclic hydrocarbyl group can be $C_4$ to $C_{30}$ cyclic hydrocarbyl group; alternatively, a $C_4$ to $C_{20}$ cyclic hydrocarbyl group; or alternatively, a $C_4$ to $C_{10}$ cyclic hydrocarbyl group. In embodiments, the cyclic hydrocarbyl group can comprise a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, an adamantyl group, or a substituted adamantyl group. In some embodiments, the cyclic hydrocarbyl group can be a cyclobutyl group; alternatively, a cyclopentyl group; alternatively, a cyclohexyl group; alternatively, a cycloheptyl, or alternatively, an adamantyl group. In some embodiments, the primary amine comprising an —$NH_2$ group and cyclic hydrocarbyl group can be a substituted cyclopentylamine, a substituted cyclohexylamine, a substituted cyclohexylamine, or a substituted adamantylamine. In other embodiments, the primary amine comprising or consisting of an —$NH_2$ group and cyclic hydrocarbyl group can be a substituted cyclopentylamine; alternatively, a substituted cyclohexylamine; or alternatively, a substituted adamantylamine. In yet other embodiments, the primary amine comprising or consisting of an —$NH_2$ group and cyclic hydrocarbyl group can be cyclopentylamine, cyclohexylamine, cycloheptylamine, or adamantylamine. In yet other embodiments, the primary amine consisting of a cyclic hydrocarbyl group can be cyclopentylamine; alternatively, cyclohexylamine; or alternatively, adamantylamine.

Aromatic hydrocarbyl group embodiments can include embodiments wherein the hydrocarbyl group is aromatic (the —$NH_2$ group is attached to a carbon that is a member of an aromatic ring or ring system) or embodiments wherein the hydrocarbyl group comprises an aromatic group (the —$NH_2$ group is attached to a carbon atom that is not a member of a aromatic ring or aromatic ring system). Regardless of whether the aromatic hydrocarbyl group of the primary amine is aromatic or comprises an aromatic group, the aromatic hydrocarbyl group can be a $C_6$ to $C_{30}$ aromatic hydrocarbyl group; alternatively, a $C_6$ to $C_{20}$ aromatic hydrocarbyl group; or alternatively, a $C_6$ to $C_{10}$ aromatic hydrocarbyl group. In some embodiments, the aromatic hydrocarbyl group can be a phenyl group, substituted phenyl group, a naphthyl group, a substituted naphthyl group, a benzyl group, or a substituted benzyl group. In other embodiments, the aromatic hydrocarbyl group can be a phenyl group, a naphthyl group, or a benzyl group. In yet other embodiments, the aromatic hydrocarbyl group is a phenyl group; alternatively, a naphthyl group; or alternatively, a benzyl group. In further embodiments, the aromatic hydrocarbyl group can be a substituted phenyl group; alternatively, a substituted naphthyl group; or alternatively, a substituted benzyl group.

In embodiments, the primary amine comprising an —$NH_2$ group and an aromatic hydrocarbyl group can be aniline, a substituted aniline, 1-naphthylamine, a substituted 1-naphthylamine, 2-naphthylamine, a substituted 2-naphthylamine, benzyl amine, or a substituted benzyl amine. In some embodiments, the primary amine comprising an —$NH_2$ group and an aromatic hydrocarbyl group can be a substituted aniline, a substituted 1-naphthylamine, a substituted 2-naphthylamine, or a substituted benzyl amine. In other embodiments, the primary amine comprising an —$NH_2$ group and an aromatic hydrocarbyl group can be a substituted aniline; alternatively; a substituted 1-naphtylamine; alternatively, a substituted 2-naphthylamine; or alternatively, a substituted benzyl amine. In other embodiments, the primary amine consisting of an —$NH_2$ group and an aromatic hydrocarbyl group can be aniline, 1-naphthylamine, 2-naphthylamine, or benzyl amine. In yet other embodiments, the primary amine can be aniline; 1-naphthylamime; alternatively, 2-napthylamine; or alternatively, benzyl amine. In further embodiments, the primary amine can be aniline, or a substituted aniline. In embodiments, the substituted aniline can be substituted at the 2-position. In some embodiments, the substituted aniline is substituted at the 2- and 6-position; alternatively, at the 2- and 5-position; or alternatively, at the 2-, 4-, and 6-positions. In other embodiments, the substituents at the 2-position, at the 2- and 6-position, at the 2- and 5-positions, or at the 2-, 4-, and 6-positions can independently be a primary substituent; alternatively; a secondary substituent; alternatively, a tertiary substituent; or alternatively, a quaternary substituent. In some embodiments, the primary amine consisting of an —$NH_2$ group and an aromatic hydrocarbyl group can be 2,6-dimethylanaline, 2,6-diethylaniline, 2,6-dilsopropylaniline, or 2,6-di-tert-butylaniline. In other embodiments, the primary amine consisting of an —$NH_2$ group and an aromatic hydrocarbyl group can be 2,6-dimethylanaline, 2,6-diethylaniline, or 2,6-dilsopropylaniline. In yet other embodiments, the primary amine consisting of an —$NH_2$ group and an aromatic hydrocarbyl group can be 2,6-dimethylanaline; alternatively, 2,6-diethylaniline; alternatively, 2,6-diisopropylaniline; alternatively, 2,6-di-tert-butylanaline; alternatively, 2,5-di-tert-butylanaline; alternatively, 2-isopropyl-6-methylanaline; or alternatively, 2,4,6-trimethylanaline.

In some embodiments, the primary amine comprising or consisting of an —$NH_2$ group and an aromatic hydrocarbyl group can have Structure 3a wherein $R^{a11}$ to/through $R^{a15}$ represent the substituents of the aromatic hydrocarbyl group. In embodiments that utilize a second primary amine comprising or consisting of an —$NH_2$ group and an aromatic hydrocarbyl group, the second primary amine comprising or consisting of an —$NH_2$ group and an aromatic hydrocarbyl group can be designated as having Structure 4a wherein $R^{a11'}$ to/through $R^{a15'}$ represent the substituents of the aromatic hydrocarbyl group.

In embodiments, each substituent of the cyclic hydrocarbyl group or the aromatic hydrocarbyl group can independently be a $C_1$ to $C_{20}$ hydrocarbyl group; alternatively, a $C_1$ to $C_{10}$ hydrocarbyl group; or alternatively, a $C_1$ to $C_5$ hydrocarbyl group. Independent of the carbon number of the cyclic hydrocarbyl substituent, the substituents of the cyclic hydrocarbyl group or the aromatic hydrocarbyl group can be primary, secondary, tertiary, or quaternary hydrocarbyl groups. In some embodiments, a cyclic hydrocarbyl substituent or an aromatic hydrocarbyl substituent can be a primary hydrocarbyl group; alternatively, a secondary hydrocarbyl group; alternatively, a tertiary hydrocarbyl group; or alternatively, a quaternary hydrocarbyl group. In some embodiments, the cyclic hydrocarbyl group substituent or an aromatic hydrocarbyl substituent can be a methyl, ethyl, n-propyl (1-propyl), isopropyl (2-propyl), n-butyl (1-butyl), sec-butyl (2-butyl), isobutyl (2-methyl-1-propyl), tert-butyl (2-methyl-2-propyl), n-pentyl (1-pentyl), 2-pentyl, 3-pentyl, 2-methyl-1-butyl, tert-pentyl (2-methyl-2-butyl), 3-methyl-1-butyl, 3-methyl-2-butyl, neo-pentyl (2,3-dimethyl-1-propyl), or n-hexyl (1-hexyl) group. One skilled in the art will readily recognize which cyclic hydrocarbyl group substituents or aromatic hydrocarbyl substituents belong to the primary, secondary, tertiary, or quaternary hydrocarbyl group classes.

In substituted phenyl group embodiments, the substituted phenyl hydrocarbyl group can be a 2-substituted phenyl group; alternatively, a 2,6-disubstituted phenyl group; alternatively, a 2,5-disubstituted phenyl group; or alternatively, a 2,4,6-trisubstituted phenyl group. In some embodiments, the substituted phenyl hydrocarbyl group can be a 2,6-dimethylphenyl group, a 2,6-diethylphenyl group, a 2,6-diisopropylphenyl group, or a 2,6-di-tert-butylphenyl group. In yet other embodiments, the substituted phenyl hydrocarbyl group can be a 2,6-dimethylphenyl group, a 2,6-diethylphenyl group, or a 2,6-diisopropylphenyl group. In further embodiments, the substituted phenyl hydrocarbyl group can be a 2,6-dimethylphenyl group; alternatively, a 2,6-diethylphenyl group; alternatively, a 2,6-diisopropylphenyl group; alternatively, a 2,6-di-tert-butylphenyl group; alternatively, a 2,5-di-tert-butylphenyl group; alternatively, a 2-isopropyl-6-methyl group; or alternatively, a 2,4,6-trimethylphenyl group (mesityl group).

In an embodiment, the primary amine can comprise an $—NH_2$ group and a metal salt complexing group. In another embodiment, the primary amine can comprise an $—NH_2$ group, a metal salt complexing group, and a linking group linking the metal salt complexing group to the $—NH_2$ group. In yet another aspect the primary amine can consist of a metal salt complexing group, and a linking group linking the metal salt complexing group to the $—NH_2$ group. Generally, the metal salt complexing group and the linking group are independent elements. Thus, the primary amine comprising or consisting of an $—NH_2$ group, a metal salt complexing group, and a linking group linking the metal salt complexing group to the $—NH_2$ group can be described using any combination of the metal salt complexing group described herein and the linking group linking the metal salt complexing group to the $—NH_2$ group described herein.

In embodiments, the primary amine comprising or consisting of an $—NH_2$ group, a metal salt complexing group, and a linking group linking the metal salt complexing group to the $—NH_2$ group can have Structure 5a:

$$Q—L—NH_2 \qquad \text{Structure 5a}$$

where Q represents the metal salt complexing group and L represents the linking group. In some embodiments, the metal salt complexing group and the linking group can have structures indicated in Table 2 and Table 3, respectively.

The metal salt complexing group, Q, can be any group comprising a heteroatom capable of complexing with the metal salt. The linking group, L, can be any group capable of linking the metal salt complexing group to the $—NH_2$ group. The linking group includes all atoms between the primary amine nitrogen atom, the $—NH_2$, and the metal salt complexing group. If the metal salt complexing group is acyclic, the linking group includes all atoms between the primary amine nitrogen atom and the heteroatom of the metal salt complexing functional group. For example, in N,N-dimethylethylenediamine the linking group is $—CH_2CH_2—$ and the metal salt complexing group is the N,N-dimethylaminyl group, and in 2-phenoxyethylamine the linking group is $—CH_2CH_2—$ and the metal salt complexing group is the phenoxy group. However, if the heteroatom of the metal salt complexing group is contained within a ring, the linking group includes all the atoms between the primary amine nitrogen atom and the first atom contained within the ring containing the metal salt complexing heteroatom of the metal salt complexing group. For example, in 2-(2-aminoethyl)pyridine the linking group is $—CH_2CH_2—$ and the metal salt complexing group is the 2-pyridinyl group, in 1-(2-aminoethyl)piperidine the linking group is $—CH_2CH_2—$ and the metal salt complexing group is the 1-piperidinyl group, and in 2-aminopyridine the linking group is a bond and the metal salt complexing group is the 2-pyridinyl group.

The metal salt complexing group, Q, can be any group comprising a heteroatom capable of complexing with the metal salt. In embodiments, the metal salt complexing group can be a $C_2$ to $C_{30}$ group comprising a heteroatom; alternatively, a $C_2$ to $C_{20}$ group comprising a heteroatom; alternatively, a $C_2$ to $C_{10}$ group comprising a heteroatom; or alternatively, a $C_2$ to $C_5$ group comprising a heteroatom. In some embodiments, the metal salt complexing heteroatom of the metal salt complexing group can be oxygen, sulfur, nitrogen, or phosphorus. In other embodiments, the metal salt complexing heteroatom of the metal salt complexing group can be oxygen or sulfur. In yet other embodiments, the metal salt complexing heteroatom of the metal salt complexing group can be nitrogen, or phosphorus. In further embodiments, the metal salt complexing heteroatom of the metal salt complexing group can be oxygen; alternatively, sulfur; alternatively, nitrogen; or alternaively, phosphorus. Optionally, the metal salt complexing group can contain additional heteroatom which do not complex the metal salt in α-diimine metal complex such as inert heteroatoms (e.g. halides, and silicon) and/or additional metal salt complexing heteroatom(s) which do not complex with the metal salt.

In particular embodiments, the metal salt complexing group can be a dialkyl aminyl group, a diphenyl aminyl group, a substituted diphenyl aminyl group, an alkyl phenyl aminyl group, an alkyl substituted phenyl aminyl group, a dialkyl phosphinyl group, a diphenyl phosphinyl group, a substituted diphenyl phosphinyl group, an alkyl phenyl phosphinyl group, an alkyl substituted phenyl phosphinyl group, an alkyl etheryl group, a phenyl etheryl group, a substituted phenyl etheryl group, an alkyl sulfidyl group, a phenyl sulfidyl group, a substituted phenyl sulfidyl group, a furanyl group, a substituted furanyl group, a thiophenyl group, a substituted thiophenyl group, a tetrahydrofuranyl group, a substituted tetrahydrofuranyl group, a thiophanyl group, a substituted thiophanyl group, a pyridinyl group, a substituted pyridinyl group, a morphilinyl group, a substituted morphilinyl group, a pyranyl group, a substituted pyranyl group, a tetrahydropyranyl group, a substituted tetrahydropyranyl group, a quinolinyl group, a substituted quinolinyl group, a pyrrolyl group, a substituted pyrrolyl group, a pyrrolidinyl group, a substituted pyrrolidinyl group, a piperidinyl group, or a substituted piperidinyl group. In embodiments, the metal salt complexing group can be a dialkyl aminyl group, a diphenyl aminyl group, a dialkyl phosphinyl group, a diphenyl phosphinyl group, an alkyl etheryl group, a phenyl etheryl group, an alkyl sulfidyl group, a phenyl sulfidyl group, a furanyl group, a thiophenyl group, a tetrahydrofuranyl group, a thiophanyl group, a pyridinyl group, a morphilinyl group, a pyranyl group, a tetrahydropyranyl group, a quinolinyl group, a pyrrolyl group, a pyrrolidinyl group, or a piperidinyl group. In some embodiments, the metal salt complexing group can be a dialkyl aminyl group, a diphenyl aminyl group, a substituted diphenyl aminyl group, a dialkyl phosphinyl group, a diphenyl phosphinyl group, a substituted diphenyl phosphinyl group, an alkyl etheryl group, a phenyl etheryl group, a substituted phenyl etheryl group, an alkyl sulfidyl group, a phenyl sulfidyl group, a substituted phenyl sulfidyl group, a pyridinyl group, a substituted pyridinyl group, a morphilinyl group, or a substituted morphilinyl group; alternatively, a dialkyl aminyl group, a diphenyl aminyl group, a dialkyl phosphinyl group, a diphenyl phosphinyl group, an alkyl etheryl group, a phenyl etheryl group, an alkyl sulfidyl group, a phenyl sulfidyl group, a pyridinyl group, or a morphilinyl group; alternatively, a dialkyl aminyl group, a diphenyl aminyl group, a substituted diphenyl aminyl group, a dialkyl phosphinyl group, a diphenyl phosphinyl group, or a substituted diphenyl phosphinyl group; alternatively, a dialkyl aminyl group, a diphenyl aminyl group, a dialkyl phosphinyl group, a diphenyl phosphinyl group; or alternatively, a diphenyl aminyl group, a substituted diphenyl aminyl group, a diphenyl phosphinyl group, a substituted diphenyl phosphinyl group; alternatively, a diphenyl aminyl group, a substituted diphenyl aminyl group, a diphenyl phosphinyl group, a substituted diphenyl phosphinyl group, a phenyl sulfidyl group, a substituted phenyl sulfidyl group, a pyridinyl group, or a substituted pyridinyl group; or alternatively, a diphenyl aminyl group, a diphenyl phosphinyl group, a phenyl sulfidyl group, or a pyridinyl group. In other embodiments, the metal salt complexing group can be a dialkyl aminyl group or a dialkyl phosphinyl group; alternatively, a diphenyl aminyl group or a diphenyl phosphinyl group; alternatively, a substituted diphenyl aminyl group or a substituted diphenyl phosphinyl group; alternatively, a 2-pyridinyl group or a substituted 2-pyridinyl group; alternatively, an alkyl etheryl group, a phenyl etheryl group, a substituted phenyl etheryl group, a alkyl sulfidyl group, a phenyl sulfidyl group, or a substituted sulfidyl group; alternatively, an alkyl etheryl group or an alkyl sulfidyl group; alternatively, a phenyl etheryl group, a substituted phenyl etheryl group, a phenyl sulfidyl group, or a substituted sulfidyl group; alternatively, a phenyl etheryl group or a substituted phenyl etheryl group; alternatively, a phenyl sulfidyl group, a substituted phenyl sulfidyl group; alternatively, a phenyl sulfidyl group; alternatively, a substituted phenyl sulfidyl group; alternatively, a furanyl group, a substituted furanyl group, a thiophenyl group or a substituted thiophenyl group; alternatively, a 1-morphilinyl group or a substituted 1-morphilinyl group; alternatively, a 2-morphilinyl group or a substituted 2-morphilinyl group; alternatively, a 2-pyranyl group or a substituted 2-pyranyl group; alternatively, a 2-tetrahydropyranyl group, a substituted 2-tetrahydropyranyl group; alternatively, a 1-piperidinyl group, or a substituted 1-piperidinyl group; alternatively, a 1-pyrrolidinyl group, a substituted 1-pyrrolidinyl group; alternatively, a 2-pyrrolidinyl group, a substituted 2-pyrrolidinyl group; alternatively, a 2-piperidinyl group, or a substituted 2-piperidinyl group; alternatively, a 2-quinolinyl group or a substituted 2-quiolinyl group; alternatively, a 1-pyrrolyl group or a substituted 1-pyrrolyl group; alternatively, a 2-pyrrolyl group or a substituted 2-pyrrolyl group; alternatively, a 2-tetrahydrofuranyl group or a substituted 2-tetrahydrofuranyl group; or alternatively, a 2-thiophanyl group or a substituted 2-thiophanyl group. In yet other embodiments, the metal salt complexing group can be a diphenyl aminyl group; alternatively, a substituted diphenyl aminyl group; alternatively, a diphenyl phosphinyl group; or alternatively, a substituted diphenyl phosphinyl group.

The alkyl group(s) of the aminyl, phosphinyl, ethyl, or sulfidyl metal salt complexing group embodiments can independently be a $C_1$ to $C_{20}$ organyl group consisting of inert functional groups; alternatively, a $C_1$ to $C_{10}$ organyl group consisting of inert functional groups; or alternatively, a $C_1$ to $C_5$ organyl group consisting of inert functional groups; $C_1$ to $C_{20}$ hydrocarbyl group; alternatively, a $C_1$ to $C_{10}$ hydrocarbyl group; or alternatively, a $C_1$ to $C_5$ hydrocarbyl group. The substituted phenyl groups of the aminyl, phosphinyl, ethyl, or sulfidyl metal salt complexing group embodiments can independently be a $C_6$ to $C_{20}$ phenyl group; or alternatively, a $C_6$ to $C_{15}$ phenyl group. Independently, the alkyl groups of the aminyl, phosphinyl, ethyl, or sulfidyl metal salt complexing groups can be primary, secondary, tertiary, or quaternary hydrocarbyl groups. In some embodiments, the alkyl group of the aminyl, phosphinyl, ethyl, or sulfidyl metal salt complexing group can be a primary hydrocarbyl group; alternatively, a secondary hydrocarbyl group; alternatively, a tertiary hydrocarbyl group; or alternatively, a quaternary hydrocarbyl group.

Each substituent of the substituted metal salt complexing group embodiments can independently be a $C_1$ to $C_{10}$ organyl group, a $C_1$ to $C_{10}$ organyl group consisting of inert functional groups, a $C_1$ to $C_{10}$ hydrocarbyl group, or an inert functional group. In some embodiments, the substituents of the substituted metal salt complexing group can be $C_1$ to $C_5$ organyl groups, a $C_1$ to $C_5$ organyl groups consisting of inert functional groups, $C_1$ to $C_5$ hydrocarbyl groups, or an inert functional group. In other embodiments, the substituents of the substituted metal salt complexing group can be $C_1$ to $C_{10}$ organyl groups; alternatively, a $C_1$ to $C_{10}$ organyl groups consisting of inert functional groups; alternatively, a $C_1$ to $C_{10}$ hydrocarbyl groups; alternatively, a $C_1$ to $C_5$ organyl groups; alternatively, a $C_1$ to $C_5$ hydrocarbyl groups; or alternatively, inert functional groups. Independent of the carbon number of the organyl group, and the organyl group consisting of inert functional groups each organyl group and organyl group consisting of inert functional groups can be a primary, secondary, tertiary, or quaternary hydrocarbyl group. In some embodiments, each organyl group and organyl group consisting of inert functional groups can be a primary group; alternatively, a secondary group; alternatively, a tertiary group; or alternatively, a quaternary group. Independent of the carbon number of the organyl group consisting of inert functional groups, the organyl group consisting of inert functional groups can comprise a halide, an ether group (alkoxy group or etheryl group), or a sulfide group (sulfidyl group). In some embodiments, the organyl group consisting of inert functional groups can be a trifluoromethyl group; or alternatively, a trichloromethyl group. In embodiments, the inert functional group can be a halogen atom or an alkoxy group; alternatively, a halogen atom; or alternatively, an alkoxy group. In some embodiments, the halogen atom may be fluorine, chlorine, bromine or iodine; alternatively, chlorine; or alternatively, fluorine. In some embodiments, the alkoxy group can be a methoxy group; alternatively, an ethoxy group; alternatively, an isopropoxy group; or alternatively, a tert-butoxy group.

Independent of the carbon number of the hydrocarbyl substituent, the alkyl group or the substituent(s) of the substituted metal salt complexing group can be a primary, secondary, tertiary, or quaternary hydrocarbyl group. In some embodiments, the alkyl group or the substituent(s) of the substituted metal salt complexing group can be a primary hydrocarbyl group; alternatively, a secondary hydrocarbyl group; alternatively, a tertiary hydrocarbyl group; or alternatively, a quaternary hydrocarbyl group. In some embodiments, the alkyl group or the hydrocarbyl substituents of the substituted metal salt complexing group can be a methyl, ethyl, n-propyl (1-propyl), isopropyl (2-propyl), n-butyl (1-butyl), sec-butyl (2-butyl), isobutyl (2-methyl-1-propyl), tert-butyl (2-methyl-2-propyl), n-pentyl (1-pentyl), 2-pentyl, 3-pentyl, 2-methyl-1-butyl, tert-pentyl (2-methyl-2-butyl), 3-methyl-1-butyl, 3-methyl-2-butyl, neo-pentyl (2,3-dimethyl-1-propyl), or n-hexyl (1-hexyl) group. One skilled in the art will readily recognize which alkyl group or the hydrocarbyl substituents of the substituted metal salt complexing group belong to the primary, secondary, tertiary, or quaternary hydrocarbyl group classes.

The linking group linking the metal salt complexing group to the $—NH_2$ group can be a bond, an organyl group, and organyl group consisting of inert functional groups, or a hydrocarbyl group. In other embodiments, the linking group can be a bond; alternatively, an organyl group; alternatively, an organyl group consisting of inert functional groups; or alternatively, a hydrocarbyl group. In some embodiments, the linking group can be a $C_1$ to $C_{10}$ organyl group; or alternatively, a $C_1$ to $C_5$ organyl group. In some embodiments, the linking group linking the metal salt complexing group to the $—NH_2$ group can be a $C_1$ to $C_{10}$ organyl group consisting of inert functional groups; or alternatively, a $C_1$ to $C_5$ organyl group consisting of inert functional groups. In other embodiments, the linking group linking the metal salt complexing group to the $—NH_2$ group can be a $C_1$ to $C_{10}$ hydrocarbyl group; or alternatively, a $C_1$ to $C_5$ hydrocarbyl group.

In some embodiments, the hydrocarbyl linking group can be $—(CR^LR^L)_m—$ where $R^L$ and $R^L$ are independently hydrogen, methyl, ethyl, propyl, isopropyl, or butyl groups and m can be an integer from 1 to 5. In other embodiments, the linking group can be a methylene group ($—CH_2—$), an ethylene group ($—CH_2CH_2—$), a propyl group ($—CH_2CH_2CH_2—$), a $—CH(CH_3)CH_2—$ group, $—C(CH_3)_2—$ group, or a butylene group ($—CH_2CH_2CH_2—CH_2—$). In some non-limiting embodiments, the linking group can be a methylene group ($—CH_2—$), an ethylene group ($—CH_2CH_2—$), or a propylene group ($—CH_2CH_2CH_2—$); or alternatively, an ethylene group ($—CH_2CH_2—$), or a propylene group ($—CH_2CH_2CH_2—$). In yet other embodiments, the linking group can be a methylene group; alternatively, an ethylene group; or alternatively, a propylene group.

In embodiments, the primary amine comprising a metal salt complexing group can be 1-(2-aminoethyl)pyrrolidine, 2-(2-aminoethyl)piperdine, 2-(2-aminoethyl)pyrrolidine, N,N-dimethyl-ethylenediamine, N,N-diethylethylenediamine, N,N-diphenylethylenediamine, 2-(aminomethyl)pyridine, 2-(2-aminoethyl)pyridine, 2-(diphenylphosphino)ethylamine, 3-(diphenylphosphino)propylamine, 2-(2-aminoethyl)furan, 2-(aminomethyl)furan, 2-(2-aminoethyl)thiophene, 2-(aminomethyl)thiophene, 2-aminoethyl-(4-chlorophenyl)sulfide, 2-phenoxyethylamine, 2-methoxyethylamine, 2-ethoxyethylamine, 2-isopropxyethylamine, and 1-(2-aminoethyl)piperidine. In some embodiments, the primary amine comprising a metal salt complexing group can be N,N-dimethylethylenediamine, N,N-diethylethylenediamine, N,N-diphenylethylenediamine, 2-(aminomethyl)pyridine, 2-(2-aminoethyl)pyridine, 2-(diphenylphosphino)ethylamine, 3-(diphenyl-phosphino) propylamine, 2-aminoethyl-(4-chlorophenyl)sulfide, 2-phenoxyethylamine, 2-methoxyethylamine, 2-ethoxyethylamine, 2-and isopropoxyethylamine. In yet other embodiments, the primary amine comprising a metal salt complexing group can be N,N-dimethylethylenediamine or N,N-diethylethylenediamine; alternatively, N,N-diphenylethylenediamine, 2-(diphenylphosphino)ethylamine, 3-(diphenylphosphino)propylamine; alternatively, 2-(aminomethyl)pyridine, 2-(2-aminoethyl)pyridine; alternatively, 2-aminoethyl-(4-chlorophenyl)sulfide; or alternatively, 2-phenoxyethylamine, 2-methoxyethylamine, 2-ethoxyethylamine, and 2-isopropxyethylamine. In further embodiments, the primary amine comprising a metal salt complexing group can be N,N-dimethylethylenediamine; alternatively, N,N-diethylethylenediamine; alternatively, N,N-diphenylethylenediamine; alternatively, 2-(diphenylphosphino)ethylamine; alternatively, 3-(diphenylphosphino)propylamine; alternatively, 2-(aminomethyl)pyridine; alternatively, 2-(2-aminoethyl)pyridine; or alternatively, 2-aminoethyl-(4-chlorophenyl)sulfide.

In some embodiments, the metal salt complexing group can have any Structure indicated in Table 2. In some embodiments, the metal salt complexing group can have Structure 1c or Structure 2c. In other embodiments, the metal salt complexing group can have Structure 3c or Structure 4c; alternatively, Structure 5c or Structure 6c; alternatively, Structure 8c or Structure 9c; alternatively,

TABLE 2

| Example Metal salt complexing Groups |
|---|
| $—OR^{c1}$ |
| Structure 1c |
| $—SR^{c1}$ |
| Structure 2c |
| $—NR^{c5}R^{c6}$ |
| Structure 3c |
| $—PR^{c5}R^{c6}$ |
| Structure 4c |
| 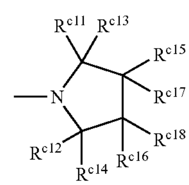 |
| Structure 5c |
| 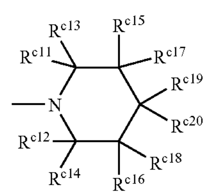 |
| Structure 6c |
| 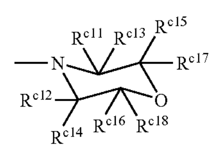 |
| Structure 7c |
| 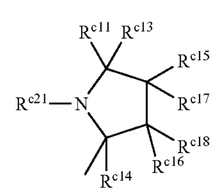 |
| Structure 8c |
| 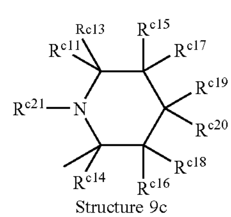 |
| Structure 9c |

TABLE 2-continued

Example Metal salt complexing Groups

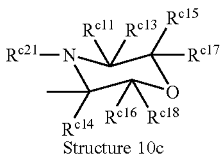
Structure 10c

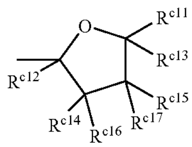
Structure 11c

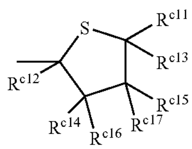
Structure 12c

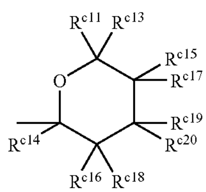
Structure 13c

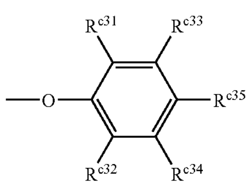
Structure 14c

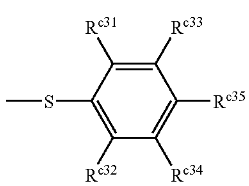
Structure 15c

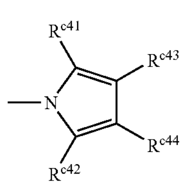
Structure 16c

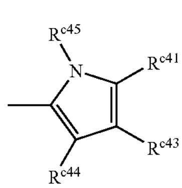
Structure 17c

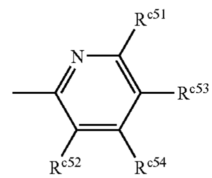
Structure 18c

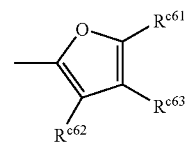
Structure 19c

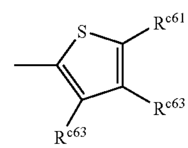
Structure 20c

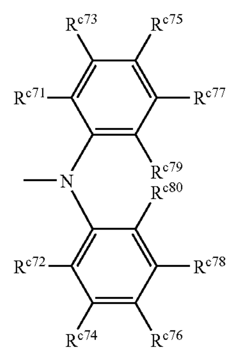
Structure 21c

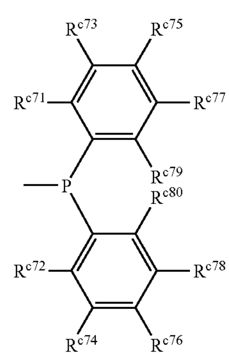
Structure 22c

Structure 11c or Structure 12c; alternatively, Structure 14c or Structure 15c; alternatively, Structure 19c or Structure 20c; or alternatively, Structure 21c or Structure 22c. In yet other embodiments, the metal salt complexing group can have Structure 3c; alternatively, Structure 4c; alternatively, Structure 7c; Structure 10c; alternatively, Structure 13c; alternatively, Structure 16c; alternatively, Structure 17c; alternatively, Structure 18; alternatively, Structure 21c; or alternatively, Structure 22c.

Within the structures of Table 2, $R^{c1}$, $R^{c5}$, $R^{c6}$, $R^{c11}$ to/through $R^{c21}$, $R^{c31}$ to/through $R^{c35}$, $R^{c41}$ to/through $R^{c45}$, $R^{c51}$ to/through $R^{c54}$, $R^{c61}$ to/through $R^{c63}$, $R^{c71}$ to/through $R^{c80}$ can each independently be hydrogen, an organyl group consisting of inert functional groups, a hydrocarbyl group, or inert functional groups. In embodiments, $R^{c1}$, $R^{c5}$, $R^{c6}$, $R^{c11}$ to/through $R^{c20}$, $R^{c31}$ to/through $R^{c35}$, $R^{c41}$ to/through $R^{c44}$, $R^{c51}$ to/through $R^{c54}$, $R^{c61}$ to/through $R^{c63}$, $R^{c71}$ to/through $R^{c80}$ of each Structure in Table 2 can independently be hydrogen, an organyl group consisting of inert functional groups, a hydrocarbyl group, or an inert functional group and $R^{c21}$ and $R^{c45}$ can be a hydrocarbyl group. In some embodiments, $R^{c1}$, $R^{c5}$, $R^{c6}$, $R^{c11}$ to/through $R^{c21}$, $R^{c31}$ to/through $R^{c35}$, $R^{c41}$ to/through $R^{c45}$, $R^{c51}$ to/through $R^{c54}$, $R^{c61}$ to/through $R^{c63}$, $R^{c71}$ to/through $R^{c80}$ of each Structure of Table 2 an independently be hydrogen, a $C_1$ to $C_{10}$ organyl group, a $C_1$ to $C_{10}$ organyl group consisting of inert functional groups, a $C_1$ to $C_{10}$ hydrocarbyl group, a $C_1$ to $C_5$ organyl group, a $C_1$ to $C_5$ organyl group consisting of inert functional groups, a $C_1$ to $C_5$ hydrocarbyl group or an inert functional group. The organyl groups, organyl groups consisting of inert functional groups, hydrocarbyl groups, and inert functional groups are generally described within the description of the metal complexing group descriptions and can have any embodiment as described therein.

In some embodiments, the linking group can have any structure indicated in Table 3. Within the Structure of Table 3, the undesignated valancies are the points of attachment for the —$NH_2$ group and the metal salt complexing group; each $R^L$ can independently be hydrogen, a methyl group, or an ethyl group; and m can be an integer ranging from 1 to 5. In further embodiments, m can be an integer ranging from 1 to 3; alternatively, m can be 2 or 3; alternatively, m can be 1; alternatively, m can be 2; or alternatively, m can be 3.

TABLE 3

| Example Linking Groups |
| --- |
| $—(CR^LR^L)_m—$<br>Structure 1L |
| $—(CH_2)_m—$<br>Structure 2L |
| $—(CH_2)—$<br>Structure 3L |
| $—(CH_2CH_2)—$<br>Structure 4L |
| 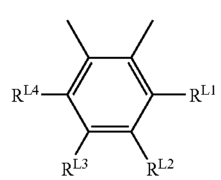<br>Structure 5L |

In embodiments, the linking group can have Structure 1L, Structure 2L, Structure 3L, Structure 4L or Structure 5L. In some embodiments, the linking group can have Structure 4L or Structure 5L. In other embodiments, the linking group can have Structure 2L; alternatively, Structure 3L; alternatively, Structure 4L; or alternatively, Structure 5L.

α-Acylimine Compounds

The α-acylimine compounds can be described using any one of several descriptions. While the α-acylimine compound descriptions may be indicated by labels such as first description, second description, etc., these labels do not indicate a particular preference to the description of the α-acylimine compounds.

In a first description, the α-acylimine compound can be minimally described as a compound comprising an α-acylimine group. In further embodiments, the α-acylimine compound can be described as a compound comprising 1) an α-acylimine group and 2) an α-acylimine nitrogen group. In this first α-acylimine compound description, the α-acylimine group can be further described as being derived from an α-diacyl compound. Thus, alternatively, the α-acylimine compound can be described as compound comprising 1) an α-acylimine group derived from an α-diacyl compound and 2) an α-acylimine nitrogen group; or alternatively, a compound consisting of 1) an α-acylimine group derived from an α-diacyl compound and 2) an α-acylimine nitrogen group.

Within the α-acylimine compound, the α-acylimine group's nitrogen atom is derived from the primary amine's —$NH_2$ group and the α-acylimine compound's nitrogen group is derived from the remainder of the primary amine. Thus, the α-acylimine nitrogen group can have any of the embodiments as the primary amine (with the absence of the —$NH_2$ group) as described herein. Therefore, the organyl group, metal salt complexing group, linking group, organyl group consisting of inert functional groups, and hydrocarbyl groups of the primary amine embodiments described herein are generally applicable to the description of the α-acylimine compound's nitrogen group with the proviso that the linking group links the metal salt complexing group to the imine nitrogen atom of the α-acylimine group instead of the —$NH_2$ group of the primary amine. Thus, in embodiments, the α-acylimine nitrogen group can comprise an organyl group; alternatively, comprise a metal salt complexing group; alternatively, comprise a metal salt complexing group and a linking group linking the metal salt complexing group to the α-acylimine nitrogen group nitrogen atom; alternatively, comprise an organyl group consisting of inert functional groups; alternatively, comprise a hydrocarbyl group; alternatively, consist of an organyl group; alternatively, consist of a metal salt complexing group and a linking group linking the metal salt complexing group to the α-acylimine nitrogen group nitrogen atom; alternatively, consist of an organyl group consisting of inert functional groups; or alternatively, consist of a hydrocarbyl group. Additionally, as the α-acylimine group and the α-acylimine nitrogen group are derived from separate and independent elements, the α-diacyl compound and the primary amine, respectively, the α-acylimine compound can be further described using any combination of the α-diacyl compound element described herein and the elements of the primary amine as described herein.

In a second description, the α-acylimine compound can be described as an α-acylimine compound product of contacting an α-diacyl compound with a primary amine. Within this second α-acylimine compound description, as in the synthesis of the α-acylimine compound, the α-diacyl compound and the primary amine are separate and independent elements. Thus, in the second α-acylimine compound description, the α-acylimine compound can be further described using any combination of the α-diacyl compound element described herein and the primary amine element as described herein. As non-limiting examples, the α-acylimine compound can be the α-acylimine compound product of contacting an α-diacyl compound with a primary amine comprising an —$NH_2$ group and an organyl group; alternatively, contacting an α-diacyl compound with a primary amine comprising an —$NH_2$ group and a metal salt complexing group; alternatively, contacting an α-diacyl compound with a primary amine comprising an —$NH_2$ group, a metal salt complexing group, and a linking group linking the metal salt complexing group to the —$NH_2$ group; alternatively, contacting an α-diacyl compound with a primary amine comprising an —$NH_2$ group and an organyl group consisting of inert functional groups; alternatively, contacting an α-diacyl compound with a primary amine comprising an —$NH_2$ group and a hydrocarbyl group; alternatively, contacting an α-diacyl compound with a primary amine consisting of an —$NH_2$ group and an organyl group; alternatively, contacting an α-diacyl compound with a primary amines consisting of an —$NH_2$ group, a metal salt complexing group, and a linking group linking the metal salt complexing group to the —$NH_2$ group; alternatively, contacting an α-diacyl compound with a primary amine consisting of an —$NH_2$ group and an organyl group consisting of inert functional groups; or alternatively, contacting an α-diacyl compound with a primary amine consisting of an —$NH_2$ group and a hydrocarbyl group. The α-acylimine compound can be further described using any combination of the α-diacyl compound element described herein and the primary amine element as described herein.

In a third description, the α-acylimine compounds can be described as an α-acylimine compound product produced by any process as described herein and can be further described using any embodiments of the processes as described herein.

In a fourth description, the α-acylimine compound can be described as having any structure as indicated in Table 4. In some embodiments, the α-acylimine compound can have Structure 1b or Structure 27b; alternatively, Structure 2b or Structure 28b; alternatively, Structure 3b, Structure 4b, Structure 5b, Structure 29b, Structure 30b, or Structure 31b; alternatively, Structure 6b or Structure 32b; alternatively, Structure 7b, Structure 8b, mixtures of Structure 9b and Structure 10b, Structure 33b, Structure 34b, or mixtures of Structure 35b and Structure 36b; alternatively, Structure 11b, Structure 12b, Structure 13b, Structure 37b, Structure 38b, or Structure 39b; or alternatively, Structure 11b or Structure 37b. In other embodiments, the α-acylimine compound can have Structure 27b; alternatively, Structure 28b; alternatively, Structure 29b, Structure 30b, or Structure 31b; alternatively, Structure 32b; alternatively, Structure 33b, Structure 34b, or mixtures of Structure 35b and Structure 36b; alternatively, Structure 37b, Structure 38b, or Structure 39b; or alternatively, Structure 37b. In yet other embodiments, the α-acylimine compound can have Structure 14b; alternatively, Structure 15b; alternatively, Structure 16b, Structure 17b, or Structure 18b; alternatively, Structure 19b; alternatively, Structure 20b, Structure 21b, or mixtures of Structure 22b and Structure 23b; alternatively, Structure 24b, Structure 25b, or Structure 26b; or alternatively, Structure 24b.

TABLE 4

| Example α-Acylimine Compounds |
|---|
| 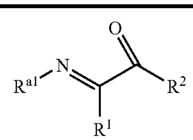 Structure 1b |

TABLE 4-continued

| Example α-Acylimine Compounds |
|---|
| 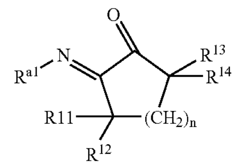 Structure 2b |
| 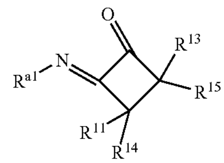 Structure 3b |
| 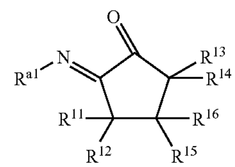 Structure 4b |
| 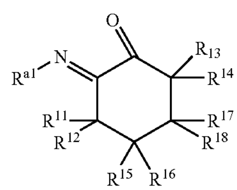 Structure 5b |
| 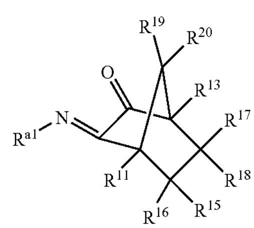 Structure 6b |
| 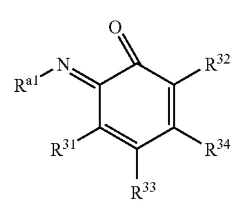 Structure 7b |
| 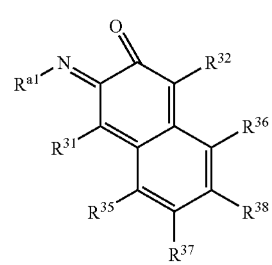 Structure 8b |

TABLE 4-continued
| Example α-Acylimine Compounds |
|---|
| 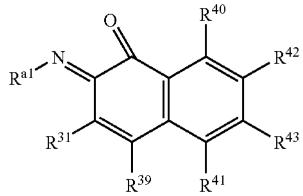 Structure 9b |
| 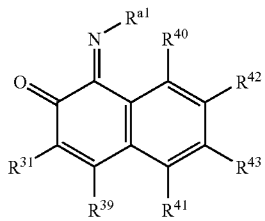 Structure 10b |
| 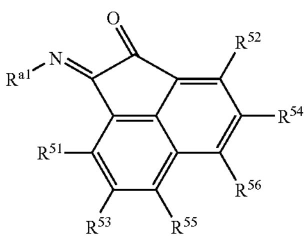 Structure 11b |
| 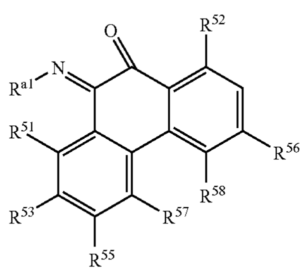 Structure 12b |
| 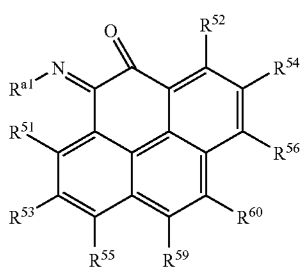 Structure 13b |
| 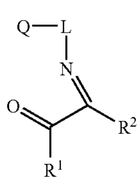 Structure 14b |
TABLE 4-continued
| Example α-Acylimine Compounds |
|---|
| 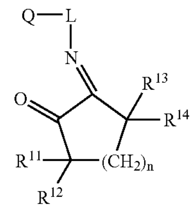 Structure 15b |
| 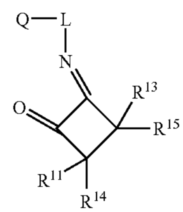 Structure 16b |
| 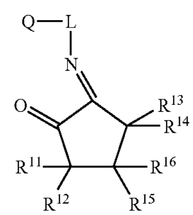 Structure 17b |
| 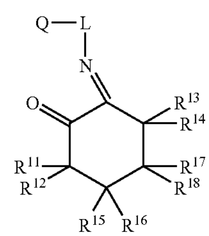 Structure 18b |
| 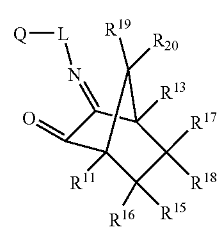 Structure 19b |
| 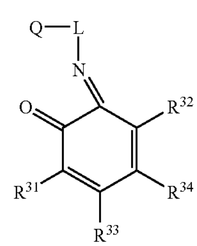 Structure 20b |

TABLE 4-continued
| Example α-Acylimine Compounds |
| --- |
| 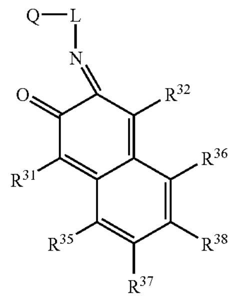<br>Structure 21b |
| 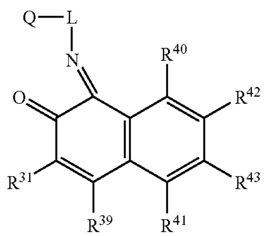<br>Structure 22b |
| 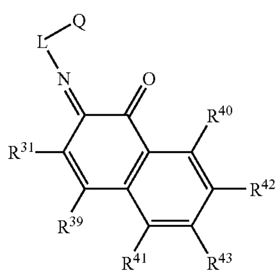<br>Structure 23b |
| 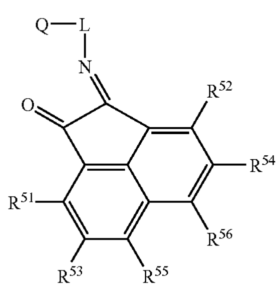<br>Structure 24b |
| 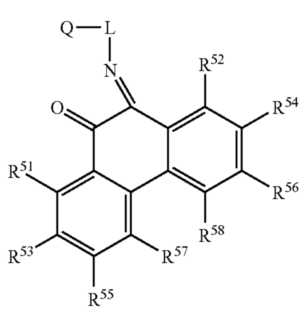<br>Structure 25b |
TABLE 4-continued
| Example α-Acylimine Compounds |
| --- |
| 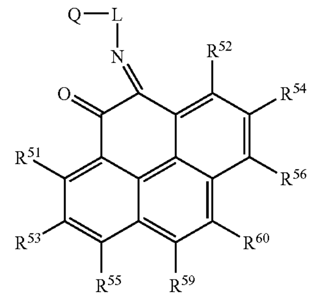<br>Structure 26b |
| 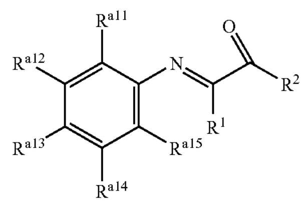<br>Structure 27b |
| 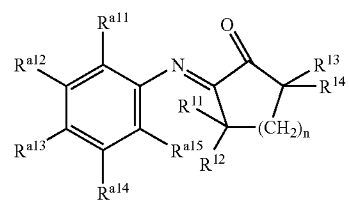<br>Structure 28b |
| 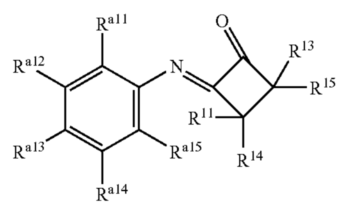<br>Structure 29b |
| 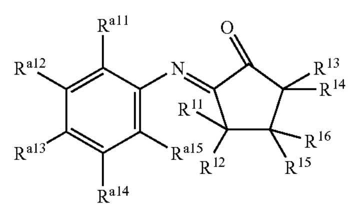<br>Structure 30b |
| 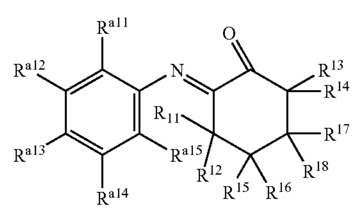<br>Structure 31b |

TABLE 4-continued

Example α-Acylimine Compounds

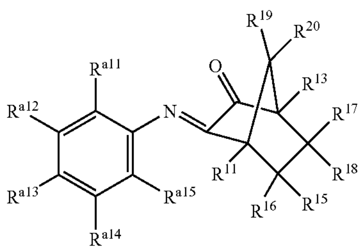
Structure 32b

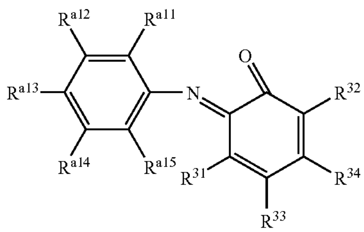
Structure 33b

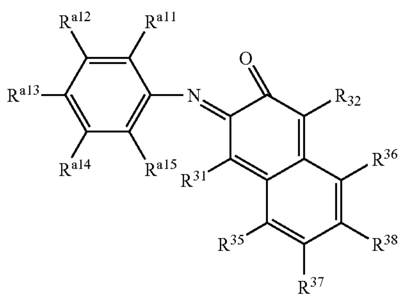
Structure 34b

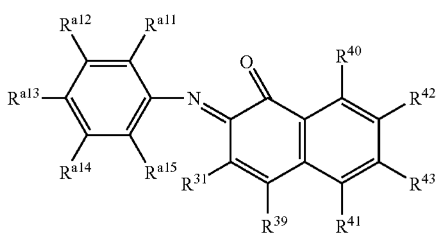
Structure 35b

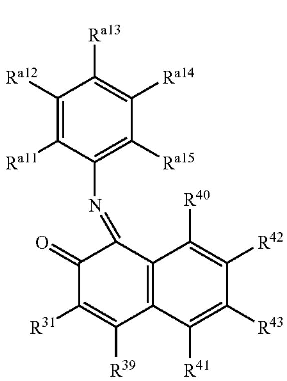
Structure 36b

TABLE 4-continued

Example α-Acylimine Compounds

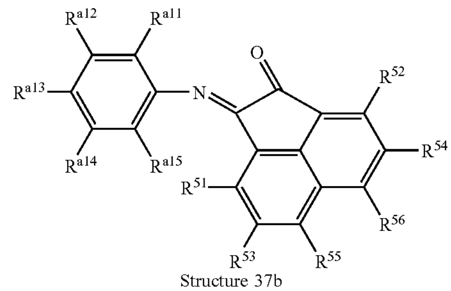
Structure 37b

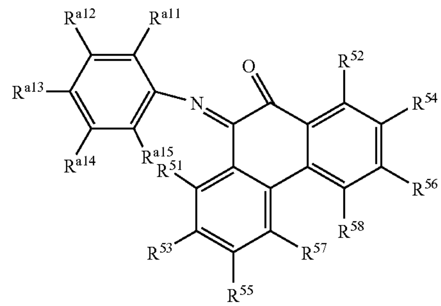
Structure 38b

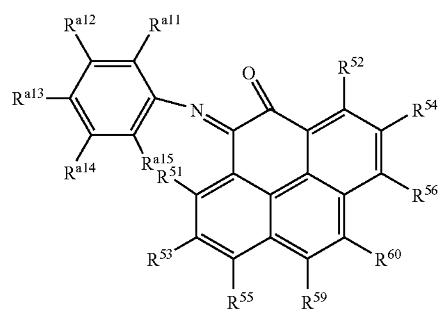
Structure 39b

The α-acylimine compounds of Table 4 can be prepared utilizing various methods as described herein. Depending upon the α-acylimine compound preparation method, the α-diacyl compound and the primary amine can be separate and independent elements in the preparation of the α-acylimine compound. Therefore, the $R^x$s of α-diacyl compound having Structures 1-12 (Table 1), the $R^{ax}$s of the primary amines having Structures 1a-4a, the linking groups 1L-5L (Table 3) of the primary amine having Structure 5a, and the metal salt complexing group $R^{cx}$s having Structures 1c-22c(Table 2) of the primary amine having Structure 5a are separate and independent elements of the α-acylimine compounds of Table 4. Thus, the α-acylimine compounds of Table 4 can be further described using any combination of the $R^x$s of α-diacyl compound having Structures 1-12 (Table 1) as described herein, the $R^{ax}$s of the primary amines having Structures 1a-4a as described herein, the linking groups 1L-5L (Table 3) of the primary amine having Structure 5a as described herein, and the metal salt complexing group $R^{cx}$s having Structures 1c-22c (Table 2) of the primary amine having Structure 5a as described herein.

Metal Salts

The metal salts, $M—X_p$, employed in forming the α-acylimine or α-diimine metal complexes can be any salt comprising any metal atom. Suitable metal salts can comprise any metal from groups IVB through VIII of the CAS version of the periodic table of elements. In some embodiments, the metal salt can be titanium, zirconium, hafnium, vanadium, niobium, tantalum, chromium, manganese, iron, cobalt, nickel, palladium, platinum, or mixtures thereof. In other embodiments, the metal salt can comprise chromium, iron, cobalt, nickel, palladium, or mixtures thereof; alternatively, chromium, iron, cobalt, or mixtures thereof; alternatively, iron, cobalt, or mixtures thereof; alternatively, nickel, palladium, or mixtures thereof; alternatively, chromium; alternatively, iron; alternatively, cobalt; alternatively, nickel; or alternatively, palladium.

In some embodiments, the metal salt is dicoordinating; can complex with two complexing atoms (e.g. the two imine nitrogen atoms of an α-diimine compound or the oxygen atom of the acyl group and the nitrogen atom of the imine group of an α-acylimine compound). In other embodiments, the metal salt can be tricoordinating; can complex with three complexing atoms (e.g. the two imine nitrogen atoms and heteroatom of the metal salt complexing group of an α-diimine compound). Typically, dicoordinating metal salts are utilized with bidentate α-diimine compounds and tricoordinating metal salts are utilized with tridentate α-diimine compounds.

In some embodiments wherein the α-diimine compound portion of the α-diimine metal complex is tridentate (e.g. the α-diimine compound portion of the α-diimine metal complex comprises an α-diimine group and a metal salt complexing group), the metal salt can comprise chromium, iron, cobalt, or mixtures thereof; alternatively, iron, cobalt, or mixtures thereof; alternatively, iron; or alternatively, cobalt. In some embodiments wherein the α-diimine compound portion of the α-diimine metal complex is bidentate (e.g. the α-diimine compound portion of the α-diumine metal complex comprises an α-diimine group and does not contain a metal salt complexing group), the metal salt can comprise nickel, palladium, or mixtures thereof; alternatively, nickel, or alternatively, palladium.

The anion X, of the metal salt can be any anion. In some embodiments, the anion X can be a halide, carboxylate, acetonate, alkoxide, phenoxide, nitrate, sulfate, phosphate, or chlorate. In some embodiments, the anion, X, is a halide or acetonate. In embodiments, the halide can be fluorine, chlorine, bromine, iodine, or combinations thereof; alternatively, chlorine, bromine, iodine, or combinations thereof; alternatively, chlorine; alternatively, bromine, or alternatively, iodine. In carboxylate, acetonate, alkoxide or phenoxide embodiments, the carboxylate, acetonate, alkoxide, or phenoxide can be any $C_1$ to $C_{20}$ carboxylate, acetonate, alkoxide, or phenoxide; or alternatively, any $C_1$ to $C_{10}$ carboxylate, acetonate, alkoxide, or phenoxide. In some embodiments, the anion, X, can be a $C_1$ to $C_{10}$ acetonate; alternatively, a $C_1$ to $C_{10}$ carboxylate; alternatively, a $C_1$ to $C_{10}$ alkoxide; or alternatively, a $C_1$ to $C_{10}$ phenoxide. In other embodiments, the anion X, can be acetylacetonate; alternatively, acetate; alternatively, 2-ethylhexanoate; or alternatively, triflate.

Generally, the number, p, of anions, X, is such that the total number of negative charges on the total number of X anions equals the oxidation state of M. In some embodiments, p is 1, 2, or 3, and the total number of negative charges on X is equal to the oxidation state of M. In other embodiments, the total number of anions, p, is 2; or alternatively, 3.

In embodiments, tricoordinating metal salts can be chromium(II) chloride, chromium(III) chloride, chromium(II) fluoride, chromium(III) fluoride, chromium(II) bromide, chromium(III) bromide, chromium(II) iodide, chromium (III) iodide, chromium(II) acetate, chromium(III) acetate, chromium(III) acetylacetonate, chromium(II) 2-ethylhexanoate, chromium(II) triflate, chromium(III) nitrate, iron(II) chloride, iron(III) chloride, iron(II) fluoride, iron(III) fluoride, iron(II) bromide, iron(III) bromide, iron(II) iodide, iron(III) iodide, iron(II) acetate, iron(III) acetate, iron(II) acetylacetonate, iron(III) acetylacetonate, iron(II) 2-ethylhexanoate, iron(II) triflate, iron(III) nitrate, cobalt(II) chloride, cobalt(III) chloride, cobalt(II) fluoride, cobalt(III) fluoride, cobalt(II) bromide, cobalt(III) bromide, cobalt(II) iodide, cobalt(III) iodide, cobalt(II) acetate, cobalt(III) acetate, cobalt(II) acetylacetonate, cobalt(II) benzoylacetonate, cobalt(III) acetylacetonate, cobalt(II) 2-ethylhexanoate, cobalt(II) triflate, cobalt(III) nitrate, vanadium(III) chloride, vanadium(II) chloride, vanadium(III) chloride tetrahydrofuran complex, vanadium(III) iodide, manganese(II) acetate, manganese(II) acetylacetonate, manganese(II) bromide, manganese(II) chloride, manganese(II) fluoride, manganese(III) fluoride, or manganese(II) iodide. In some embodiments, the tricoordinating metal salt can be chromium(II) chloride, chromium(III) chloride, chromium(II) acetate, chromium (III) acetate, chromium(III) acetylacetonate, iron(II) chloride, iron(III) chloride, iron(II) acetate, iron (III) acetate, iron(II) acetylacetonate, iron(III) acetylacetonate, cobalt(II) chloride, cobalt(III) chloride, cobalt(II) acetate, cobalt (III) acetate, or cobalt(II) acetylacetonate. In other embodiments, the tricoordinating metal salt metal salt can be chromium(II) chloride, chromium(III) acetylacetonate, iron(II) chloride, iron(II) acetylacetonate, iron(III) acetylacetonate, cobalt(II) chloride, cobalt(II) acetylacetonate. In other embodiments, the tricoordinating metal salt can be chromium(II) chloride; alternatively, chromium(III) acetylacetonate; alternatively, iron(II) chloride; alternatively, iron(II) acetylacetonate; alternatively, cobalt(II) chloride; or alternatively, cobalt(II) acetylacetonate.

In embodiments, dicoordinating metal salts can be nickel (II) chloride, nickel(II) fluoride, nickel(II) bromide, nickel (II) iodide, nickel(II) acetate, nickel(II) acetylacetonate, nickel(II) benzoylacetonate, nickel(II) 2-ethylhexanoate, nickel(II) triflate, nickel(II) nitrate, palladium(II) chloride, palladium(II) fluoride, palladium(II) bromide, palladium(II) iodide, palladium(II) acetate, palladium(II) acetylacetonate, or palladium(II) nitrate. In some embodiments, the dicoordinating metal salt can be nickel(II) chloride, nickel(II) acetylacetonate, palladium(II) chloride, or palladium(II) acetylacetonate. In other embodiments, the dicoordinating metal salt can be alternatively, nickel(II) chloride; alternatively, nickel(II) acetylacetonate; alternatively, palladium(II) chloride; or alternatively, or palladium(II) acetylacetonate.

α-Acylimine Metal Complexes

The α-acylimine metal complexes can be described using any one of several descriptions. While the α-acylimine metal complex descriptions may be indicated by labels such as first description, second description, etc., these labels do not indicate a particular preference to the description of the α-acylimine metal complexes.

In a first description, the α-acylimine metal complex can be described as a complex between an α-acylimine compound and a metal salt. While this α-acylimine metal complex description appears to imply a specific α-acylimine metal complex synthesis method, this is not the intent. The method of preparing the α-acylimine metal complex is independent of the method of describing the α-acylimine metal complex. Thus, while the α-acylimine metal complex can be described as a complex between an α-acylimine compound and a metal salt, the α-acylimine metal complex can be prepared by contacting an α-acylimine compound and a metal salt or any other method described herein. The α-acylimine compound and the metal salt are separate and independent elements. Thus, the α-acylimine metal complex can be further described using any combination of the α-acylimine compound element described herein and the metal salt element as described herein.

In a second description, the α-acylimine metal complex can be described as a product produced by any process described herein capable of producing the α-acylimine metal complex and can be further described using any embodiments of the processes described herein.

In a third description, the α-lacylimine metal complex can have any structure as indicated in Table 5. In some embodiments, the α-acylimine metal complex can have Structure 1d or Structure 27d; alternatively, Structure 2d or Structure 28d; alternatively, Structure 3d, Structure 4d, Structure 5d, Structure 29d, Structure 30d, or Structure 31d; alternatively, Structure 6d or Structure 32d; alternatively, Structure 7d, Structure 8d, mixtures of Structure 9d and Structure 10d, Structure 33d, Structure 34d, or mixtures of Structure 35d and Structure 36d; alternatively, Structure 11d, Structure 12d, Structure 13d, Structure 37d, Structure 38d, or Structure 39d; or alternatively, Structure 11d or Structure 37d. In other embodiments, the α-acylimine metal complex can have Structure 27d; alternatively, Structure 28d; alternatively, Structure 29d, Structure 30d, or Structure 31d; alternatively, Structure 32d; alternatively, Structure 33d, Structure 34d, or mixtures of Structure 35d and Structure 36d; alternatively, Structure 37d, Structure 38d, or Structure 39d; or alternatively, Structure 37d. In yet other embodiments, the α-acylimine metal complex can have Structure 14d; alternatively, Structure 15d; alternatively, Structure 16d, Structure 17d, or Structure 18d; alternatively, Structure 19d; alternatively, Structure 20d, Structure 21d, or mixtures of Structure 22d and Structure 23d; alternatively, Structure 24d, Structure 25d, or Structure 26d; or alternatively, Structure 24d.

TABLE 5

Example α-Acylimine Metal Complexes

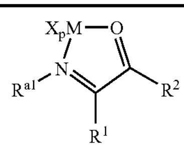
Structure 1d

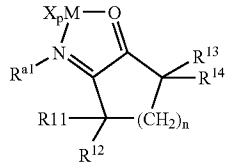
Structure 2d

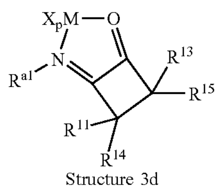
Structure 3d

TABLE 5-continued

Example α-Acylimine Metal Complexes

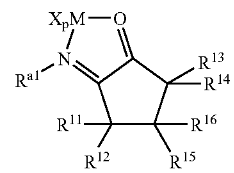
Structure 4d

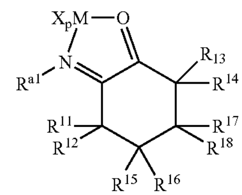
Structure 5d

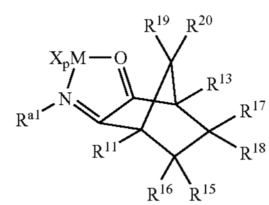
Structure 6d

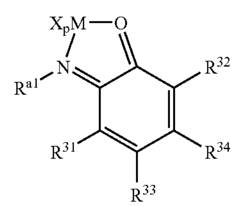
Structure 7d

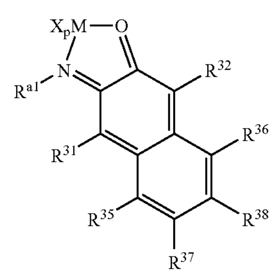
Structure 8d

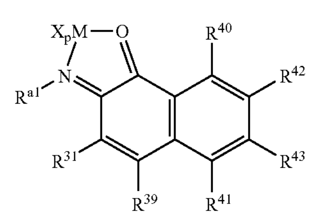
Structure 9d

TABLE 5-continued
Example α-Acylimine Metal Complexes
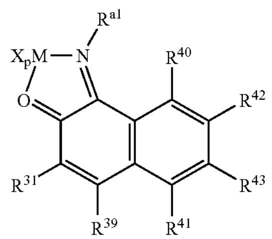
Structure 10d
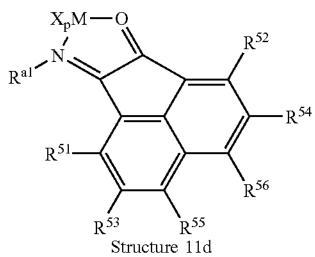
Structure 11d
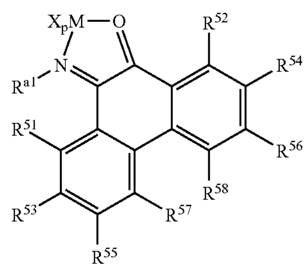
Structure 12d
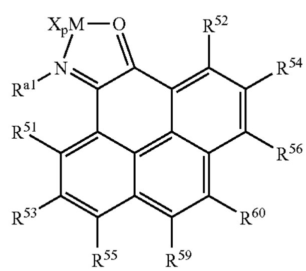
Structure 13d
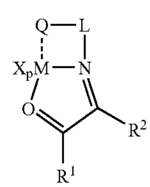
Structure 14d
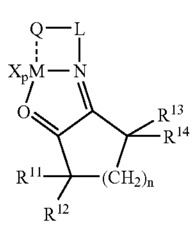
Structure 15d
TABLE 5-continued
Example α-Acylimine Metal Complexes
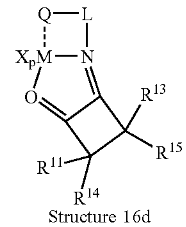
Structure 16d
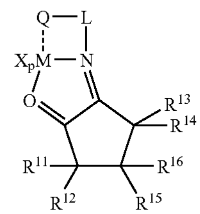
Structure 17d
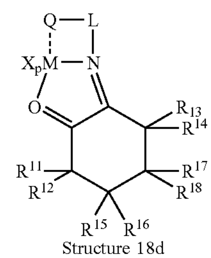
Structure 18d
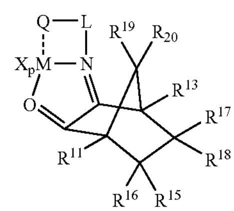
Structure 19d
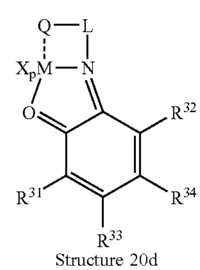
Structure 20d
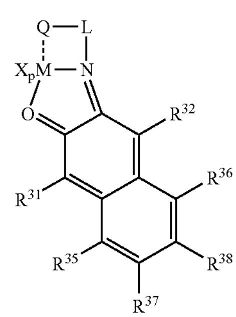
Structure 21d TABLE 5-continued
Example α-Acylimine Metal Complexes
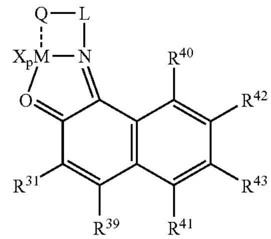
Structure 22d
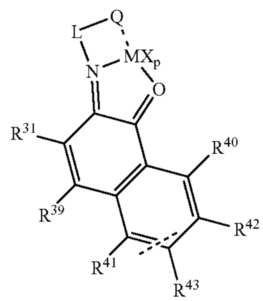
Structure 23d
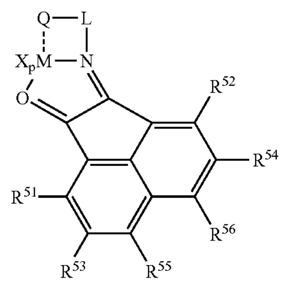
Structure 24d
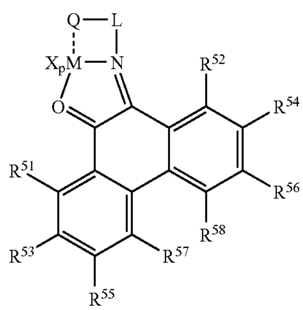
Structure 25d
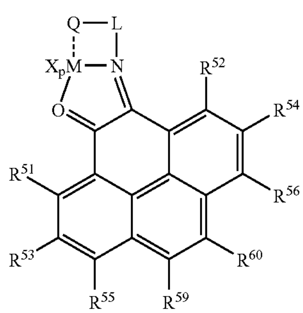
Structure 26d
TABLE 5-continued
Example α-Acylimine Metal Complexes
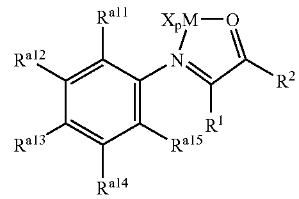
Structure 27d
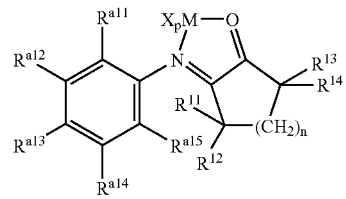
Structure 28d
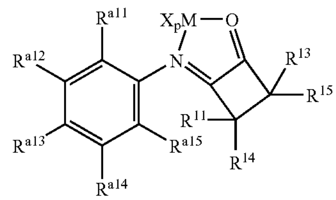
Structure 29d
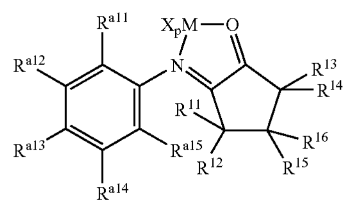
Structure 30d
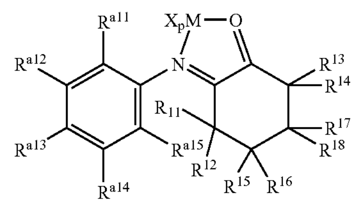
Structure 31d
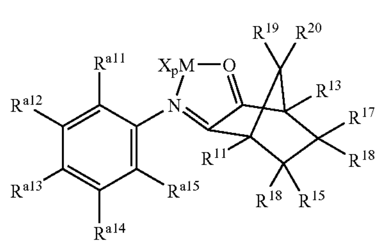
Structure 32d TABLE 5-continued Example α-Acylimine Metal Complexes

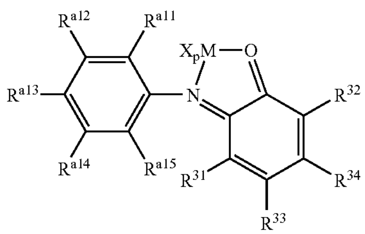

Structure 33d

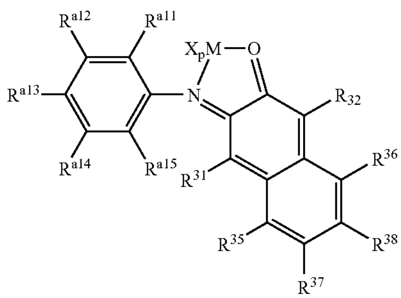

Structure 34d

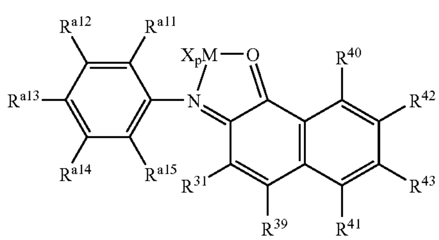

Structure 35d

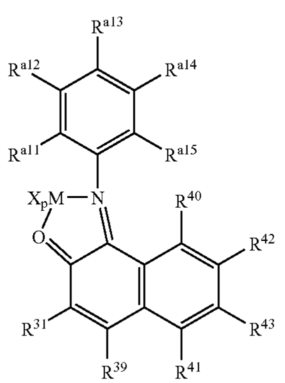

Structure 36d

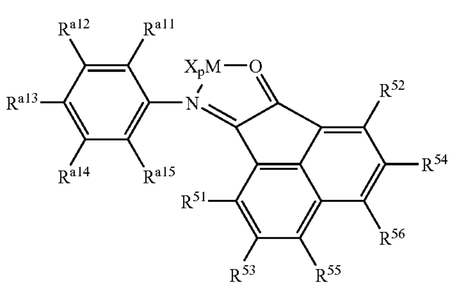

Structure 37d

TABLE 5-continued

Example α-Acylimine Metal Complexes

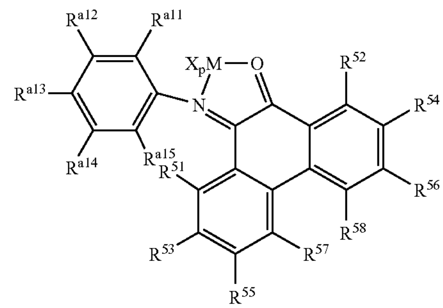

Structure 38d

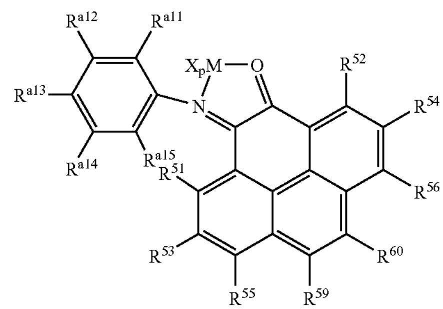

Structure 39d

The α-acylimine metal complexes of Table 5 can be prepared utilizing various methods as described herein. Depending upon the α-acylimine metal complex preparation method, the α-diacyl compound, the primary amine, the metal salt, and/or the α-acylimine compound can each be separate and independent elements in the preparation of the α-acylimine metal complex. Therefore, the $R^x$s of α-diacyl compounds having Structures 1-12 (Table 1), the metal salts, the $R^{ax}$s of the primary amines having. Structures 1a-4a, the linking groups 1L-5L (Table 3) of the primary amine having Structure 5a, and the metal salt complexing group $R^{cx}$s having Structures 1c-22c (Table 2) of the primary amine having Structure 5a are separate and independent elements of the α-acylimine metal complexes of Table 5. Thus, the α-acylimine metal complexes of Table 5 can be further described using any combination of the $R^x$s of α-diacyl compounds having Structures 1-12 (Table 1) as described herein, the metal salts as described herein, the $R^{ax}$s of the primary amines having Structures 1a-4a as described herein, the linking groups 1L-5L (Table 3) of the primary amine having Structure 5a as described herein, and the metal salt complexing group $R^{cx}$s having Structures 1c-22c (Table 2) of the primary amine having Structure 5a as described herein.

α-Diimine Metal Complexes

One aspect of the invention involves α-diimine metal complexes. The α-diimine metal complexes can be described using any one of several descriptions. While the α-diimine metal complex descriptions may be indicated by labels such as first description, second description, etc., these labels do not indicate a particular preference to the descriptions of the α-diimine metal complexes.

In a first description, the α-diimine metal complex can be described as a metal salt complexed to an α-diimine compound or as a complex between a diimine compound and a metal salt, the α-diimine compounds. While these particular α-diimine metal complex descriptions appear to imply a specific α-diimine metal complex preparation method, this is not the intent of α-diimine metal complex description. The method of preparing the α-diimine metal complex is independent of the method of describing the α-diimine metal complex. Thus, while the α-diimine metal complex may be described as a complex between an α-diimine compound and a metal salt, the α-diimine metal complex may be prepared by contacting an α-diimine compound and a metal salt, by contacting an α-acylimine compound, an amine and a metal salt, or any other method described herein. The α-diimine compounds and metal salts are separate and independent elements of the α-diimine metal complex. Thus within the first α-diimine metal complex description, the α-diimine metal complex can be described using any combination of α-diimine compound as described herein and the metal salt as described herein.

In embodiments, the α-diimine metal complex can be described as a dicoordinate metal salt complexed to a bidentate α-diimine compound. In some embodiments, the α-diimine metal complex can be described as a tricoordinate metal salt complexed to a tridentate α-diimine compound. It should be noted that while the later embodiment describes the α-diimine metal complex as a tricoordinate metal salt complexed to a tridentate α-diimine compound, this description does not necessarily imply that the three ligands of the tridentate α-diimine compound are complexed to the metal salt. For example, in example 7 a tricoordinate metal salt is complexed to a tridentate α-diimine compound wherein the metal salt complexing group is not complexed to the metal salt and can be utilized within other aspects of the invention as described herein.

In a second description, the α-diimine metal complex can be described as a product produced by any process described herein capable of producing the α-diimine metal complex and may be further described using any embodiments of the processes described herein.

In a third description, the α-diimine metal complex can be described as having any structure as indicated in Table 6. In embodiments, the α-diimine metal complex can have Structure 1e; alternatively, Structure 2e; alternatively, Structure 3e, Structure 4e, or Structure 5e; alternatively, Structure 6e; alternatively, Structure 7e, Structure 8e, or mixtures of Structure 9e and Structure 10e; alternatively, Structure 11e, Structure 12e, or Structure 13e; or alternatively, Structure 11e. In some embodiments, $R^{a1}$ and $R^{a1'}$ of Structures 1e-13e are different (not identical). In some embodiments, $R^{a1}$ of Structures 1e to/through 13e can have Structure 1 g (derived from a primary amine having Structure 3a).

Structure 1g

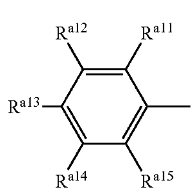

In other embodiments, $R^{a1'}$ of Structures 1e to/through 13e can have Structure 2 g (derived from a primary amine having Structure 4a).

Structure 2g

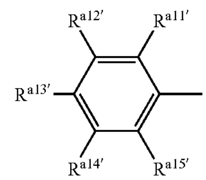

In other embodiments, $R^{a1}$ of Structures 1e to/through 13e can have Structure 1 g and $R^{a1'}$ of Structure 1e to/through 13e can have Structure 2 g. In some embodiments, wherein $R^{a1}$ and $R^{a1'}$ of Structures 1e to/through 13e can have Structure 1 g and Structure 2 g, respectively, wherein Structure 1 g and Structure 2 g are different (not identical).

In some embodiments, the α-diimine metal complex can have Structure 14e or Structure 27e; alternatively, Structure 15e or Structure 28e; alternatively, Structure 16e, Structure 17e, Structure 18e, Structure 29e, Structure 30e, or Structure 31e; alternatively, Structure 19e or Structure 32e; alternatively, Structure 20e, Structure 21e, mixtures of Structure 22e and Structure 23e, Structure 33e, Structure 34e, or mixtures of Structure 35e and Structure 36e; alternatively, Structure 24e, Structure 25e, Structure 26e, Structure 37e, Structure 38e, or Structure 39e; or alternatively, Structure 24e or Structure 37e. In other embodiments, the α-acylimine compound can have Structure 14e; alternatively, Structure 15e; alternatively, Structure 16e, Structure 17e, or Structure 18e; alternatively, Structure 19e; alternatively, Structure 20e, Structure 21e, or mixtures of Structure 22e and Structure 23e; alternatively, Structure 24e, Structure 25e, or Structure 26e; or alternatively, Structure 24e. In yet other embodiments, the α-acylimine compound can have Structure 27e; alternatively, Structure 28e; alternatively, Structure 29e, Structure 30e, or Structure 31e; alternatively, Structure 32e; alternatively, Structure 33e, Structure 34e, or mixtures of Structure 35e and Structure 36e; alternatively, Structure 37e, Structure 38e, or Structure 39e; or alternatively, Structure 37e.

TABLE 6

| Example α-Diimine Metal Complexes |
| --- |
| 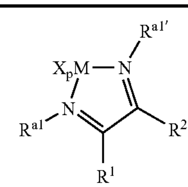 Structure 1e |
| 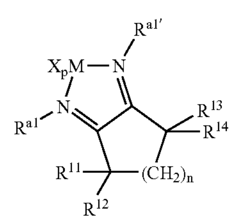 Structure 2e |

TABLE 6-continued
Example α-Diimine Metal Complexes
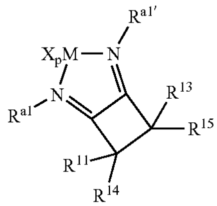
Structure 3e
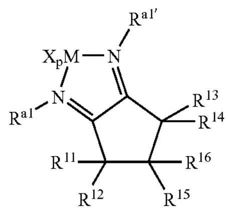
Structure 4e
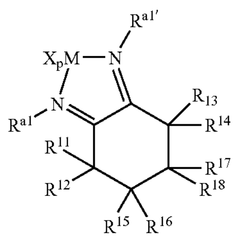
Structure 5e
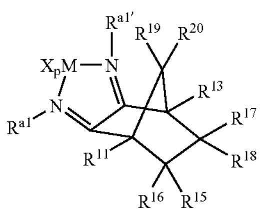
Structure 6e
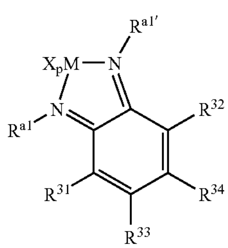
Structure 7e
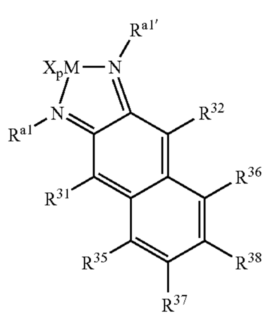
Structure 8e
TABLE 6-continued
Example α-Diimine Metal Complexes
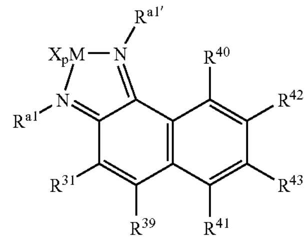
Structure 9e
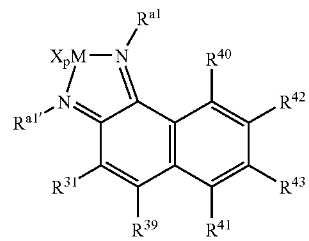
Structure 10e
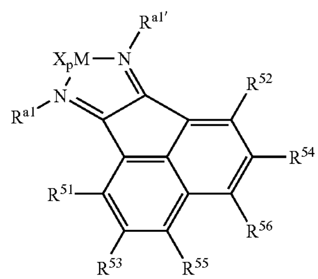
Structure 11e
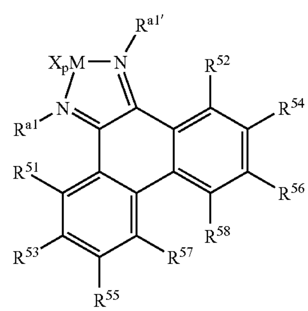
Structure 12e
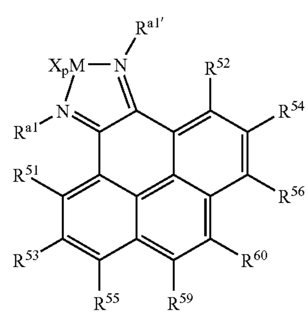
Structure 13e TABLE 6-continued
Example α-Diimine Metal Complexes
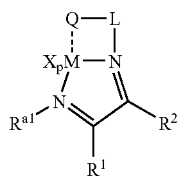
Structure 14e
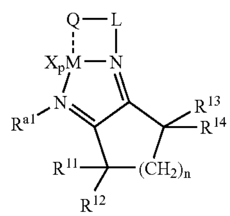
Structure 15e
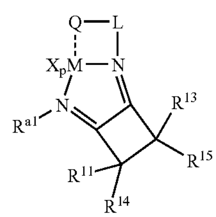
Structure 16e
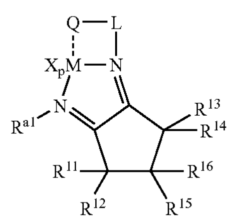
Structure 17e
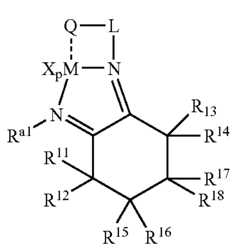
Structure 18e
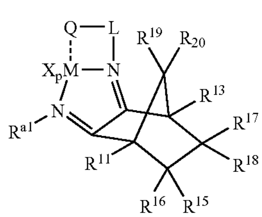
Structure 19e
TABLE 6-continued
Example α-Diimine Metal Complexes
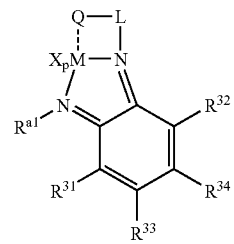
Structure 20e
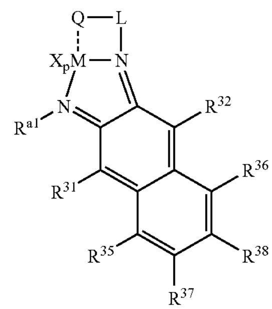
Structure 21e
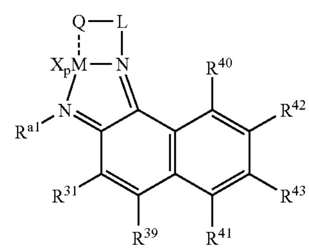
Structure 22e
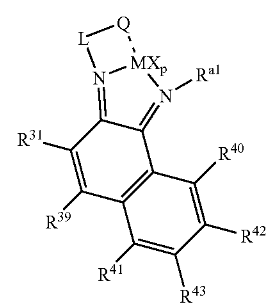
Structure 23e
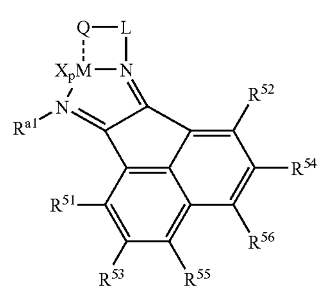
Structure 24e TABLE 6-continued
Example α-Diimine Metal Complexes
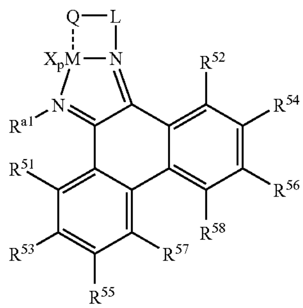
Structure 25e
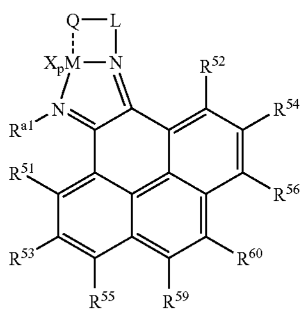
Structure 26e
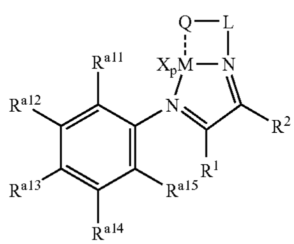
Structure 27e
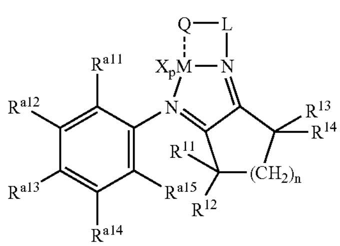
Structure 28e
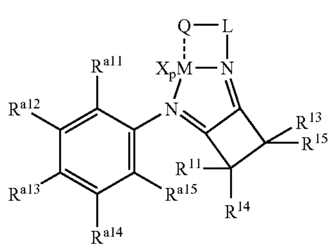
Structure 29e
TABLE 6-continued
Example α-Diimine Metal Complexes
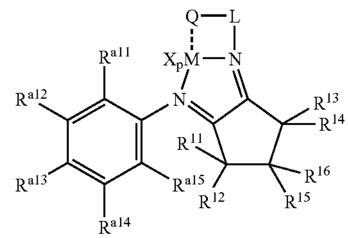
Structure 30e
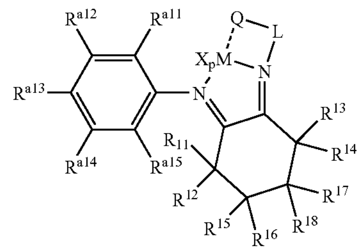
Structure 31e
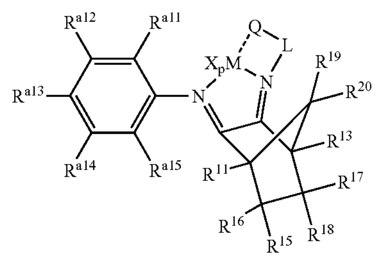
Structure 32e
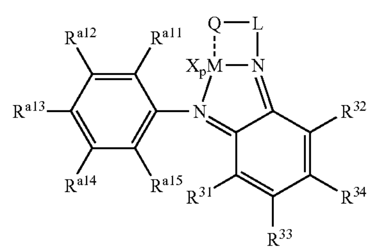
Structure 33e
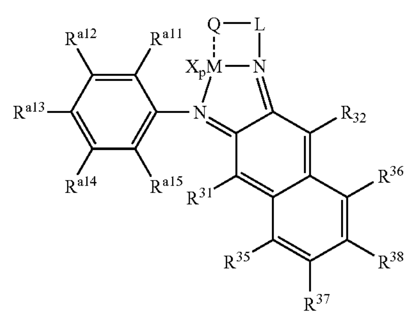
Structure 34e TABLE 6-continued

| Example α-Diimine Metal Complexes |
|---|
| 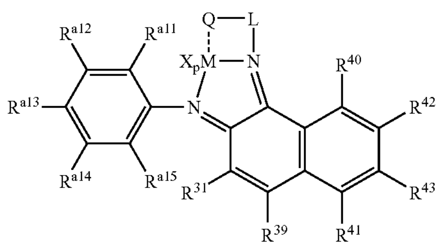 |
| Structure 35e |
| 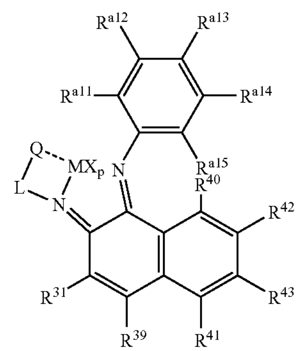 |
| Structure 36e |
| 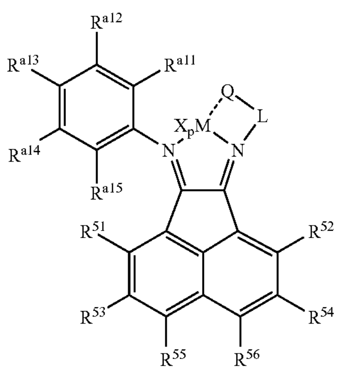 |
| Structure 37e |
| 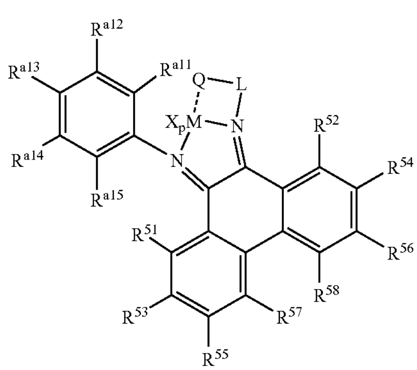 |
| Structure 38e |

TABLE 6-continued

| Example α-Diimine Metal Complexes |
|---|
| 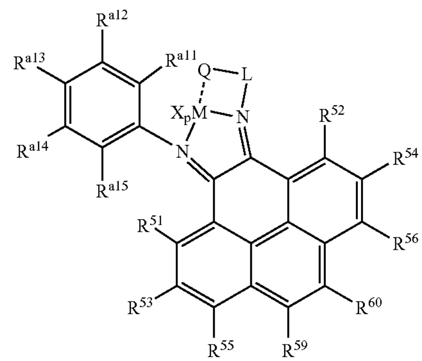 |
| Structure 39e |

The α-diimine metal complexes of Table 6 can be prepared utilizing various methods as described herein. Depending upon the α-diimine metal complex preparation method the α-diacyl compound, the two primary amines, the metal salt, the α-acylimine compounds, and/or the α-acylimine metal complexes can each be separate and independent elements in the preparation of the α-diimine metal complex. Therefore, the $R^x$s of α-diacyl compounds having Structures 1-12 (Table 1), the metal salts, the $R^{ax}$s of the primary amines having Structures 1a-4a, the linking groups 1L-5L (Table 3) of the primary amine having Structure 5a, and the metal salt complexing group $R^{cx}$s having Structures 1c-22c (Table 2) of the primary amine having Structure 5a are separate and independent elements of the α-diimine metal complexes of Table 6. Thus, the α-diimine metal complexes of Table 6 can be further described using any combination of the $R^x$s of α-diacyl compound having Structures 1-12 (Table 1) as described herein, the metal salts as described herein, the $R^{ax}$s of the primary amines having Structures 1a-4a as described herein, the linking groups 1L-5L (Table 3) of the primary amine having Structure 5a as described herein, and the metal salt complexing group $R^{cx}$s having Structures 1c-22c (Table 2) of the primary amine having Structure 5a as described herein.

One skilled in the art will recognize that α-diimine metal complex Structures 14e though 39e formally show a monomeric form of a tricoordinate metal salt complexed to a tridentate α-diimine compound. However, it should be noted that these structures do not necessarily imply that dimeric forms of Structures having bridging $X_p$ groups are not formed. Additionally, it should also be noted that while α-diimine metal complex Structures 14e though 39e, and other Structures disclosed herein, indicate that the two imine nitrogen and the metal salt complexing group form a dative bond with the metal atom, these structures do not necessarily imply that the three ligands of the tridentate α-diimine compound are complexed to the metal salt. For example, in example 7 a tricoordinate metal salt is complexed to a tridentate α-diimine compound to form an α-diimine metal complex isolated in a dimeric form and the metal salt complexing group is not complexed to the metal salt. The examples further illustrate that this α-diimine metal complex of example 7 can be utilized within other aspects of the invention as described herein. Provided the teachings of the present disclosure, the skilled artisan may also recognize that the α-diimine metal complex Structures herein do not show the presence of any complexing solvent molecules and may appreciate that depending upon the solvent(s) used in the preparation of α-diimine metal complex Structures 1e though 39e, and other Structures disclosed herein, the α-diimine metal complexes can be isolated in forms having complexed solvent atoms, (e.g. THF, acetonitrile).

α-Diimine Compounds

The α-diimine compounds can be described using any one of several descriptions. While these descriptions may be indicated by labels such first description, second description, etc., these labels do not indicate a preference towards a particular description of the α-diimine compounds.

In a first description, the α-diimine compound can be minimally described as a compound comprising an α-diimine group. In embodiments, the α-diimine compound can be described as a compound comprising 1) an α-diimine group and 2) two α-diimine nitrogen groups. In this first α-diimine compound description, the α-acylimine group can be further described as being derived from an α-diacyl compound. Thus, alternatively, the α-acylimine compound can be described as compound comprising 1) an α-diimine group derived from an α-diacyl compound and 2) two α-diimine nitrogen groups; or alternatively, as compound consisting of 1) an α-diimine group derived from an α-diacyl compound and 2) two α-diimine nitrogen group. In the first α-diimine compound description, the α-diacyl compound, and each of the two α-diimine nitrogen groups are separate and independent elements of the α-diimine compound description. Thus, within the first α-diimine compound description, the α-diimine compound can have any combination of the α-diacyl compound as described herein and the α-diimine nitrogen groups as described herein.

In the first α-diimine compound description, the α-diacyl compound from which the α-diimine compound is derived can be any α-diacyl compound described herein. In embodiments, the two α-diimine nitrogen groups can each independently comprise an organyl group; alternatively, comprise a metal salt complexing group; alternatively, comprise a metal salt complexing group and a linking group linking the metal salt complexing group to the α-diimine nitrogen group nitrogen atom; alternatively, comprise an organyl group consisting of inert functional groups; alternatively, comprise a hydrocarbyl group; alternatively, consist of an organyl group; alternatively, consist of a metal salt complexing group and a linking group linking the metal salt complexing group to the α-diimine nitrogen group nitrogen atom; alternatively, consist of an organyl group consisting of inert functional groups; or alternatively, consist of a hydrocarbyl group.

In some embodiments, the two α-diimine nitrogen groups can be the same. In other embodiments, the two α-diimine nitrogen groups can be different. In particular embodiments, the two α-diimine nitrogen groups comprise two different organyl groups; alternatively, comprise two different organyl groups consisting of inert functional groups; alternatively, comprise two different hydrocarbyl groups; alternatively, consist of two different organyl groups; alternatively, consist of two different organyl groups consisting of inert functional groups; or alternatively, consist of two different hydrocarbyl groups. In some other particular embodiments, the first α-diimine nitrogen group comprises an organyl group consisting of inert functional groups and the second α-diimine nitrogen group comprises a metal salt complexing group; alternatively, the first α-diimine nitrogen group comprises an organyl group consisting of inert functional groups and the second α-diimine nitrogen group comprises a metal salt complexing group and a linking group linking the metal salt complexing group to second α-diimine nitrogen group nitrogen atom; alternatively, the first α-diimine nitrogen group comprises a hydrocarbyl group and the second α-diimine nitrogen group comprises a metal salt complexing group; alternatively, the first α-diimine nitrogen group comprises a hydrocarbyl group and the second α-diimine nitrogen group comprises a metal salt complexing group and a linking group linking the metal salt complexing group to the second α-diimine nitrogen group nitrogen atom; alternatively, the first α-diimine nitrogen group consists of an organyl group consisting of inert functional groups and the second α-diimine nitrogen group consists of a metal salt complexing group and a linking group linking the metal salt complexing group to the second α-diimine nitrogen group nitrogen atom; or alternatively, the first α-diimine nitrogen group consists of a hydrocarbyl group and the second α-diimine nitrogen group consists of a metal salt complexing group and a linking group linking the metal salt complexing group to the second α-diimine nitrogen group nitrogen atom.

As the primary amine —$NH_2$ group becomes the α-diimine group's nitrogen atom, the organyl group, metal salt complexing group, linking group, organyl group consisting of inert functional groups, or hydrocarbyl groups of the primary amine becomes an α-diimine nitrogen group. Thus, the α-diimine nitrogen groups can have the same embodiments as the organyl group, metal salt complexing group, linking group, organyl group consisting of inert functional groups, and hydrocarbyl groups of the primary amine as described herein. Therefore, the organyl group, metal salt complexing group, linking group, organyl group consisting of inert functional groups, and hydrocarbyl groups of the primary amines embodiment described herein are generally applicable to the description of the α-acylimine compound with the proviso that the linking group links the metal salt complexing group to the imine nitrogen atom of the α-acylimine group instead of the —$NH_2$ group of the primary amine.

In a second description, the α-diimine compound can be described as an α-diimine compound product of contacting an α-diacyl compound with two primary amines. While this particular α-diimine compound description appears to imply a specific α-diimine compound synthesis method, this is not the intent of α-diimine compound. The method of preparing the α-diimine compound is independent of the description of the α-diimine metal complex. Thus, while the α-diimine compound can be described as an α-diimine compound product of contacting an α-diacyl compound with two primary amines, the α-diimine compound can be prepared by using any method described herein. In the second α-diimine compound description the α-diacyl compound and each of the two primary amines are separate and independent elements of the α-diimine compound description. Thus, within the second α-diimine compound description, the α-diimine compound can have any combination of the α-diacyl compound as described herein and two primary amines as described herein.

In the second α-diimine compound description, the α-diacyl compound can be any α-diacyl compound described herein. In an aspect, the two primary amines are the same. In some embodiments, the two primary amines are different. In embodiments, at least one of the primary amines consists of an —$NH_2$ group and a hydrocarbyl group or consists of an —$NH_2$ group and an organyl group consisting of inert functional groups. In particular embodiments, the α-diimine compound is a product of reacting an α-diacyl compound with two different the two primary amines comprising an —$NH_2$ group and an organyl groups; alternatively, comprising an —$NH_2$ group and an organyl groups consisting of inert functional groups; alternatively, comprising an —$NH_2$ group and a hydrocarbyl group; alternatively, consisting of an —$NH_2$ group and an organyl groups; alternatively, consisting of an —$NH_2$ group and an organyl group consisting of inert functional groups; or alternatively, consisting of an —$NH_2$ group and a hydrocarbyl group.

In embodiments, the α-diimine compound is a product of reacting α-diacyl compound with two different primary amines. In particular embodiments, the α-diimine compound is a product of reacting α-diacyl compound with two different primary amines, wherein the first primary amine comprises an —$NH_2$ group and an organyl group consisting of inert functional groups and the second primary amine comprises an —$NH_2$ group and a metal salt complexing group; alternatively, the first primary amine comprises an —$NH_2$ group and an organyl group consisting of inert functional groups and the second primary amine comprises an —$NH_2$ group, a metal salt complexing group, and a linking group linking the metal salt complexing group the —$NH_2$ group; alternatively, the first primary amine comprises an —$NH_2$ group and a hydrocarbyl group and the second primary amine comprises an —$NH_2$ group and a metal salt complexing group; alternatively, the first primary amine comprises an —$NH_2$ group and a hydrocarbyl group and the second primary amine comprises an —$NH_2$ group, a metal salt complexing group, and a linking group linking the metal salt complexing group to the —$NH_2$ group; alternatively, the first primary amine consists of an —$NH_2$ group and an organyl group consisting of inert functional groups and the second primary amine consists of an —$NH_2$ group, a metal salt complexing group, and a linking group linking the metal salt complexing group to the —$NH_2$ group; or alternatively, the first primary amine consists of an —$NH_2$ group and a hydrocarbyl group and the second primary amine consists of an —$NH_2$ group, a metal salt complexing group, and a linking group linking the metal salt complexing group to the —$NH_2$ group.

In a third description, the α-diimine compounds can be described as a product produced by any process described herein capable of producing the α-diimine compounds and may be further described using any embodiments of the processes described herein.

In a fourth description, the α-diimine compound can be described as having any a structure as indicated in Table 7. In embodiments, the α-diimine compound can have Structure 1f; alternatively, Structure 2f; alternatively, Structure 3f, Structure 4f, or Structure 5f; alternatively, Structure 6f; alternatively, Structure 7f, Structure 8f, or mixtures of Structure 9f and Structure 10f; alternatively, Structure 11f, Structure 12f, or Structure 13f; or alternatively, Structure 11f. In some embodiments, $R^{a1}$ and $R^{a1'}$ of Structures 1f-13f are different (not identical). In some embodiments, $R^{a1}$ of Structures 1f-13f can have Structure 1 g (derived from a primary amine having Structure 3a). In other embodiments, $R^{a1'}$ of Structures 1f-13f can have Structure 1 g can have Structure 2 g (derived from a primary amine having Structure 4 a). In other embodiments, Ra1 of Structures 1f-13f can have Structure 1 g and $R^{a1'}$ of Structures 1f-13f can have Structure 2 g. In yet other embodiments, wherein $R^{a1}$ and $R^{a1'}$ of Structures 1f-13f can have Structure 1 g and Structure 2 g, respectively, Structure 1 g and Structure 2 g are different (not identical).

In some embodiments, the α-diimine compound can have Structure 14f or Structure 27f; alternatively, Structure 15f or Structure 28f; alternatively, Structure 16f, Structure 17f, Structure 18f, Structure 29f, Structure 30f, or Structure 31f, alternatively, Structure 19f or Structure 32f; alternatively, Structure 20f, Structure 21f, mixtures of Structure 22f and Structure 23f, Structure 33f, Structure 34f, or mixtures of Structure 35f and Structure 36f; alternatively, Structure 24f, Structure 25f, Structure 26f, Structure 37f, Structure 38f, or Structure 39f; or alternatively, Structure 24f or Structure 37f. In other embodiments, the α-diimine compound can have Structure 14f, alternatively, Structure 15f; alternatively, Structure 16f, Structure 17f, or Structure 18f; alternatively, Structure 19f; alternatively, Structure 20f, Structure 21f, or mixtures of Structure 22f and Structure 23f, alternatively, Structure 24f, Structure 25f, or Structure 26f, or alternatively, Structure 24f. In yet other embodiments, the α-diimine compound can have Structure 27f, alternatively, Structure 28f, alternatively, Structure 29f, Structure 30f, or Structure 31f, alternatively, Structure 32f, alternatively, Structure 33f, Structure 34f, or mixtures of Structure 35f and Structure 36f; alternatively, Structure 37f, Structure 38f, or Structure 39f; or alternatively, Structure 37f.

TABLE 7

Example α-Diimine Compounds

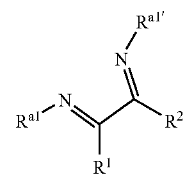
Structure 1f

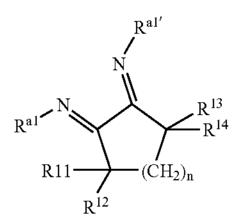
Structure 2f

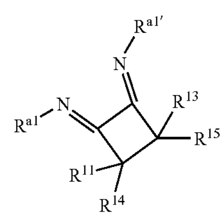
Structure 3f

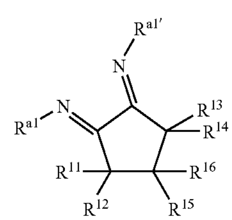
Structure 4f

TABLE 7-continued
Example α-Diimine Compounds
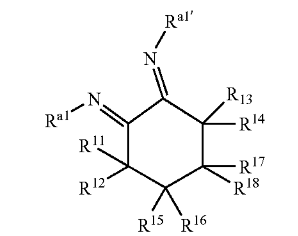
Structure 5f
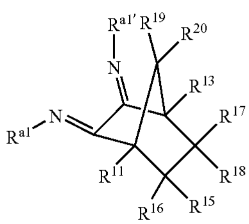
Structure 6f
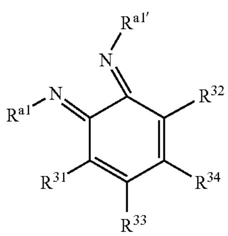
Structure 7f
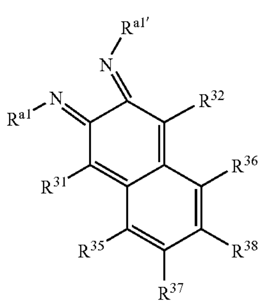
Structure 8f
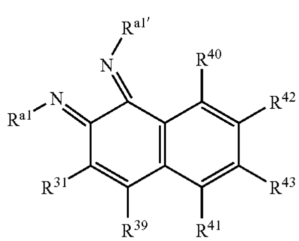
Structure 9f
TABLE 7-continued
Example α-Diimine Compounds
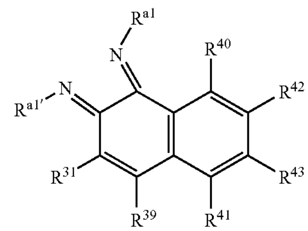
Structure 10f
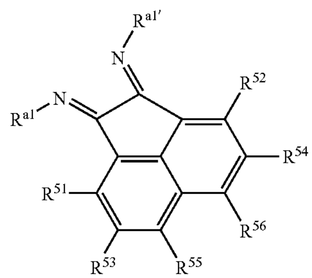
Structure 11f
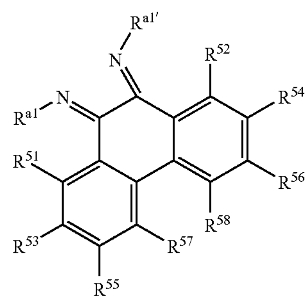
Structure 12f
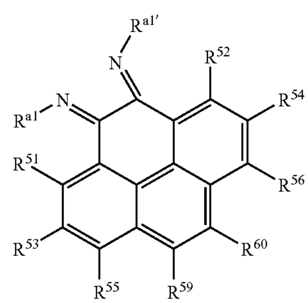
Structure 13f
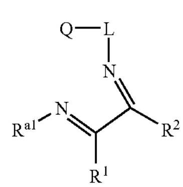
Structure 14f TABLE 7-continued
Example α-Diimine Compounds
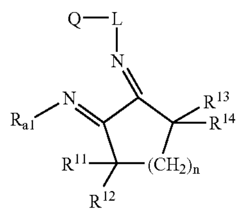
Structure 15f
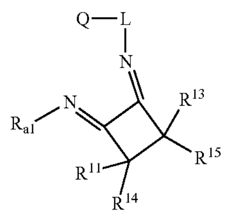
Structure 16f
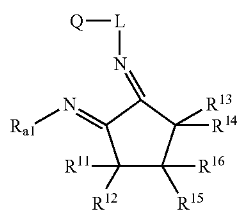
Structure 17f
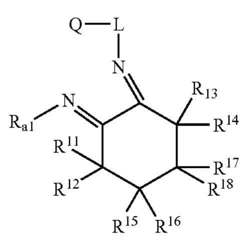
Structure 18f
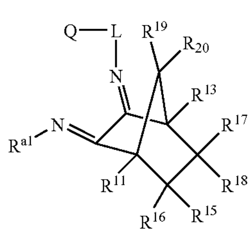
Structure 19f
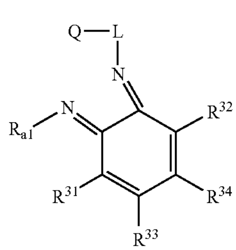
Structure 20f
TABLE 7-continued
Example α-Diimine Compounds
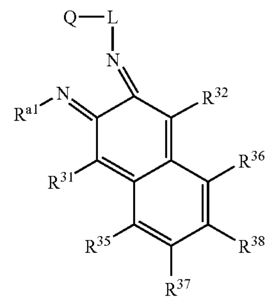
Structure 21f
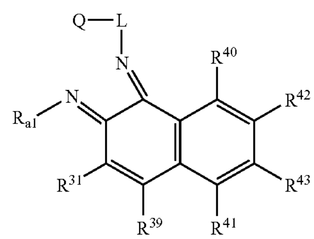
Structure 22f
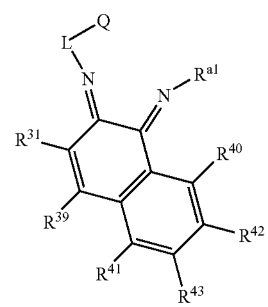
Structure 23f
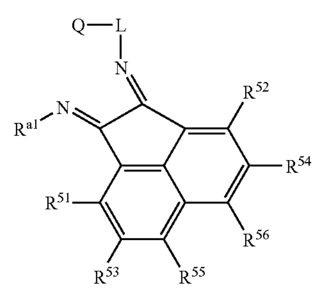
Structure 24f
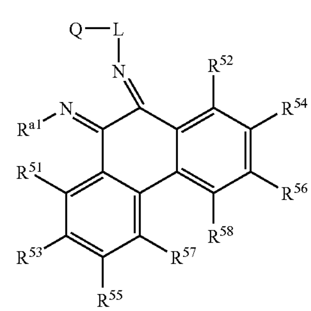
Structure 25f TABLE 7-continued
Example α-Diimine Compounds
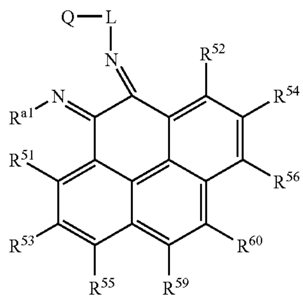
Structure 26f
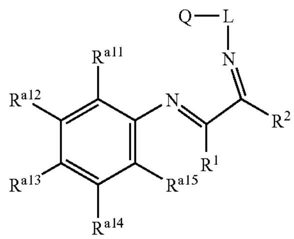
Structure 27f
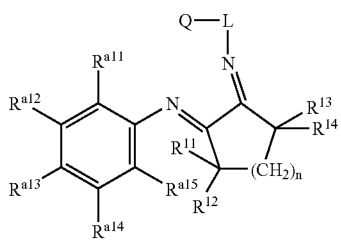
Structure 28f
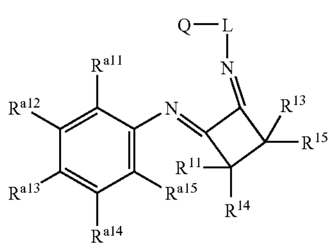
Structure 29f
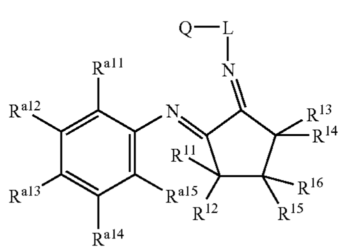
Structure 30f
TABLE 7-continued
Example α-Diimine Compounds
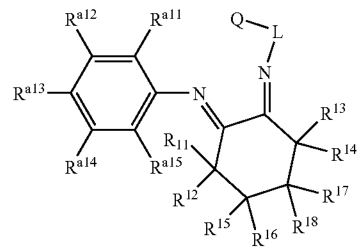
Structure 31f
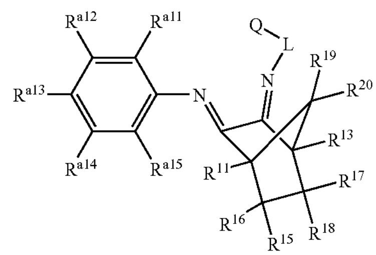
Structure 32f
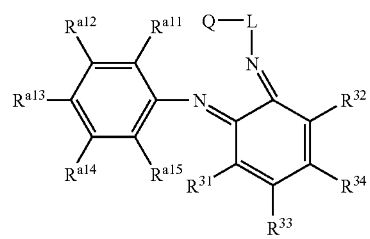
Structure 33f
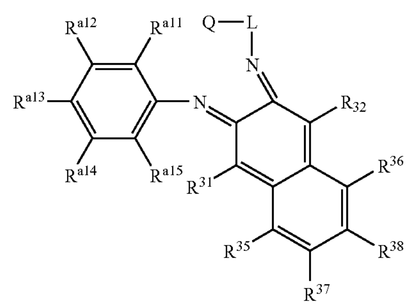
Structure 34f
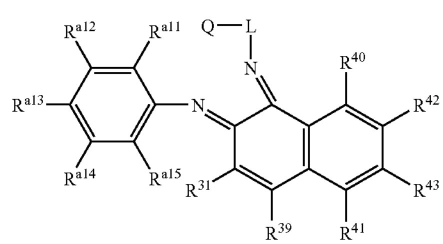
Structure 35f TABLE 7-continued

| Example α-Diimine Compounds |
| --- |
| 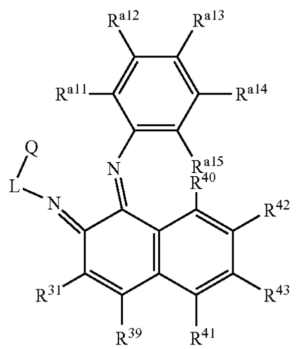 Structure 36f |
| 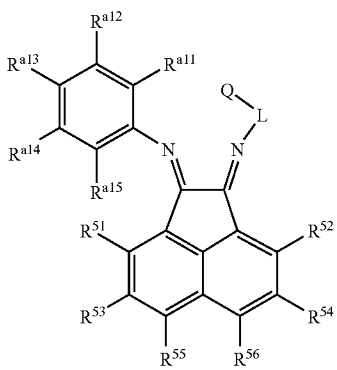 Structure 37f |
| 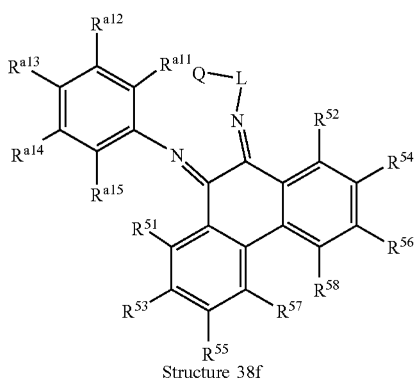 Structure 38f |
| 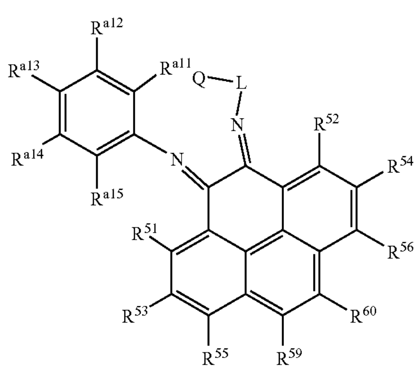 Structure 39f |

Ideally, the α-diimine compounds of Table 7 could be prepared from an α-diacyl compound and two primary amines which are separate and independent elements. Thus, the $R^x$s of α-diacyl compound having Structures 1-12 (Table 1), the $R^{ax}$s of the primary amines having Structures 1a-4a, the linking groups 1L-5L (Table 3) of the primary amine having Structure 5a, and the metal salt complexing group $R^{cx}$s having Structures 1c-22c (Table 2) of the primary amine having Structure 5a are separate and independent elements of the α-diimine compounds of Table 7. Thus, the α-diimine compounds of Table 7 can be further described using any combination of the $R^x$s of α-diacyl compounds having Structures 1-12 (Table 1) as described herein, the $R^{ax}$s of the primary amines having Structures 1a-4a as described herein, the linking groups 1L-5L (Table 3) of the primary amine having Structure 5a as described herein, and the metal salt complexing group $R^{cx}$s having Structures 1c-22c (Table 2) of the primary amine having Structure 5a as described herein.

General Metal Complex and Intermediate Synthesis Methods

An aspect of the invention relates to methods of preparing α-diimine metal complexes. As described herein, production of particular α-diimine metal complexes can motivate selection of particular starting materials, (e.g. α-diacyl compounds, primary amines, and metal salts), intermediates (e.g. α-acylimine compounds and α-acylimine metal complexes), and α-diimine metal complexes.

The methods for producing an α-diimine metal complex generally comprise forming at least one imine bond in the presence of a metal salt, a metal complex, or combinations thereof and recovering an α-diimine metal complex. In some embodiments, the method for producing an α-diimine metal complex comprises forming at least one imine bond in the presence of a metal salt, α-acylimine metal complex, or combinations thereof and recovering an α-diimine metal complex. In some embodiments, the method for producing an α-diimine metal complex comprises forming at least one imine bond in the presence of a metal salt. In further embodiments, the method for producing an α-diimine metal complex comprises forming at least one imine bond in the presence of an α-acylimine metal complex. Within these methods, the metal salt or α-acylimine metal complex, the α-diimine metal complex formed, and the specific imine bond or imine bonds formed, are separate and independent elements. Given the teachings provided, the skilled artisan can recognize which combination of ingredients may lead to a desired α-diimine metal complex that includes the desired elements. The combinations of compounds that can be used to produce a particular α-diimine metal complex utilizing the synthesis methods are described herein.

The α-diacyl compounds, primary amines, and metal salts are separate and independent elements in the preparation of the α-diimine metal complexes. Additionally, the intermediate α-acylimine compounds and/or the α-acylimine metal complexes can be separate and independent elements of the α-diimine metal complex preparation methods. Thus, the α-diimine metal complex preparation methods can use any combination of the α-diacyl compounds described herein, primary amines described herein, metal salts described herein, α-acylimine compounds described herein, and α-acylimine metal complexes described herein to produce the desired α-diimine metal complexes utilizing the herein described preparation methods. Provided the teachings of the present disclosure, a skilled artisan should recognize how combinations of ingredients may be varied in order to produce a desired metal complex including the desired elements and their variations.

Methods for Preparing α-Acylimine Compounds

The method of preparing an α-acylimine compound comprises contacting an α-diacyl compound and a primary amine. In some embodiments, the α-acylimine compound is recovered. In other embodiments, the α-acylimine compound can be purified using methods known to those skilled in the art, such as recrystallization. In yet other embodiments, the α-acylimine compound is used as is, e.g., as an unpurified reaction product.

Within the α-acylimine compound production method the primary amine and the α-diacyl compound are separate and independent elements. Thus, α-acylimine compound can be prepared using any combination of the primary amine as described herein and the α-diacyl compound as described herein. In some embodiments, the primary amine can be a mixture of similar primary amines, e.g. a mixture of primary amines consisting of an —$NH_2$ group and hydrocarbyl group, a mixture of primary amines consisting of an —$NH_2$ group and an organyl group consisting of inert functional groups, or a mixture of primary amines comprising an —$NH_2$ group and a metal salt complexing group. In additional embodiments, the α-diacyl compound can be a mixture of α-diacyl compounds.

Solvents and catalysts that can be utilized within the α-acylimine compound synthesis methods are described herein and are generally applicable to methods of producing α-acylimine compounds. Production conditions such as reagent molar ratios, temperatures, pressure, and contact times, among others, are also described herein and are generally applicable to methods of producing α-acylimine compounds.

Methods for Preparing α-Acylimine Metal Complexes

Various synthesis paths can be employed to produce the α-acylimine metal complexes. Described herein are several preparation methods that can be utilized. While the α-acylimine metal complex preparation methods may be designated as 'first method', 'second method', etc . . . , these designations do not imply any preference for a particular method of preparing the α-acylimine metal complexes.

In a first method, the method of preparing an α-acylimine metal complex comprises contacting an α-acylimine compound with a metal salt. In some embodiments, the α-acylimine metal complex is recovered. In other embodiments, the α-acylimine metal complex can be purified using methods known to those skilled in the art, such as recrystallization. In yet other embodiments, the α-acylimine metal complex can be used as is.

Within the first α-acylimine metal complex production method the metal salt and α-acylimine compound are separate and independent elements. Thus, utilizing the first α-acylimine metal complex production method the α-acylimine metal complex can be prepared using any combination of the metal salt as described herein and the α-acylimine compound as described herein. In some embodiments, the α-acylimine compound can be a mixture of similar α-acylimine compounds, e.g. a mixture of α-acylimine compounds produced by contacting α-diacyl compound with a mixture of primary amines consisting of an —$NH_2$ group and a hydrocarbyl group, a mixture of α-acylimine compounds produced by contacting α-diacyl compound with a mixture of primary amines consisting of an —$NH_2$ group and an organyl group consisting of inert functional groups, or a mixture of α-acylimine compounds produced by contacting an α-diacyl compound with a mixture of primary amines comprising an —$NH_2$ group and an metal salt complexing group.

In a second method, the method for preparing an α-acylimine metal complex comprises contacting an α-diacyl compound, a metal salt, and a primary amine. In some embodiments, an α-acylimine metal complex is recovered. In other embodiments, the α-acylimine metal complex can be purified using methods know to those skilled in the art, such as recrystallization. In yet other embodiments, the α-acylimine metal complex can be used as is.

In a third method, the method to produce an α-acylimine metal complex comprises a) contacting an α-diacyl compound and a primary amine to form a mixture containing an α-acylimine compound, and b) contacting a metal salt with the mixture containing the α-acylimine compound. In some embodiments, an α-acylimine metal complex is recovered. In other embodiments, the α-acylimine metal complex can be purified using methods known to those skilled in the art, such as recrystallization. In yet other embodiments, the α-acylimine metal complex is used as is.

Within the second and third α-acylimine metal complex production methods, the primary amine, the α-diacyl compound, and the metal salt are separate and independent elements. Thus utilizing the second and third α-acylimine metal complex production methods, the α-acylimine metal complex can be prepared utilizing any combination of the primary amine as described herein, the α-diacyl compound as described herein, and the metal salt as described herein. Provided the teachings of the present disclosure, a skilled artisan can recognize how combinations of ingredients, e.g.—a primary amine, α-diacyl compound, and metal salt, may be varied in order to produce a desired metal complex including those ingredients and their variations. In some embodiments within the second and/or third α-acylimine metal complex production methods, the primary amine can be a mixture of similar primary amines, e.g. a mixture of primary amines consisting of an —$NH_2$ group and hydrocarbyl group, a mixture of primary amines consisting of an —$NH_2$ group and an organyl group consisting of inert functional groups, or a mixture of primary amines comprising an —$NH_2$ group and a metal salt complexing group. In some embodiments, within the second and third α-acylimine metal complex production methods, the α-diacyl compound can be a mixture of α-diacyl compounds.

Solvent and catalysts and solvents that can be utilized within α-acylimine metal complex synthesis methods are described herein and are generally applicable to methods of producing α-acylimine metal complexes. Production conditions such as reagent molar ratios, temperatures, pressure, and contact times, among others, are also described herein and are generally applicable to methods of producing α-acylimine metal complexes.

Methods for Preparing α-Diimine Metal Complexes

Various synthesis paths can be employed to produce the α-diimine metal complexes by forming at least one imine bond in the presence of a metal salt, α-acylimine metal complex, or combinations thereof. Described herein are several methods that can be utilized. While methods may be designated as 'first method', 'second method', etc., these designations do not imply any preferences for particular method of preparing α-diimine metal complexes.

In a first method, the method to produce an α-diimine metal complex, comprises a) contacting an α-acylimine metal complex and a primary amine to form a mixture, and b) recovering the α-diimine metal complex from the mixture. In some embodiments, the α-diimine metal complex can be purified using methods known to those skilled in the art, such as recrystallization. In yet other embodiments, the α-acylimine metal complex can be used as is.

Within the first α-diimine metal complex production method, the α-acylimine metal complex and the primary amine are separate and independent elements. Thus in the first α-diimine metal complex production method, the α-diimine metal complex can be prepared utilizing any combination of α-acylimine metal complex as described herein and primary amine as described herein. In some particular embodiments, the primary amine used to produce the α-acylimine compound of the α-acylimine metal complex and the primary amine contacted with the α-acylimine metal complex are different (not identical). For example, in two non-limiting examples, the primary amine can comprise an $—NH_2$ group and a metal salt complexing group and the α-acylimine metal complex can comprise a complex between an α-acylimine compound and metal salt, wherein the α-acylimine compound comprises 1) an α-acylimine group derived from an α-diacyl compound and 2) an imine nitrogen group consisting of a hydrocarbyl group; or the primary amine can consist of an $—NH_2$ group and a hydrocarbyl group and the α-acylimine metal complex can comprise a complex between an α-acylimine compound and metal salt wherein the α-acylimine compound comprises 1) an α-acylimine group derived from an α-diacyl compound and 2) an imine nitrogen group comprising a metal salt complexing group. Provided the teachings of the present disclosure, the skilled artisan should recognize how combinations of particular α-acylimine metal complexes and primary amines can be varied in order to produce an α-acylimine metal complex that includes the α-acylimine metal complex and primary amine selected.

In some embodiments, the primary amine can be a mixture of similar primary amines, e.g. a mixture of primary amines consisting of an $—NH_2$ group and hydrocarbyl group, a mixture of primary amines consisting of an $—NH_2$ group and an organyl group consisting of inert functional groups, or a mixture of primary amines comprising an $—NH_2$ group and a metal salt complexing group. In some embodiments, the α-acylimine metal complex can be a mixture of similar α-acylimine metal complexes, e.g. a mixture of α-acylimine compounds produced by contacting an α-diacyl compound with a mixture of primary amines consisting of an $—NH_2$ group and a hydrocarbyl group, a mixture of α-acylimine compounds produced by contacting an α-diacyl compound with a mixture of primary amines consisting of an $—NH_2$ group and an organyl group consisting of inert functional groups, or a mixture of α-acylimine compounds produced by contacting an α-diacyl compound with a primary amine comprising an $—NH_2$ group and an metal salt complexing group.

In a second method, the method to produce an α-diimine metal complex comprises a) contacting an α-acylimine compound, a metal salt, and a primary amine to form a mixture, and b) recovering the α-diimine metal complex from the mixture. In some embodiments, the α-diimine metal complex may be purified using methods known to those skilled in the art, such as recrystallization. In yet other embodiments, the α-acylimine metal complex can be used as is, e.g., as an unpurified reaction product.

In a third method, the method to produce an α-diimine metal complex comprises a) contacting an α-acylimine compound and a metal salt to form a mixture containing an α-acylimine metal complex b) contacting a primary amine with the mixture containing an α-acylimine metal complex and c) recovering the α-diimine metal complex. In some embodiments, the α-diimine metal complex may be purified using methods known to those skilled in the art, such as recrystallization. In yet other embodiments, the α-acylimine metal complex can be used as is, e.g., as an unpurified reaction product.

Within the second and third α-diimine metal complex production methods, the α-acylimine compound, the metal salt, and the primary amine are separate and independent elements. Thus within the second and third α-diimine metal complex production methods, the α-diimine metal complex can be produced using any combination of the α-acylimine compound as described herein, the metal salt as described herein, and the primary amine as described herein. In some particular embodiments, the primary amine used to produce the α-acylimine compound and the primary amine contacted with the α-acylimine compound are different (not identical). For example, in two non-limiting examples, the primary amine used to produce the α-acylimine compound can consist of an $—NH_2$ group and a hydrocarbyl group and the primary amine contacted with the α-acylimine compound and metal salt or mixture containing an α-acylimine metal complex comprises an $—NH_2$ group and metal salt complexing group; or the primary amine used to produce the α-acylimine compound consists of an $—NH_2$ group and a hydrocarbyl group and the primary amine contacted with the α-acylimine compound and metal salt or mixture containing an α-acylimine metal complex consists of an $—NH_2$ group and hydrocarbyl group different than the primary amine utilized to produce α-acylimine compound. Provided the teachings of the present disclosure, the skilled artisan should recognize how combinations of particular α-acylimine compounds, metal salts, and primary amines can be varied in order to produce an α-acylimine metal complex including the α-acylimine compound, metal salt, and primary amine selected.

In some embodiments, the α-acylimine compound can be a mixture of similar α-acylimine compounds, e.g. a mixture of α-acylimine compounds produced by contacting α-diacyl compound with a mixture of primary amine consisting of an $—NH_2$ group and a hydrocarbyl group, a mixture of α-acylimine compounds produced by contacting α-diacyl compound with a mixture of primary amine consisting of an $—NH_2$ group and an organyl group consisting of inert functional groups, or a mixture of α-acylimine compounds produced by contacting an α-diacyl compound with a mixture of primary amine comprising an $—NH_2$ group and a metal salt complexing group. In other embodiments, the primary amine used in the synthesis of the α-diimine metal complex can be a mixture of similar primary amines, e.g. a mixture of primary amines consisting of an $—NH_2$ group and hydrocarbyl group, a mixture of primary amines consisting of an $—NH_2$ group and an organyl group consisting of inert functional groups, or a mixture of primary amines comprising an $—NH_2$ group and a metal salt complexing group.

In some particular embodiments, the primary amine utilized in the first, second, and third α-diimine metal complex production methods described above is a different primary amine than that utilized to produce the α-acylimine compound or α-acylimine metal complex. For example in two non-limiting cases, if the primary amine used to produce α-acylimine compound or α-acylimine metal complex comprises an $—NH_2$ group and an organyl group then the primary amine contacted with the α-acylimine compound or α-acylimine metal complex could be a different primary amine comprising an $—NH_2$ group and an organyl group; or, if the primary amine used to produce α-acylimine compound or α-acylimine metal complex comprises an $—NH_2$ group and an organyl group consisting of inert functional groups, then the primary amine contacted with the α-acylimine compound or α-acylimine metal complex could be primary amines comprising an —$NH_2$ group and a metal salt complexing group. One skilled in the art will recognize that these are non-limiting examples and can envision that within these embodiments any combination of the two primary amines as described herein can be utilized with the stipulation that the two primary amines are different.

In a fourth method, the method to produce the α-diimine metal complex comprises a) contacting an α-diimine compound with a metal salt, and b) recovering the α-diimine metal salt. In further embodiments, the α-diimine metal complex is purified using methods known to those skilled in the art, such as recrystallization. Within the fourth α-diimine metal complex production method, the α-diimine compound and metal salt are separate and independent elements. Thus, the α-diimine metal complex can be produced utilizing any combination of the α-diimine compound as described herein and the metal salt as described herein. Provided the teachings of the present disclosure, the skilled artisan should recognize how combinations of α-diimine compound and metal salt may be varied in order to produce a particular α-acylimine metal complex including the α-diimine compound and metal salt selected.

Applicable catalyst and solvent that can be utilized within these α-diimine metal complex synthesis methods are described herein and are generally applicable to methods of producing α-diimine metal complexes. Production conditions such as molar ratios, temperatures, pressure, and contact times, among others, are also described herein and are generally applicable to methods of producing α-diimine metal complexes.

The α-diimine metal complex synthesis method can also comprise any step required to produce the α-acylimine compounds and/or the α-acylimine metal complexes utilized in the α-diimine metal complex syntheses. As such, the α-diimine metal complex synthesis can be described as process utilizing an α-diacyl compound, two primary amines, and a metal salt and having an α-acylimine compounds and/or α-acylimine metal complexes as an intermediate product which can be isolated and/or purified or used as is. Provided these α-diimine metal complex synthesis descriptions the skilled artisan may recognize that the two primary amines can be labeled first or second primary amine as needed to adequately describe the process. One skilled in the art provided these teachings may also recognize that even though the first, second, and third α-diimine metal complex synthesis steps are annotated with steps a), b), etc., the α-diimine metal complex synthesis steps can be re-annotated to provide consistent step annotation to incorporate steps utilized in producing the α-acylimine compounds and/or the α-acylimine metal complexes into the α-diimine metal complex synthesis descriptions. Additionally, the act of incorporating the steps required to produce the α-acylimine compounds and/or α-acylimine metal complexes into the methods of producing the α-diimine metal complexes can create a situation wherein a synthesis path may include more than one mixture. In these scenarios, such mixtures can be prefaced with a descriptor such as first, second, etc., to provide unambiguous references to the mixtures within the α-diimine metal complex synthesis. Thus, in a non limiting example, a process to produce an α-acylimine metal complex from an α-diacyl compound, two primary amines, and a metal salt by putting together the various compound descriptions described herein can comprise the steps a) contacting an α-diacyl compound with a first primary amine to form a first mixture containing an α-acylimine compound; b) contacting the first mixture with a metal salt to form a second mixture containing an α-acylimine metal complex, c) contacting a second primary amine with the second mixture to form an α-diimine metal complex, and d) recovering the α-diimine metal complex.

Reagent Molar Ratios, Solvents, Reaction Conditions and Metal Complex and Intermediate Yields As described herein, an α-diimine metal complex may be produced via various synthesis paths. Molar ratios of reagents employed in the various synthesis paths are indicated herein and can be generally applied to the methods of producing the α-diimine metal complex as described herein.

Generally, whenever a primary amine is contacted with an α-diacyl compound, e.g. to form an α-acylimine compound or an α-acylimine metal complex, the molar ratio of primary amine to α-diacyl compound can be any molar ratio capable of producing the α-acylimine compound or α-acylimine metal complex. In some embodiments, the molar ratio of primary amine to α-diacyl compound can be less than 1.1:1; alternatively, less than 1.05:1; alternatively, less than 1.02:1; or alternatively, less than 1:1. In other embodiments, the molar ratio of primary amine to α-diacyl compound can range from 0.75:1 to 1.1:1; alternatively, range from 0.85:1 to 1.05:1; or alternatively, range from 0.9:1 to 1.02:1. In yet other embodiments, the molar ratio of primary amine to α-diacyl compound can be about 1:1. In yet other embodiments, the molar ratio of primary amine to α-diacyl compound can be greater than 1:1 when the remaining acyl group of the resultant α-acylimine compound does not readily react with additional equivalents of the primary amine under the reaction conditions employed. In this embodiment, the use of excess primary amine can prove desirable.

Generally, whenever an α-diacyl compound is contacted with a metal salt, e.g. to form an α-acylimine metal complex by contacting an α-diacyl compound, a primary amine, and metal salt, the molar ratio of metal salt to α-diacyl compound can be any molar ratio capable of producing an α-acylimine metal complex. In some embodiments, the molar ratio of metal salt to α-diacyl compound to is greater than 0.75:1; alternatively, greater than 0.85:1; alternatively, greater than 0.9:1; or alternatively, greater than 0.95:1. In other embodiments, the molar ratio of metal salt to α-diacyl compound can range from 0.75:1 to 1.25:1; alternatively, range from 0.85:1 to 1.15:1; or alternatively, range from 0.9:1 to 1.1:1. In yet other embodiments, the molar ratio of metal salt to α-diacyl compound can be about 1:1.

Generally, whenever primary amine is contacted with a metal salt, e.g. to form an α-acylimine metal complex or an α-diimine metal complex, the molar ratio of primary amine to metal salt can be any molar ratio capable of producing the acylimine metal complex or the α-diimine metal complex. In some embodiments, the molar ratio of primary amine to metal salt can be less than 1.1:1; alternatively, less than 1.05:1; alternatively, less than 1.02:1; or alternatively, less than 1:1. In yet other embodiments, molar ratio of amine to metal salt can range from 0.75:1 to 1.1:1; alternatively, range from 0.85:1 to 1.05:1; or alternatively, range from 0.9:1 to 1.02:1. In certain embodiments, the molar ratio of amine to metal salt can be about 1:1.

Generally, whenever an α-diacyl compound is contacted with a primary amine and a metal salt, e.g. to form an α-acylimine metal complex, the molar ratio of the primary amine to metal salt can be any molar ratio capable of producing an α-acylimine metal complex. In some embodiments, the molar ratio of primary amine to metal salt to α-diacyl compound can range from 0.75:1:1 to 1.1:1:1; alternatively, range from 0.85:1:1 to 1.05:1:1; or alternatively, range from 0.9:1:1 to 1.02:1:1. In certain embodiments, the molar ratio of primary amine to metal salt to α-diacyl compound is about 1:1:1.

Generally, whenever an α-acylimine compound is contacted with a metal salt, e.g. to form an α-acylimine metal complex or an α-diimine metal complex, the molar ratio of metal salt to α-acylimine compound can be any ratio capable of producing the α-acylimine metal complex or the α-diimine metal complex. In some embodiments, the molar ratio of metal salt to α-acylimine compound is greater than 0.75:1; alternatively, greater than 0.85:1; alternatively, greater than 0.9:1; or alternatively, greater than 0.95:1. In other embodiments, the molar ratio of metal salt to α-acylimine compound ranges from 0.75:1 to 1.25:1; alternatively, ranges from 0.85:1 to 1.15:1; or alternatively, ranges from 0.9:1 to 1.1:1. In yet other embodiments, the molar ratio of metal salt to α-acylimine compound is about 1:1.

Generally, whenever a primary amine is contacted with an α-acylimine compound, e.g. to form an α-diimine compound or an α-diimine metal complex, the molar ratio of primary amine to α-acylimine compound is any primary amine to α-acylimine compound molar ratio capable of producing the α-diimine compound or the α-diimine metal complex. In some embodiments, the molar ratio of primary amine to α-acylimine compound can be less than 1.25:1; alternatively, less than 1.15 to 1; or alternatively, less than 1.1:1. The molar ratio of primary amine to α-acylimine compound can range from 0.75:1 to 1.25:1; alternatively, range from 0.85:1 to 1.15:1; or alternatively, range from 0.9:1 to 1.1:1. In certain embodiments, the molar ratio of primary amine to α-acylimine compound is about 1:1. In yet other embodiments, the molar ratio of primary amine to α-diimine compound can be greater than 1:1 when the initial imine group is not readily displaced with the primary amine under the reaction conditions employed. In this embodiment, the use of excess primary amine can prove desirable.

Generally, whenever a primary amine, α-acylimine compound, and a metal salt are contacted, e.g. to form an α-diimine metal complex, the molar ratio of primary amine to α-acylimine compound to metal salt to α-acylimine compound is any primary amine to metal salt to α-diacyl compound molar ratio capable of producing the α-diimine metal complex. In some embodiments, the molar ratio of primary amine to metal salt to α-acylimine compound can range from 0.75:1:1 to 1.1:1:1; alternatively, range from 0.85:1:1 to 1.05:1:1; or alternatively, range from 0.9:1:1 to 1.02:1:1. In certain embodiments, the molar ratio of amine to α-acylimine compound to metal salt can be about 1:1:1.

Generally, whenever a primary amine is contacted with an α-acylimine metal complex, e.g. to form an α-diimine metal complex, the molar ratio of primary amine to α-acylimine metal complex can be any primary amine to α-acylimine metal complex molar ratio capable of producing the α-diimine metal complex. In some embodiments, the molar ratio of primary amine to α-acylimine metal complex can be greater than 0.9:1; alternatively, greater than 0.95:1; or alternatively, greater than 0.975:1. In other embodiments, the molar ratio of primary amine to α-acylimine metal complex ranges from 0.9:1 to 1.5:1; alternatively, from 0.95:1 to 1:25:1; or alternatively, from 0.975:1 to 1.1:1. In certain embodiments, the molar ratio of amine to α-acylimine metal complex is about 1:1.

Generally, the solvent for preparing the α-acylimine compound, α-acylimine metal complex, or α-diimine metal complex can be any solvent capable of allowing the selected reagents to react to form the selected compound or metal complex. In embodiments, the solvent can be an alcohol, ether, nitrile or halogenated hydrocarbon. In some embodiments, the solvent can be an alcohol; alternatively, and ether; alternatively, a nitrile; or alternatively, a halogenated hydrocarbon. Generally, the alcohol, ether, nitrile, or halogenated hydrocarbon can be any $C_1$ to $C_{10}$ alcohol, $C_1$ to $C_{10}$ ether, $C_1$ to $C_{10}$ nitrile or $C_1$ to $C_{10}$ halogenated hydrocarbon; or alternatively, any $C_1$ to $C_5$ alcohol, ether, $C_1$ to $C_5$ nitrile, or $C_1$ to $C_5$ halogenated hydrocarbon. In some embodiments, the alcohol solvent can be methanol, ethanol, propanol, isopropanol, butanol, or tert-butanol. In other embodiments, the ether can be dimethyl ether, diethyl ether, methyl ethyl ether, monoethers or diethers of glycols (e.g. dimethyl glycol ether), furans, dihydrofuran, substituted dihydrofurans, tetrahydrofuran (THF), tetrahydropyrans, 1,3-dioxanes, or 1,4-dioxanes. In other embodiments, the nitrile solvent can be acetonitrile. In yet other embodiments, the halogenated hydrocarbon can be methylene chloride, chloroform, carbon tetrachloride, or 1,2-dichloroethane. In some particular embodiments, the solvent can be methanol; alternatively, ethanol; alternatively, isopropanol; alternatively, tetrahydrofuran; alternatively, acetonitrile; alternatively, methylene chloride; or alternatively, chloroform.

Generally, the formation of at least one imine bond of α-diimine metal complex in the presence of a metal salt or metal complex (e.g. reaction between a primary amine and α-acylimine metal complex or a reaction between a primary amine, metal salt and an α-acylimine compound) can be carried out at any suitable reaction conditions capable of producing the α-diimine metal complex. For example, the time, temperature, and/or pressure required to produce the α-diimine metal complex by forming at least one imine bond of α-diimine metal complex in the presence of a metal salt or metal complex can be any condition needed to produce a quantity of the α-diimine metal complex. Provided the teachings of the present disclosure, a skilled artisan may recognize the relationship between parameters, such as the temperature of the imine bond formation reaction and the time necessary to form a quantity of the α-diimine metal complex, and how to suitably vary such parameters. Additionally, provided the teachings of the present disclosure, the skilled artisan may also recognize that an imine bond formation reaction can also be dependent upon other reaction parameters such as molar ratio of reagents, and can vary the reaction parameters such as reagent mole ratio, reaction time, and/or reaction temperature to obtain desired results.

Generally, the formation of at least one imine bond of α-diimine metal complex in the presence of a metal salt or metal complex (e.g. reaction between a primary amine and α-acylimine metal complex or a reaction between a primary amine, metal salt and an α-acylimine compound) can be carried out at any suitable reaction conditions capable of producing the α-diimine metal complex. For example, the time, temperature, and/or pressure required to produce the α-diimine metal complex by forming at least one imine bond of α-diimine metal complex in the presence of a metal salt or metal complex can be any condition needed to produce a quantity of the α-diimine metal complex. Provided the teachings of the present disclosure, a skilled artisan may recognize the relationships between parameters, such as the temperature of the imine bond formation reaction and the time necessary to form a quantity of the α-diimine metal complex, and how to suitably vary such parameters. Additionally, provided the teachings of the present disclosure, the skilled artisan may also recognize that an imine bond formation reaction can also be dependent upon other reaction parameters such as molar ratio of reagents, and can vary the reaction parameters such as reagent mole ratio, reaction time, and/or reaction temperature to obtain desired results.

In some embodiments, the reaction to form at least one imine bond of the α-diimine metal complex in the presence of a metal salt or metal complex can occur at a temperature ranging from −20° C. to 200° C. In other embodiments, the reaction to form at least one imine bond of the α-diimine metal complex in the presence of a metal salt or metal complex can occur at a temperature ranging from 0° C. to 150° C.; alternatively, from 20° C. to 100° C.; or alternatively, from 40° C. to 80° C. The time needed to form at least one imine bond of resulting α-diimine metal complex in the presence of a metal salt or metal complex, at the temperature described herein, may be from less than 1 minute to 48 hours; alternatively, from 30 minutes to 36 hours; or alternatively, from 1 hours to 24 hours. The temperatures and times described herein are generally applicable to any methods of forming at least one imine bond in the presence of a metal salt or metal complex including the methods for contacting an α-diacyl compound, a metal salt and a primary amine, contacting an α-acylimine compound, a metal salt, and a primary amine, or contacting an α-acylimine metal complex and a primary amine.

In embodiments, the step wherein the imine bond of the α-diimine metal complex is formed in the presence of a metal salt or metal complex proceeds at a yield of greater than 60 percent based on the weight of the limiting reagent. In some embodiments, the step wherein the imine bond of the α-diimine metal complex is formed in the presence of a metal salt or metal complex proceeds at a yield of greater than about 65 percent based on the weight of the limiting reagent; alternatively, greater than 70 percent based on the weight of the limiting reagent; alternatively, greater than 75 percent based on the weight of the limiting reagent; alternatively, greater than 80 percent based on the weight of the limiting reagent; alternatively, greater than 85 percent based on the weight of the limiting reagent; or alternatively, greater than 90 percent based on the weight of the limiting reagent.

Generally, the procedures described herein enable the production of specific α-diimine metal complexes having two different (or two different type) imine groups in a high yield using an α-diacyl compound and two different (or two different type) primary amines. Not to be bound by theory, it is believed that the reaction of the second amine with an α-acylimine compound in the presence of a metal salt, or reaction of the second amine with an α-acylimine metal complex, inhibits the reversibility of the Schiff base reaction that formed the first imine group of the α-acylimine compound. Normally, the reversibility of the Schiff base reaction does not create issues when the two primary amines used to produce the two imine group of the α-diimine compound (and ultimately the α-diimine metal complex) are the same. However, when the two different primary amines are used to produce two different imine nitrogen groups, the reversibility of the Schiff base reaction allows the α-acylimine compound to revert into its component primary amine and α-diacyl compound and thus allows the formation of all potential α-diimine compounds. Thus, the presence of the metal salt or α-acylimine metal complex during the formation of α-diimine metal complex allows improved selectivity to a specific desired α-diimine metal complex based upon the limiting reagent of the synthesis method.

In embodiments, α-diimine metal complex is produced at an overall yield of greater than 50 percent based on the weight of the limiting reagent; alternatively, greater than 55 percent based on the weight of the limiting reagent; alternatively, the greater than about 60 percent based on the weight of the limiting reagent; alternaively, greater than 65 percent based on the weight of the limiting reagent; alternatively, greater than 70 percent based on the weight of the limiting reagent; alternatively, greater than 75 percent based on the weight of the limiting reagent; or alternatively, greater than 80 percent based on the weight of the limiting reagent. In some embodiments, the limiting reagent for determination of the overall yield can be the α-diacyl compound. In other embodiments, the limiting reagent for determination of the overall yield is the can be the first primary amine.

Olefin Polymerization or Oligomerization

The α-diimine metal complexes described in the present application can be employed in the polymerization and/or oligomerization of olefins. Such a process can be carried out by contacting a catalyst system comprising an α-diimine metal complex with one or more olefin monomers under reaction conditions suitable for polymerization or oligomerization of olefins. In some embodiments, the polymerization or oligomerization process comprises 1) contacting an olefin, an α-diimine metal complex, and a cocatalyst; and 2) forming an olefin polymer or oligomer. In other embodiments, the polymerization or oligomerization process is an alpha olefin production process comprising: 1) contacting ethylene, an α-diimine metal complex, and a cocatalyst; and 2) forming a product stream comprising alpha olefins. In other embodiments, the polymerization or oligomerization process is an alpha olefin production process comprising: 1) contacting ethylene, an α-diimine metal complex, and a cocatalyst; and 2) forming a product stream comprising polyethylene. The process can comprise additional steps such as deactivating the catalyst and isolating the olefin oligomer or polymer. Suitable monomers for the olefin polymerization or oligomerization can be olefins having 2 to 20 carbon atoms; alternatively, olefins having 2 to 3 carbon atoms; alternatively, ethylene; or alternatively, propylene.

Olefin Polymerization or Oligomerization Catalysts and Cocatalysts

Within the polymerization or oligomerization processes, the α-diimine metal complex can be any α-diimine metal complex described herein capable of forming the desired polymer or oligomer. In embodiments, the α-diimine metal complex can be a metal salt complexed to an α-diimine compound comprising 1) an α-diimine group derived from an α-diacyl compound and 2) two different α-diimine nitrogen groups. In other non-limiting embodiments, the α-diimine metal complex can be a metal salt complexed to an α-diimine compound comprising 1) an α-diimine group derived from an α-diacyl compound and 2) two different α-diimine nitrogen groups consisting of an organyl groups consisting of inert functional groups, hydrocarbyl groups, or mixture thereof; alternatively, a metal salt complexed to an α-diimine compound consisting of 1) an α-diimine group derived from an α-diacyl compound and 2) a first imine nitrogen group consisting of an organyl group consisting of inert functional groups or a hydrocarbyl group and 3) a second imine nitrogen group comprising a metal salt complexing group; or alternatively, a metal salt complexed to an α-diimine compound consisting of 1) an α-diimine group derived from an α-diacyl compound and 2) a first imine nitrogen group consisting an organyl group consisting of inert functional groups or a hydrocarbyl group and 3) a second imine group comprising a metal salt complexing group and a linking group linking the metal salt complexing group to the second imine nitrogen atom. As the metal salt, α-diacyl compound from which the α-diimine compound is derived, and the two imine groups originate from independent elements, the α-diimine metal complex utilized to polymerize or oligomerize olefins can be further described using any combination of the metal salt as described herein, the α-diacyl compound from which the α-diimine compound is derived as described herein, any first imine nitrogen group as described herein, any second imine nitrogen group metal salt complexing group as described herein, and any linking group linking the metal salt complexing group to the of the second imine nitrogen group as described herein. Alternatively, the α-diimine metal complexes utilized for the polymerization or oligomerization of olefins can be described using the alternative α-diimine metal complex descriptions equivalent to the polymerization or oligomerization α-diimine metal complexes indicated herein.

The process to produce alpha olefins can utilize any α-diimine metal complex capable of producing alpha olefins. In non-limiting embodiments, the α-diimine metal complex capable of producing alpha olefins can be a metal salt complexed to an α-diimine compound comprising 1) an α-diimine group derived from an α-diacyl compound and 2) a first imine nitrogen group consisting of an organyl group consisting of inert functional groups or a hydrocarbyl group and 3) a second imine nitrogen group comprising a metal salt complexing group and a linking group linking the metal salt complexing group to the second imine nitrogen atom; or alternatively, a metal salt complexed to an α-diimine compound consisting of 1) an α-diimine group derived from an α-diacyl compound and 2) a first imine nitrogen group consisting of an organyl group consisting of inert functional groups or a hydrocarbyl group and 3) a second imine nitrogen group consisting of a metal salt complexing group and a linking group linking the metal salt complexing group to the second imine nitrogen atom. As the metal salt, α-diacyl compound from which the α-diimine compound is derived, and the two imine groups originate from independent elements, the α-diimine metal complex capable of producing alpha olefins can be further described using any combination of the metal salt as described herein, the α-diacyl compound from which the α-diimine compound is derived as described herein, any first imine nitrogen group as described herein, any second imine nitrogen group metal salt complexing group as described herein, and any linking group linking the metal salt complexing group to the of the second imine nitrogen group as described herein. Alternatively, the α-diimine metal complexes utilized for the production of alpha olefins can be described using the alternative α-diimine metal complex descriptions equivalent to alpha olefin production α-diimine metal complexes indicated herein.

The metal salt of the α-diimine metal complex capable of producing alpha olefins can be any metal salt as described herein. In embodiments, the metal salt can comprise iron, cobalt, or mixtures thereof. In some embodiments, the metal salt can comprise iron or cobalt. In some embodiments, the metal salt can comprise iron; or alternatively, comprise cobalt.

The α-diacyl compound from which the α-diimine group of the α-diimine metal complex capable of producing alpha olefins is derived can be any α-diacyl compound as described herein. In embodiments, the α-diimine group can be derived from an aromatic α-diacyl compound. In some embodiments, the α-diimine group of the α-diimine metal complex can be derived from acenaphthenequinone, a substituted acenaphthenequinone, phenanthrenequinone, a substituted phenanthrenequinone, pyrenequinone, or a substituted pyrenequinone. In other embodiments, the α-diimine group of the α-diimine metal complex can be derived from acenaphthenequinone, phenanthrenequinone, or pyrenequinone. In yet other embodiments, the α-diimine group of the α-diimine metal complex can be derived from acenaphthenequinone; alternatively, phenanthrenequinone; or alternatively, pyrenequinone.

The first imine nitrogen group within the α-diimine group of some α-diimine metal complexes capable of producing alpha olefins can be any organyl group consisting of inert functional groups or a hydrocarbyl group as described herein. In an aspect, the organyl group consisting of inert functional groups of the first imine nitrogen group can consist of a phenyl group or a substituted phenyl group (substituted phenyl group consisting of inert functional groups). In embodiments, the hydrocarbyl group of the first imine nitrogen group can consist of a phenyl group or a substituted phenyl group. In some embodiments, the hydrocarbyl group of the first imine nitrogen group can be a 2-substituted phenyl group; alternatively, a 2,6-disubstituted phenyl group; or alternatively, a 2,4,6-trisubstituted phenyl group. In other embodiments, the hydrocarbyl group of the first imine nitrogen group can be a 2,6-dimethylphenyl group, a 2,6-diethylphenyl group, a 2,6-diisopropylphenyl group, or a 2,6-di-tert-butylphenyl group. In yet other embodiments, the hydrocarbyl group of the first imine nitrogen group can be a 2,6-dimethylphenyl group, a 2,6-diethylphenyl group, or a 2,6-diisopropylphenyl group. In further embodiments, the hydrocarbyl group of the first imine nitrogen group can be a 2,6-dimethylphenyl group; alternatively, a 2,6-diethylphenyl group; alternatively, a 2,6-diisopropylphenyl group; alternatively, a 2,6-di-tert-butylphenyl group; or alternatively, a 2,4,6-trimethylphenyl group (mesityl group).

Particular combinations of the metal salt complexing group and linking group linking the metal salt complexing group to the second imine nitrogen atom within the α-diimine compound of the α-diimine metal complex can be advantageous for producing alpha olefins. In aspects, the second imine group can comprise a dialkyl aminyl group, a diphenyl aminyl group, a substituted diphenyl aminyl group a dialkyl phosphinyl group, a diphenyl phosphinyl group, or a substituted diphenyl phosphinyl group and $—(CH_2)_m—$ linking group where m is 2 or 3; alternatively, can comprise a pyridinyl group, a substituted pyridinyl group, a furanyl group, a substituted furanyl group, a thiophenyl group, or a substituted thiophenyl group and a $—(CH_2)—$ linking group; or alternatively, can comprise an alkyl etheryl group, a phenyl etheryl group, a substituted phenyl etheryl group, an alkyl sulfidyl group, a phenyl sulfidyl group, or a substituted phenyl sulfidyl group and a $—(CH_2CH_2)—$ linking group. Alternatively, the second imine nitrogen group can comprise a dialkyl aminyl group, a diphenyl aminyl group, a dialkyl phosphinyl group, or a diphenyl phosphinyl group and a $—(CH_2)_m—$ linking group where m is 2 or 3; alternatively, can comprise a pyridinyl group, a furanyl group, or a thiophenyl group and a $—(CH_2)—$ linking group; alternatively, can comprise an alkyl etheryl group or an alkyl sulfidyl group and a $—(CH_2CH_2)—$ linking group; or alternatively, can comprise a phenyl etheryl group or an phenyl sulfidyl group and a $—(CH_2CH_2)—$ linking group. In some embodiments, the second imine group can comprise a diphenyl aminyl group, a substituted diphenyl aminyl group, a diphenyl phosphinyl group, or substituted a diphenyl phosphinyl group and a $—(CH_2)_m—$ linking group where m is 2 or 3; alternatively, can comprise a diphenyl aminyl group or a diphenyl phosphinyl group and a $—(CH_2)_m—$ linking group where m is 2 or 3; alternatively, can comprise a substituted diphenyl aminyl group, or a substituted diphenyl phosphinyl group and a $—(CH_2)_m—$ linking group where m is 2 or 3; alternatively, can comprise a diphenyl phosphinyl group or a substituted diphenyl phosphinyl group and a $—(CH_2)_m—$ linking group where m is 2 or 3; alternatively, can comprise a diphenyl phosphinyl group and a $—(CH_2)_m—$ linking group where m is 2 or 3; alternatively, can comprise a substituted diphenyl phosphinyl group and a $—(CH_2)_m—$ linking group where m is 2 or 3; alternatively, can comprise a diphenyl phosphinyl group or a substituted diphenyl phosphinyl group and a $—(CH_2CH_2)—$ linking group; alternatively, can comprise a diphenyl phosphinyl group and a $—(CH_2CH_2)—$ linking group; alternatively, can comprise a substituted diphenyl phosphinyl group and a $—(CH_2CH_2)—$ linking group; alternatively, can comprise a 2-pyridinyl group or a substituted 2-pyridinyl group and a $—(CH_2)—$ linking group; alternatively, a 2-pyridinyl group and a $—(CH_2)—$ linking group; alternatively, a substituted 2-pyridinyl group and a $—(CH_2)—$ linking group; alternatively, can comprise a phenyl etheryl group, a substituted phenyl etheryl group, a phenyl sulfidyl group, or a substituted phenyl sulfidyl group and a $—(CH_2CH_2)—$ linking group; alternatively, can comprise a phenyl etheryl group, or a phenyl sulfidyl group and a $—(CH_2CH_2)—$ linking group; alternatively, can comprise a substituted phenyl etheryl group, or a substituted phenyl sulfidyl group and a $—(CH_2CH_2)—$ linking group; alternatively, can comprise a phenyl sulfidyl group or a substituted phenyl sulfidyl group and a $—(CH_2CH_2)—$ linking group; alternatively, can comprise a phenyl sulfidyl group and a $—(CH_2CH_2)—$ linking group; or alternatively, can comprise a substituted phenyl sulfidyl group and a $—(CH_2CH_2)—$ linking group.

In other aspects, the second imine group can consist of a dialkyl aminyl group, a diphenyl aminyl group, a substituted diphenyl aminyl group a dialkyl phosphinyl group, a diphenyl phosphinyl group, or a substituted diphenyl phosphinyl group and $—(CH_2)_m—$ linking group where m is 2 or 3; alternatively, can consist of a pyridinyl group, a substituted pyridinyl group, a furanyl group, a substituted furanyl group, a thiophenyl group, or a substituted thiophenyl group and a $—(CH_2)—$ linking group; or alternatively, can consist of an alkyl etheryl group, a phenyl etheryl group, a substituted phenyl etheryl group, an alkyl sulfidyl group, a phenyl sulfidyl group, or a substituted phenyl sulfidyl group and a $—(CH_2CH_2)—$ linking group. Alternatively, the second imine nitrogen group can consist of a dialkyl aminyl group, a diphenyl aminyl group, a dialkyl phosphinyl group, or a diphenyl phosphinyl group and a $—(CH_2)_m—$ linking group where m is 2 or 3; alternatively, can consist of a pyridinyl group, a furanyl group, or a thiophenyl group and a $—(CH_2)—$ linking group; alternatively, can consist of an alkyl etheryl group or an alkyl sulfidyl group and a $—(CH_2CH_2)—$ linking group; or alternatively, can consist of a phenyl etheryl group or an phenyl sulfidyl group and a $—(CH_2CH_2)—$ linking group. In some embodiments, the second imine group can consist of a diphenyl aminyl group, a substituted diphenyl aminyl group, a diphenyl phosphinyl group, or substituted a diphenyl phosphinyl group and a $—(CH_2)_m—$ linking group where m is 2 or 3; alternatively, can consist of a diphenyl aminyl group or a diphenyl phosphinyl group and a $—(CH_2)_m—$ linking group where m is 2 or 3; alternatively, can consist of a substituted diphenyl aminyl group, or a substituted diphenyl phosphinyl group and a $—(CH_2)_m—$ linking group where m is 2 or 3; alternatively, can consist of a diphenyl phosphinyl group or a substituted diphenyl phosphinyl group and a $—(CH_2)_m—$ linking group where m is 2 or 3; alternatively, can consist of a diphenyl phosphinyl group and a $—(CH_2)_m—$ linking group where m is 2 or 3; alternatively, can consist of a substituted diphenyl phosphinyl group and a $—(CH_2)_m—$ linking group where m is 2 or 3; alternatively, can consist of a diphenyl phosphinyl group or a substituted diphenyl phosphinyl group and a $—(CH_2CH_2)—$ linking group; alternatively, can consist of a diphenyl phosphinyl group and a $—(CH_2CH_2)—$ linking group; alternatively, can consist of a substituted diphenyl phosphinyl group and a $—(CH_2CH_2)—$ linking group; alternatively, can consist of a 2-pyridinyl group or a substituted 2-pyridinyl group and a $—(CH_2)—$ linking group; alternatively, a 2-pyridinyl group and a $—(CH_2)—$ linking group; alternatively, a substituted 2-pyridinyl group and a $—(CH_2)—$ linking group; alternatively, can consist of a phenyl etheryl group, a substituted phenyl etheryl group, a phenyl sulfidyl group, or a substituted phenyl sulfidyl group and a $—(CH_2CH_2)—$ linking group; alternatively, can consist of a phenyl etheryl group, or a phenyl sulfidyl group and a $—(CH_2CH_2)—$ linking group; alternatively, can consist of a substituted phenyl etheryl group, or a substituted phenyl sulfidyl group and a $—(CH_2CH_2)—$ linking group; alternatively, can consist of a phenyl sulfidyl group or a substituted phenyl sulfidyl group and a $—(CH_2CH_2)—$ linking group; alternatively, can consist of a phenyl sulfidyl group and a $—(CH_2CH_2)—$ linking group; or alternatively, can consist of a substituted phenyl sulfidyl group and a $—(CH_2CH_2)—$ linking group.

In a non-limiting aspect, the α-diimine metal complex capable of producing alpha olefins can comprise a metal salt comprising iron complexed to an α-diimine compound comprising 1) an α-diimine group derived from aromatic dione; 2) a first imine nitrogen group consisting of a 2,6-disubstituted phenyl group; and 3) a second imine nitrogen group comprising a metal salt complexing group and a linking group linking the metal salt complexing group to the second imine nitrogen atom; or alternatively, a metal salt comprising iron complexed to an α-diimine compound comprising 1) an α-diimine group derived from aromatic dione; 2) a first imine nitrogen group consisting of a 2,6-disubstituted phenyl group; and 3) a second imine nitrogen group consisting of a metal salt complexing group and a linking group linking the metal salt complexing group to the second imine nitrogen atom. In some non-limiting embodiments, the α-diimine metal complex capable of producing alpha olefins can comprise a metal salt comprising iron complexed to an α-diimine compound comprising 1) an α-diimine group derived from acenaphthenequinone, phenanthrenequinone, or pyrenequinone; 2) a first imine nitrogen group consisting of a 2,6-dimethylphenyl group, a 2,6-diethylphenyl group, or a 2,6-diisopropylphenyl group; and 3) a second imine nitrogen group comprising a metal salt complexing group and a linking group linking the metal salt complexing group to the second imine nitrogen atom. In other non-limiting embodiments, the α-diimine metal complex capable of producing alpha olefins can comprise a metal salt comprising iron complexed to an α-diimine compound comprising 1) an α-diimine group derived from acenaphthenequinone, phenanthrenequinone, or pyrenequinone; 2) a first imine nitrogen group consisting of a 2,6-dimethylphenyl group, a 2,6-diethylphenyl group, or a 2,6-diisopropylphenyl group; and 3) a second imine nitrogen group consisting of a metal salt complexing group and a linking group linking the metal salt complexing group to the second imine nitrogen atom. Further embodiments of the elements of the α-diimine metal complex capable of producing alpha olefins are described herein.

Generally, the cocatalyst can be any organometallic compound capable of activating the α-diimine metal complex to polymerize or oligomerize olefins. Suitable cocatalysts can include monomeric or oligomeric metal alkyls, metal aryls, metal alkyl-aryls comprising at least one of the metals selected from the group consisting of B, Al, Be, Mg, Ca, Sr, Ba, Li, Na, K, Rb, Cs, Zn, Cd, and Sn. In embodiments, the cocatalyst can be selected from the group consisting of organoaluminum compounds, organoboron compounds, organolithium compounds, or mixtures thereof. In some embodiments, the cocatalyst can be an organoaluminum compound. Applicable organoaluminum compounds can include trialkylaluminums, alkylaluminum halides, alumoxanes or mixture thereof. In some embodiments, the organoaluminum compound can be trimethylaluminum triethylaluminum, diethylaluminum chloride, diethylaluminum ethoxide, diethylaluminum cyanide, diisobutylaluminum chloride, triisobutylaluminum, ethylaluminum sesquichloride, methylalumoxane (MAO), modified methylalumoxane (MMAO), isobutyl alumoxanes, t-butyl alumoxanes, or mixtures thereof. In other embodiments, the organoaluminum compounds can include methylalumoxane (MAO), modified methylalumoxane (MMAO), isobutyl alumoxanes, t-butyl alumoxanes, or mixtures thereof. In other embodiments, the cocatalyst can be methylalumoxane, modified methylalumoxane, or mixtures thereof. In yet other embodiments, the cocatalyst can be methylalumoxane; alternatively, modified methylalumoxarne; isobutylalumoxane (IBAO); or alternatively, partially hydrolyzed trialkylaluminum.

In embodiments, the molar ratio of the metal of the cocatalyst to the metal of the α-diimine metal complex can range from 1:1 to 10,000:1; alternatively, from 10:1 to 5,000:1; or alternatively, from 100:1 to 3,000:1; or alternatively, from 200:1 to 2,000:1. In embodiments wherein the α-diimine metal complex comprises a iron salt and the cocatalyst is an alumoxane the molar ratio of aluminum to iron can range from 1:1 to 10,000:1; alternatively, from 10:1 to 5,000:1; alternatively, from 100:1 to 3,000:1; or alternatively, from 200:1 to 2,000:1.

The α-diimine metal complex, cocatalyst(s), and olefin can be contacted in any manner known to those skilled in the art. For instance, the α-diimine metal complex and the cocatalyst can be mixed first before bringing into contact with a feed comprising an olefin or an olefin mixture. Alternatively, the cocatalyst can be mixed with the olefin and/or the solvent prior to contact with the α-diimine metal complex.

Polymerization or Oligomerization Solvents, Reactors, Reaction Conditions and Products In embodiments, the polymerization or oligomerization reaction can occur in a solvent or diluent. In some embodiments, the solvent or diluent can comprise a $C_4$ to $C_{20}$ hydrocarbon; or alternatively, a $C_4$ to $C_{10}$ hydrocarbon. The hydrocarbon solvent can be a saturated hydrocarbon, an aromatic hydrocarbon or an olefinic hydrocarbon. In some embodiments, the saturated hydrocarbon solvent can be a $C_4$ to $C_{10}$ saturated hydrocarbon. In other embodiments, the saturated solvent can be butane, isobutane, hexane, heptane, cyclohexane, or mixtures thereof. In some embodiments, the aromatic solvent can be a $C_6$ to $C_{20}$ aromatic compound. In some embodiments, the aromatic solvent can be benzene, toluene, xylene(s), ethylbenzene, or mixtures thereof. In other embodiments, another embodiment, the olefinic hydrocarbon solvent can comprise alpha olefins. In other embodiments, the alpha olefin solvent comprises a $C_4$ to $C_{20}$ alpha olefin; alternatively, a $C_4$ to $C_{12}$ alpha olefin; alternatively, alternatively, a $C_{12}$ to $C_{18}$ alpha olefin. In yet other embodiments, the alpha olefin solvent can be 1-butene, 1-dodecene, 1-tetradecene, 1-hexadecene, 1-octadecene, or combinations thereof.

Unless specified otherwise, the terms contacted, combined, and "in the presence of" refer to any addition sequence, order, or concentration for contacting or combining two or more components of the polymerization reaction. Combining or contacting of polymerization or oligomerization components, according to the various methods described herein may occur in one or more contact zones under suitable contact conditions such as temperature, pressure, contact time, flow rates, etc. . . . The contact zone can be disposed in a vessel, e.g. a storage tank, tote, container, mixing vessel, reactor, etc.; a length of pipe, e.g. a tee, inlet, injection port, or header for combining component feed lines into a common line; or any other suitable apparatus for bringing the components into contact. The methods may be carried out in a batch or continuous process as is suitable for a given embodiment, with physical parameters of the contact zone being specified accordingly.

In embodiments, the polymerization or oligomerization can be a continuous process carried out in one or more reactors. In some embodiments, the continuous polymerization or oligomerization process reactor can comprise a loop reactor, a tubular reactor, a continuous stirred tank reactor (CSTR), or combinations thereof. In other embodiments, the continuous polymerization or oligomerization process reactor can be a loop reactor; alternatively, a tubular reactor; or alternatively, a continuous stirred tank reactor (CSTR). In other embodiments, the continuous polymerization or oligomerization process reactor can be employed in the form of different types of continuous reactors in combination, and in various arrangements. In an embodiment, the continuous reactor can be a combination of a tubular reactor and a CSTR. In other embodiments, the continuous polymerization or oligomerization process reactor can be two or more reactors in series, two or more reactors in parallel, or combinations thereof. In an embodiment, the continuous polymerization or oligomerization process reactor can be more than one CSTR in series. In another embodiment, the continuous reactor can be a tubular reactor and a loop reactor in series. In yet another embodiment, the continuous reactor can be two or more loop reactors in series.

Suitable polymerization or oligomerization reaction conditions such as temperatures, pressures and times can be impacted by a number of factors such as α-diimine metal complex identity, α-diimine metal complex stability, α-diimine metal complex activity, cocatalyst identity, cocatalyst activity, desired product (e.g. polyethylene versus alpha olefins), desired product distribution, and/or desired product purity among others. Provided the teachings of the present disclosure, one skilled in the art will recognize how to adjust the polymerization or oligomerization reaction conditions to achieve the desired objectives.

The reaction temperature of the polymerization or oligomerization reaction can be any reaction temperature required to produce the desired polymerization or oligomerization product (such as polyethylene or alpha olefins). In some embodiments, the reaction temperature for the polymerization or oligomerization reaction can range from −20° C. to 200° C. In some embodiments, the polymerization or oligomerization temperature ranges from 0° C. to 150° C.;

alternatively, ranges from 10° C. to 150° C.; alternatively, ranges from 20° C. to 100° C.; or alternatively, ranges from 30° C. to 80° C.

The reaction pressure of the polymerization or oligomerization reaction can be any reaction pressure required to produce the desired polymerization or oligomerization product (such as polyethylene or alpha olefins). In some embodiments, the polymerization or oligomerization reaction pressure can be greater than 0 psig (0 KPa); alternatively, greater than 50 psig (344 KPa); alternatively, greater than 100 psig (689 KPa); or alternatively, greater than 150 psig (1.0 MPa). In other embodiments, the polymerization or oligomerization reaction pressure can range from 0 psig (0 KPa) to 5,000 psig (34.5 MPa); alternatively, 50 psig (344 KPa) to 4,000 psig (27.6 MPa); alternatively, 100 psig (689 KPa) to 3,000 psig (20.9 MPa); or alternatively, 150 psig (1.0 MPa) to 2,000 psig (13.8 MPa). In embodiments wherein the monomer is a gas (e.g. ethylene), the polymerization or oligomerization reaction can be carried out under a monomer gas pressure. When the polymerization or oligomerization reaction produces polyethylene or alpha olefins, the reaction pressure can be the monomer ethylene pressure. In some embodiments, the ethylene pressure can be greater than 0 psig (0 KPa); alternatively, greater than 50 psig (344 KPa); alternatively, greater than 100 psig (689 KPa); or alternatively, greater than 150 psig (1.0 MPa). In other embodiments, the ethylene pressure can range from 0 psig (0 KPa) to 5,000 psig (34.5 MPa); alternatively, 50 psig (344 KPa) to 4,000 psig (27.6 MPa); alternatively, 100 psig (689 KPa) to 3,000 psig (20.9 MPa); or alternatively, 150 psig (1.0 MPa) to 2,000 psig (13.8 MPa). In some cases when ethylene is the monomer, inert gases can form a portion of the total reaction pressure. In the cases where inert gases form a portion of the reaction pressure, the previously stated ethylene pressures can be the applicable ethylene partial pressures of the polymerization or oligomerization reaction. In the situation where the monomer provides all or a portion of the polymerization or oligomerization reaction pressure, the reaction system pressure can decrease as the gaseous monomer is consumed. In this situation, additional gaseous monomer and/or inert gas can be added to maintain a desired polymerization or oligomerization reaction pressure. In embodiments, additional gaseous monomer can be added to the polymerization or oligomerization reaction at a set rate (e.g. for a continuous flow reactor), at different rates (e.g. to maintain a set system pressure in a batch reactor). In other embodiments, the polymerization or oligomerization reaction pressure can be allowed to decrease without adding any additional gaseous monomer and/or inert gas.

The reaction time of the polymerization or oligomerization reaction can be any reaction time required to produce the desired quantity of polymerization or oligomerization product (such as polyethylene or alpha olefins), obtain a desired catalyst productivity, and/or obtain a desired conversion of monomer. In some embodiments, the polymerization or oligomerization reaction time ranges from 1 minute to 5 hours; alternatively, ranges from 5 minutes to 2.5 hours; alternatively, ranges from 10 minutes to 2 hours; or alternatively, ranges from 1 minute to 1.5 hours.

In an embodiment, the oligomerization produces alpha olefins having at least four carbon atoms. In further embodiments, the oligomerization to produce alpha olefins having at least four carbon atoms can be characterized by a single pass conversion of ethylene of at least about 35 weight percent; alternatively, at least 45 percent; alternatively, at least 50 percent; alternatively, at least 55 percent; alternatively, at least 60 percent.

In an aspect, the oligomerization process utilizing the α-diimine metal complex can produce alpha olefins. In some embodiments, the product comprises linear alpha olefin having at least 4 carbon atoms. Generally, the oligomerization process producing alpha olefins having at least four carbon atoms produces a distribution of several alpha olefins that can be described by a Schulz-Flory chain growth factor K, where K is defined by the equation:

$$K=X_{q+2}/X_n$$

wherein $X_{q+2}$ is the number of moles of alpha olefin produced having q+2 carbon atoms and $X_q$ is the number of moles of alpha olefin produced having n carbon atoms (i.e. the moles of the preceding alpha olefin produced). In some embodiments, the alpha olefin product distribution can be described as having a Schulz-Flory chain growth factor K less than 0.95; alternatively, less than 0.9; alternatively, less than 0.9; or alternatively, less than 0.80. In other embodiments, the alpha olefin product distribution can be described as having a Schulz-Flory chain growth factor K range from 0.4 to 0.95; alternatively, from 0.45 to 0.9; alternatively, from 0.5 to 0.85; or alternatively, from 0.55 to 0.8. Generally, the Schulz-Flory growth factor can be measured using the number of moles alpha olefins of any two adjacent produced alpha olefins. One skilled in the art will recognize that the measured Schulz-Flory growth factor may not be exactly the same using the number of moles of alpha olefin produced for every possible adjacent pair of produced alpha olefins. Thus, in some embodiments, the Schulz-Flory growth factor can be an average of two or more adjacent pairs of produced alpha olefins.

In another aspect, the oligomerization process can produce an alpha olefin product with high selectivity to linear alpha olefins. In some embodiments, the oligomerization process produces, a reactor effluent wherein the oligomerized product having 6 carbon atoms has a 1-hexene content of greater than 99.0 weight %; alternatively, greater than 99.25 weight %; alternatively, greater than 99.5 weight %; or alternatively, greater than 99.75 weight %. In other embodiments, the oligomerization process produces a reactor effluent wherein the oligomerized product having 8 carbon atoms a 1-octene content of greater than 98.0 weight %; alternatively, greater than 98.5 weight %; alternatively, greater than 99.0 weight %; or alternatively, greater than 99.5 weight %. In yet other embodiments, the oligomerization process produces a reactor effluent wherein the oligomerized product having 10 carbon atoms a 1-decene content of greater than 97.0 weight %; alternatively, greater than 97.5 weight %; alternatively, greater than 98.0 weight %; alternatively, greater than 98.5 weight %; or alternatively, greater than 99.0 weight %. In yet other embodiments, the oligomerization process produces a reactor effluent wherein the oligomerized product having 6 carbon atoms comprises any weight percent 1-hexene as described herein, the oligomerized product having 8 carbon atoms comprises any weight percent 1-octene as described herein, and the oligomerized product having 10 carbon atoms comprises any weight percent 1-decene as described herein. For example, in embodiments, the oligomerization process produces a reactor effluent wherein the oligomerized product having 6 carbon atoms comprises greater than 99.0 weight percent 1-hexene, the oligomerized product having 8 carbon atoms comprises greater than 99.0 weight percent 1-octene, and the oligomerized product having 10 carbon atoms comprises greater than 99 weight percent 1-decene.

EXAMPLES

The data and descriptions provided in the following examples are given to show particular embodiments of the catalysts and methods disclosed, and to demonstrate a number of the practices and advantages thereof. The examples are given as a more detailed demonstration of some of the embodiments described above, and are not intended to limit the specification or the claims to follow in any manner. Table 8 provides the Structures of the compounds and metal complexes of examples 1-9.

TABLE 8

| Compounds of Examples 1-9 |
|---|
| 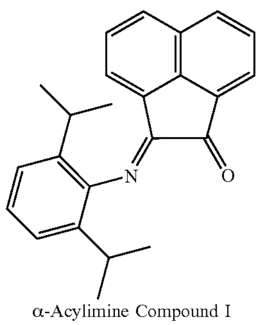 |
| α-Acylimine Compound I |
| 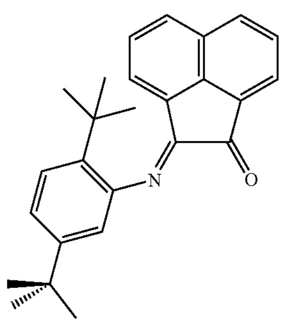 |
| α-Acylimine Compound II |
| 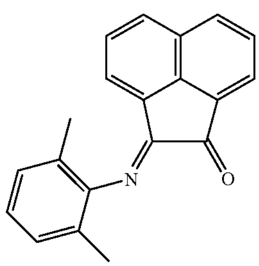 |
| α-Acylimine Compound III |
| 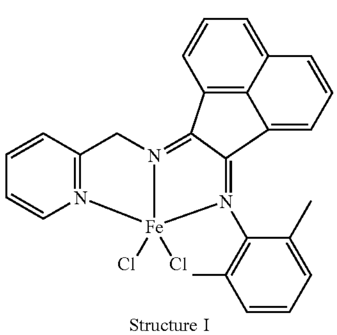 |
| Structure I |

TABLE 8-continued

| Compounds of Examples 1-9 |
|---|
| 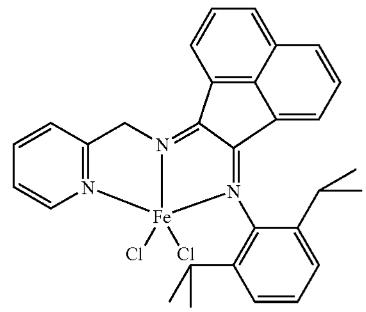 |
| Structure II |
| 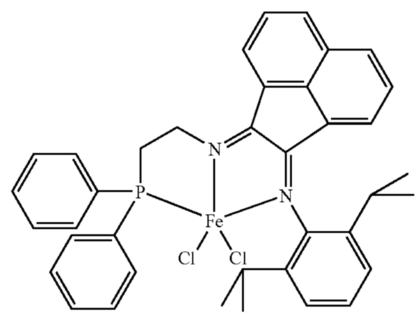 |
| Structure III |
| 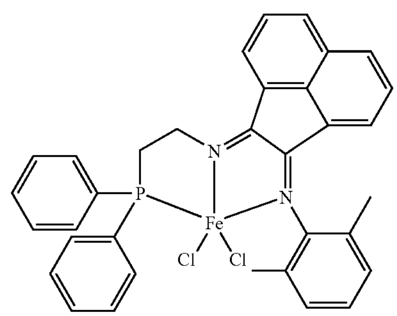 |
| Structure IV |
| 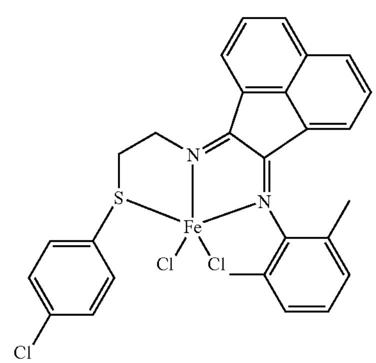 |
| Structure V |

TABLE 8-continued
| Compounds of Examples 1-9 |
| --- |
| 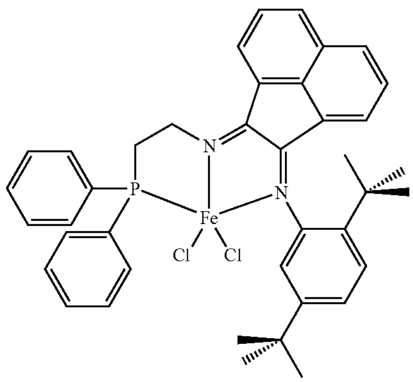 |
| Structure VI |
| 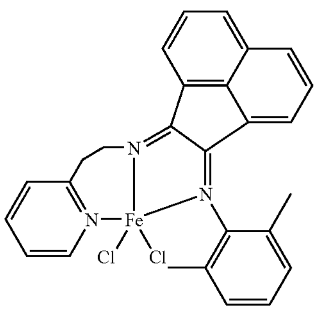 |
| Structure VII |
| 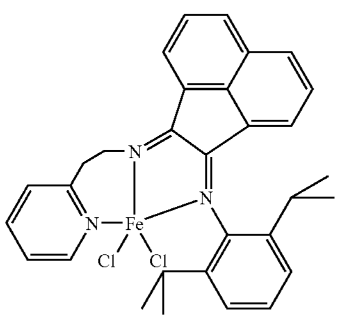 |
| Structure VIII |
| 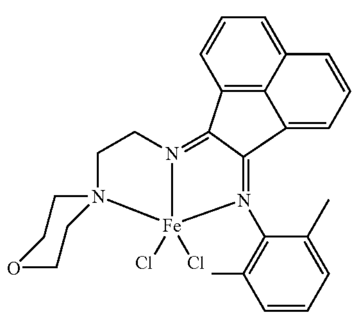 |
| Structure IX |
TABLE 8-continued
| Compounds of Examples 1-9 |
| --- |
| 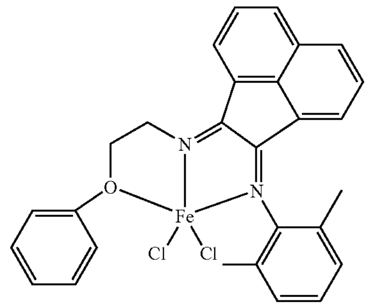 |
| Structure X |
| 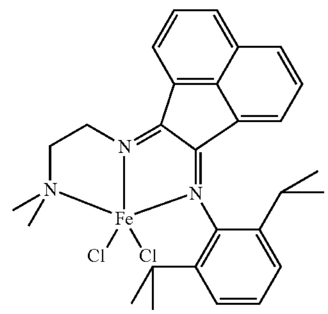 |
| Structure XI |
| 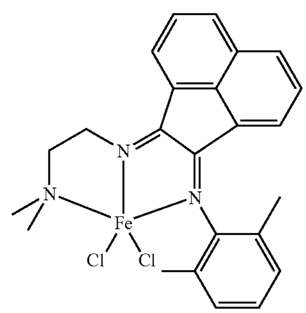 |
| Structure XII |
| 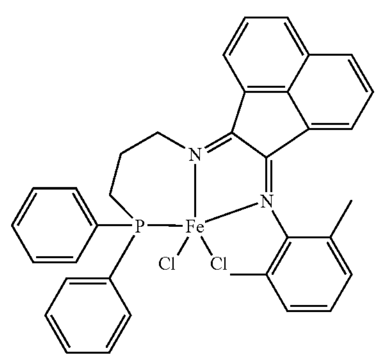 |
| Structure XIII |

TABLE 8-continued

Compounds of Examples 1-9

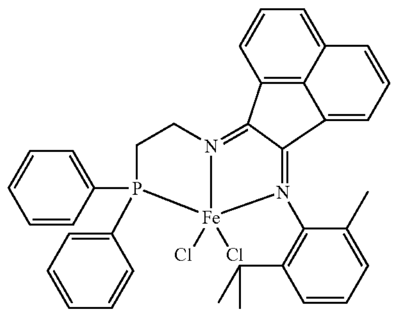
Structure XIV

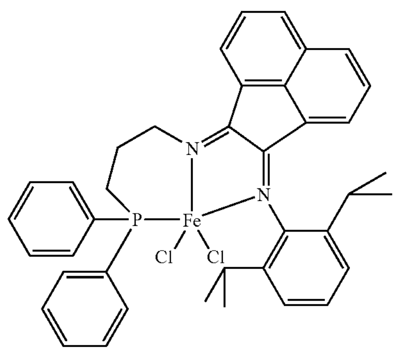
Structure XV

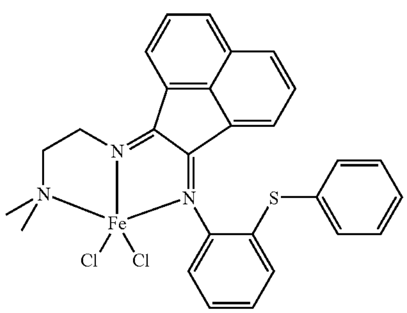
Structure XVI

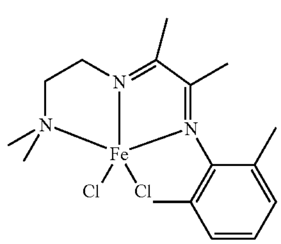
Structure XVII

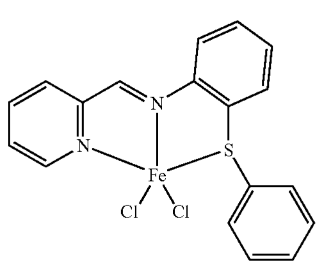
Structure XVIII

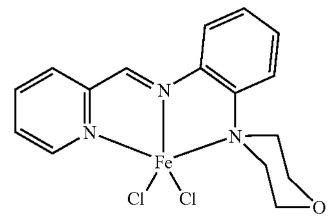
Structure XIX

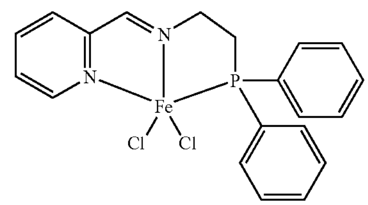
Structure XX

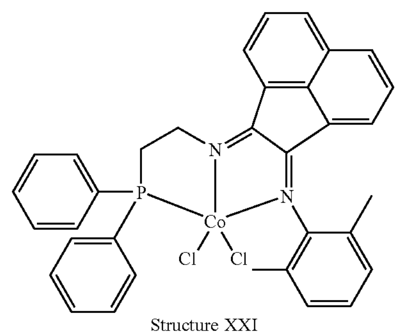
Structure XXI

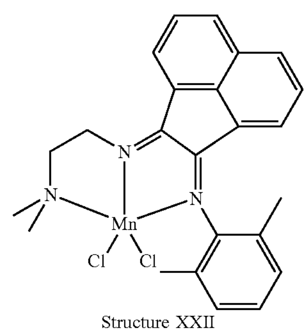
Structure XXII

Example 1

Synthesis of α-Acylimine Compound I ((2E)-2-[(2,6-diisopropylphenyl)imino]acenaphthylen-1(2H)-one)

An ethanol (65 mL) solution of acenaphthenequinone (2.00 g, 11.0 mmol) was treated with 1 mL of formic acid, followed by slow, dropwise addition (over approx. 8 hrs) of a solution of 2,6-diusopropylaniline (1.56 mL, 8.22 mmol) in 65 mL of ethanol. The resulting mixture was stirred at 60° C. overnight, cooled and filtered to remove unreacted acenaphthenequinone. After removal of solvent under vacuum, the resulting orange solid was dissolved in ether, filtered and cooled to −10° C. overnight. The orange solid that deposited was filtered, washed with cold ether and dried. The filtrate was again cooled to −10° C. overnight and additional orange solid was isolated, giving a total yield of 1.91 g (68.5%). Characterized by $^1$H NMR (400 MHz, $CDCl_3$): 0.88 d, 6H; 1.15, d, 6H; 2.82, m, 2H; 8.18, t, 1H; 7.99, d, 1H; 7.81, t, 1H; 7.39, t, 1H; 6.62, d, 1H. (3H's are obscured by the $CDCl_3$ peak). $^1$H NMR (400 MHz, MeCN-$d_3$): 0.89 d, 6H; 1.10, d, 6H; 2.79, m, 2H; 8.27, d, 1H; 8.12, m, 2H; 7.87, t, 1H; 7.45, t, 1H; 7.30, m, 3H; 6.60, d, 1H.

Example 2

Synthesis of α-Acylimine Compound II ((2E)-2-[(2,5-di-t-butylphenyl)imino]acenaphthylen-1(2H)-one)

An ethanol (65 mL) solution of acenaphthenequinone (2.00 g, 11.0 mmol) was treated with 1 mL of formic acid, followed by slow, dropwise addition (over approx. 8 hrs) of a solution of 2,5-di-t-buytlaniline (1.69 g, 8.25 mmol) in 65 mL of ethanol. The resulting mixture was stirred at 60° C. overnight, cooled and filtered to remove unreacted acenaphthenequinone. After removal of solvent under vacuum, the resulting orange solid was dissolved in ether, filtered and cooled to −10° C. overnight. The orange solid that deposited was filtered, washed with cold ether and dried. The filtrate was again cooled to −10° C. overnight and more orange solid was isolated, giving a total yield of 2.13 g (70%). Characterized by $^1$H NMR (400 MHz, $CDCl_3$): 1.24, s, 9H; 1.31, s, 9H; 6.80, s, 1H; 6.88, d, 1H; 7.23, d, 1H (resonance partially covered by $CDCl_3$ peak); 7.40, t, 1H; 7.44, d, 1H; 7.81, t, 1H; 7.97, d, 1H; 8.17, d, 2H.

Example 3

Synthesis of the α-Diimine Metal Complex Having Structure I

A solution containing 0.10 mL (1.0 mmol) of 2-aminomethylpyridine in 50 mL of anhydrous butanol was added via cannula to 0.285 g (1.0 mmol) of α-acylimine compound III and 0.127 g (1.0 mmol) of anhydrous $FeCl_2$. The initially orange solution turned dark brown within 5 minutes and deposited a dark green solid after stirring overnight under argon at 55° C. The solid was filtered, washed with 6 mL of THF, and dried to yield 0.242 g (60%) of dark green product.

Example 4

Synthesis of the α-Diimine Metal Complex Having Structure II

A solution containing 0.10 mL (1.0 mmol) of 2-aminomethylpyridine in 50 mL of anhydrous butanol was added via cannula to 0.342 g (0.91 mmol) of α-acylimine compound I and 0.127 g (1.0 mmol) of anhydrous $FeCl_2$. The initially orange solution turned dark green within 20 min and deposited a dark green solid after stirring overnight under argon at 55° C. The solid was filtered, washed with 6 mL of THF, and dried to yield 0.449 g (80%) of dark green product.

Example 5

Synthesis of the α-Diimine Metal Complex Having Structure III

A solution of 0.297 g (1.3 mmol) of 2-(diphenylphosphino)ethylamine in 40 mL of anhydrous butanol was added via cannula to 0.440 g (1.30 mmol) of (α-acylimine compound I and 0.164 g (1.3 mmol) of anhydrous $FeCl_2$. The solution was stirred overnight under argon at 55° C. The solid that formed was filtered, washed with a small amount of THF, and dried to give 0.505 g (58%) of dark green product. Recrystallization from acetonitrile yielded x-ray quality crystals. The obtained crystals were subjected to x-ray crystallography. An ORTEP diagram for the crystals produced in this example is shown in FIG. 1. Selected bond distance and bond angle for catalyst BMS-114 include: Fe—Cl1-2.286; Fe—Cl2-2.313; Fe—N1-2.181; Fe—N2-2.166; Fe—P1-2.497; P1-Fe—N2-135.19; P1-Fe—Cl1-100.77; N2-Fe—Cl1-93.70; N1-Fe—Cl1-156.18; Cl1-Fe—Cl2-111.98.

Example 6

Synthesis of the α-Diimine Metal Complex Having Structure IV

A solution of 0.211 g (0.92 mmol) of 2-(diphenylphosphino)ethylamine in 40 mL of anhydrous butanol was added via cannula to 0.263 g (0.92 mmol) of α-acylimine compound III and 0.117 g (0.92 mmol) of anhydrous $FeCl_2$. The solution was stirred overnight under argon at 55° C. The solid that formed was filtered, washed with a small amount of THF, and dried to give 0.380 g (66%) of dark green product.

Example 7

Synthesis of the α-Diimine Metal Complex Having Structure V

A 0.202 g sample of 2-aminoethyl(4-chlorophenyl) sulfide (0.93 mmol, 80% pure) was purged with argon for 20 min and then added by cannula to 40 mL of anhydrous butanol. This solution was transferred by cannula to 0.265 g (0.93 mmol) of α-acylimine compound III and 0.118 g (0.93 mmol) of anhydrous $FeCl_2$. The resulting solution was stirred for two days under argon at 55° C. The dark solid that formed was filtered, washed with a small amount of THF, and dried to give 0.203 g (39%) of green product. Recrystallization from acetonitrile gave long, rod-like crystals. The obtained crystals were subjected to x-ray crystallography. An ORTEP diagram for the crystal produced in this example is shown in FIG. 2. Selected bond distance and bond angle for the crystals include: Fe(1)-N(1)=2.132 A; Fe(1)-N(2)=2.197 A. The X-ray crystal structure for the material and the ethylene oligomerization example provided in Table 9 indicate that it is not required that the metal complexing group of the α-diimine metal complex for a dative (complexing) bond with the metal atom to have an active ethylene oligomerization catalyst when the α-diimine metal complex is contacted with ethylene and a cocatalyst. Additionally, the X-ray crystal structure indicates that the α-diimine metal complexes may be isolated in a dimeric form (having bridging halogen atoms) and have an active ethylene oligomerization catalyst when the α-diimine metal complex is contacted with ethylene and a cocatalyst.

Example 8

Synthesis of the α-Diimine Metal Complex Having Structure VI

A solution of 0.235 g (1.02 mmol) of 2-(diphenylphosphino)ethylamine in 40 mL of anhydrous butanol was added via cannula to 0.377 g (1.02 mmol) of α-acylimine compound II and 0.130 g (1.02 mmol) of anhydrous $FeCl_2$. The solution was stirred overnight under argon at 55° C. The resulting dark green solution was reduced in volume to 5 mL in vacuo, depositing a green solid. This solid was filtered, washed with diethyl ether and dried to give 0.352 g (49%) of green product. Recrystallization was done in MeCN.

Example 9

Polymerization procedure: In separate runs, each of the complexes listed in Table 9 (prepared as a standard solution in methylene chloride, or as a homogeneous mixture in biphenyl) was placed in an NMR tube in a substantially oxygen- and moisture-free environment. If the biphenyl mixture was used, about 0.5 ml of methylene chloride was added to the tube. The NMR tube was then sealed and affixed (using copper wire) to the internal stirring mechanism of a 500 ml stainless steel autoclave, such that the beginning of stirring would break the NMR tube and release the contents into the reactor. The reactor was then evacuated and charged with anhydrous solvent that contained the aluminum cocatalyst. The reactor was then pressurized with ethylene, and stirring was commenced to initiate the reaction. Ethylene pressure was held constant and reaction temperature was controlled at the temperature set point by internal cooling coils. Each reaction was commenced at about 30° C.; for selected reactions a maximum exotherm is shown in Table 9. At the end of each reaction, the ethylene was slowly vented, and the products were analyzed by gas chromatography using the solvent as the internal standard. The Schulz-Flory constant K was used to estimate the total amount of product made.

TABLE 9

Ethylene Polymerization Results

| Entry | Catalyst Structure | Amt (mg) | Co-catalyst. | Al:Fe | $P_{ethylene}$ (psig) | Solvent (ml) | Length (min) | T (C.) | $T_{max}$ (C.) | Yield (g) | Productivity (lb/lb cat) | K value ($C_{12}/C_{10}$) | $C_6$ % purity | $C_8$ % purity | $C_{10}$ % purity |
|---|---|---|---|---|---|---|---|---|---|---|---|---|---|---|---|
| 1 | II | 6.0 | MMAO | 500 | 400 | Heptane, 100 | 60 | 55 | 56 | 50 | 8,300 | ~0.5 | 99.1 | 98.8 | 98.6 |
| 2 | VII | 4.0 | MMAO | 500 | 400 | Heptane, 100 | 30 | 30 | | NA | | | | | |
| 3 | VIII | 4.0 | MMAO | 500 | 400 | Heptane, 100 | 30 | 30 | | NA | | | | | |
| 4 | III | 4.0 | MMAO | 500 | 400 | Heptane, 100 | 10 | 55 | 57 | 43 | 11,000 | 0.61 | 99.15 | 98.92 | 98.75 |
| 5 | III | 4.0 | MMAO | 500 | 400 | Heptane, 100 | 30 | 55 | 62 | 69 | 17,000 | 0.60 | 99.17 | 98.92 | 98.85 |
| 6 | III | 1.0 | MMAO | 1000 | 400 | Heptane, 100 | 30 | 40 | 42 | 31 | 31,000 | 0.60 | 99.60 | 99.26 | 99.25 |
| 7 | IX | 4.0 | MMAO | 500 | 400 | Heptane, 100 | 10 | 30 | | NA | | | | | |
| 8 | X | 4.0 | MMAO | 500 | 400 | Heptane, 100 | 30 | 30 | | NA | | | | | |
| 9 | XI | 4.0 | MMAO | 500 | 400 | Heptane, 100 | 30 | 30 | | <5 | | | | | |
| 10 | XII | 4.0 | MMAO | 500 | 400 | Heptane, 100 | 30 | 30 | | NA | | | | | |
| 11 | I | 6.0 | MMAO | 500 | 400 | Heptane, 100 | 30 | 30 | | <5 | | | | | |
| 12 | IV | 4.0 | MMAO | 500 | 400 | Heptane, 100 | 30 | 55 | 61 | 90 | 22,000 | 0.42 | 99.16 | 98.62 | 97.97 |
| 13 | V | 4.0 | MMAO | 500 | 400 | Heptane, 100 | 30 | 50 | 52 | 31 | 7,700 | 0.64 | 98.95 | | 97.43 |
| 14 | VI | 4.0 | MMAO | 500 | 650 | Heptane, 200 | 30 | 45 | 45 | 15 | 7300 | PE | | | |
| 15 | III | 2.0 | MMAO | 500 | 400 | Heptane, 200 | 30 | 55 | 57 | 153 | 76,000 | ~0.6 | | | |
| 16 | III | 1.0 | MMAO | 1000 | 400 | Heptane, 200 | 60 | 50 | 54 | 83 | 83,000 | 0.60 | 99.86 | 99.88 | 99.36 |
| 17 | XIII | 4.0 | MMAO | 500 | 400 | Heptane, 200 | 60 | 40 | 46 | 21 | 5,400 | 0.61 | 98.62 | 98.70 | 97.54 |
| 18 | III | 0.8 | MMAO | 1000 | 800 | Heptane, 200 | 30 | 50 | 71 | 94 | 117,000 | 0.59 | 99.70 | 99.63 | 99.04 |
| 20 | III | 1.0 | MMAO | 1000 | 400 | Heptane, 200 | 60 | 50 | 71 | 85 | 85,000 | 0.61 | 99.82 | 99.81 | 99.39 |
| 21 | III | 0.4 | MMAO | 2000 | 800 | Heptane, 200 | 60 | 40 | 43 | 16 | 40,000 | 0.54 | 99.52 | 99.06 | |
| 22 | XIV | 4.0 | MMAO | 500 | 650 | Heptane, 200 | 60 | 40 | 42 | 30 | 7,400 | 0.49 | 99.20 | 98.54 | 97.67 |
| 23 | XV | 4.0 | MMAO | 500 | 650 | Heptane, 200 | 30 | 35 | 37 | 6.4 | 1,600 | 0.60 | nd | nd | nd |
| 24 | XVI | 4.0 | MMAO | 500 | 400 | Heptane, 100 | 20 | 30 | | NA | | | | | |
| 25 | IV | 2.0 | MMAO | 1000 | 400 | Heptane, 100 | 30 | 50 | 51 | 45 | 22,500 | 0.45 | 97.93 | 97.57 | 97.68 |
| 26 | XVII | 4.0 | MMAO | 500 | 400 | Heptane, 100 | 15 | 30 | | NA | | | | | |
| 27 | XVIII | 4.0 | MMAO | 500 | 400 | Heptane, 100 | 25 | 30 | | NA | | | | | |
| 28 | XIX | 4.0 | MMAO | 500 | 400 | Heptane, 100 | 30 | 30 | | NA | | | | | |
| 29 | XX | 4.0 | MMAO | 500 | 400 | Heptane, 100 | 20 | 30 | | NA | | | | | |
| 30 | XXI | 4.0 | MMAO | 500 | 650 | Heptane, 200 | 30 | 35 | 35 | 4.8 | 1200 | ~0.6 | 87.3 | | |
| 31 | XXII | 8.0 | MMAO | 500 | 650 | Heptane, 400 | 60 | 35 | 37 | NA | | | | | |

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference in the Description of Related Art is not an admission that it is prior art to the present invention, especially any reference that may have a publication date after the priority date of this application. The disclosures of all patents, patent applications, and publications cited herein are hereby incorporated by reference, to the extent that they provide exemplary, procedural or other details supplementary to those set forth herein.

What is claimed is:

1. An $FeCl_2$ α-diimine metal complex characterized as having:

1) an α-diimine group derived from an aromatic α-diacyl compound;

2) a first imine nitrogen group consisting of a $C_6$ to $C_{30}$ aromatic hydrocarbyl group;

3) a second imine nitrogen group comprising a diphenyl phosphinyl or substituted diphenyl phosphinyl metal salt complexing group and a $—(CH_2)_m—$ linking group linking the metal salt complexing group to the second imine nitrogen atom; and having the structure:

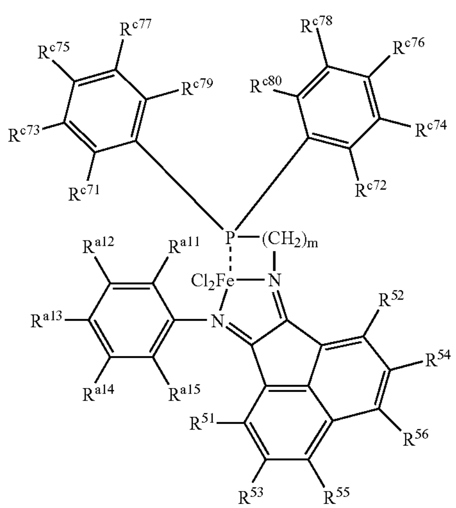

wherein $R^{c71}$ to/through $R^{c80}$ can each independently be hydrogen, an organyl group consisting of inert functional groups, a hydrocarbyl group, or inert functional groups; $R^{51}$ to/through $R^{56}$ can each independently be hydrogen, an organyl group, an organyl group consisting of inert functional groups, or a hydrocarbyl group; $R^{a11}$ to/through $R^{a15}$ can each independently be hydrogen or hydrocarbyl group; and m can be 2 or 3.

2. The α-diimine metal complex of claim 1, wherein the α-diimine group is derived from acenaphthenequinone and $R^{51}$ to $R^{56}$ are each hydrogen.

3. The α-diimine metal complex of claim 1, wherein first imine nitrogen group consisting of a $C_6$ to $C_{30}$ aromatic hydrocarbyl group is a 2,6-disubstituted phenyl group.

4. The α-diimine metal complex of claim 3, wherein the 2,6-disubstituted phenyl group is a 2,6-dimethylphenyl group, a 2,6-diethylphenyl group, or a 2,6-diisopropylphenyl group.

5. The α-diimine metal complex of claim 1, wherein the second imine nitrogen group comprises a diphenyl phosphinyl metal salt complexing group and a $—(CH_2)_2—$ linking group linking the metal salt complexing group to the second imine nitrogen atom.

6. The α-diimine metal complex of claim 1, wherein the first imine nitrogen group consisting of a $C_6$ to $C_{30}$ aromatic hydrocarbyl group is a 2,6-disubstituted phenyl group, and the second imine nitrogen group comprises a diphenyl phosphinyl metal salt complexing group and a $—(CH_2)_2—$ linking group linking the metal salt complexing group to the second imine nitrogen atom.

7. The α-diimine metal complex of claim 6, wherein the 2,6-disubstituted phenyl group is a 2,6-dimethylphenyl group, a 2,6-diethylphenyl group, or a 2,6-diisopropylphenyl group.

8. The α-diimine metal complex of claim 2, wherein the first imine nitrogen group consisting of a $C_6$ to $C_{30}$ aromatic hydrocarbyl group is a 2,6-disubstituted phenyl group, and the second imine nitrogen group comprises a diphenyl phosphinyl metal salt complexing group and a $—(CH_2)_2—$ linking group linking the metal salt complexing group to the second imine nitrogen atom.

9. The α-diimine metal complex of claim 8, wherein the 2,6-disubstituted phenyl group is a 2,6-dimethylphenyl group, a 2,6-diethylphenyl group, or a 2,6-diisopropylphenyl group.

10. The α-diimine metal complex of claim 1 having Structure III:

Structure III

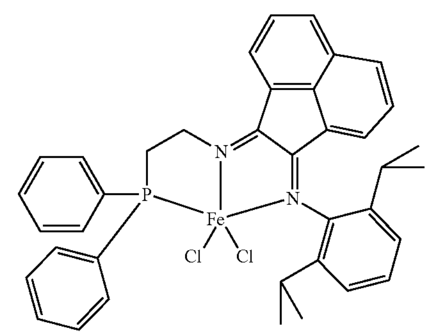

11. The α-diimine metal complex of claim 1 having Structure IV:

Structure IV

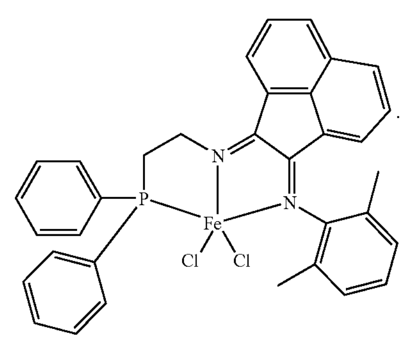

12. The α-diimine metal complex of claim 1 having Structure XIII:
Structure XIII
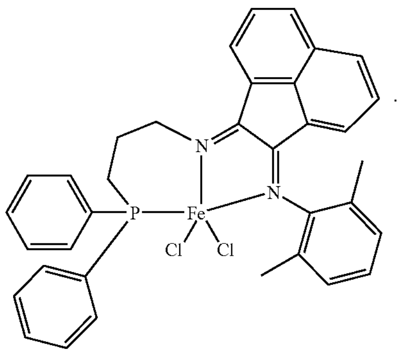
13. The α-diimine metal complex of claim 1 having Structure XIV:
Structure XIV
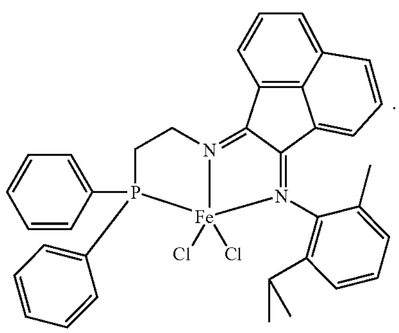
14. The α-diimine metal complex of claim 1 having Structure XV:
Structure XV
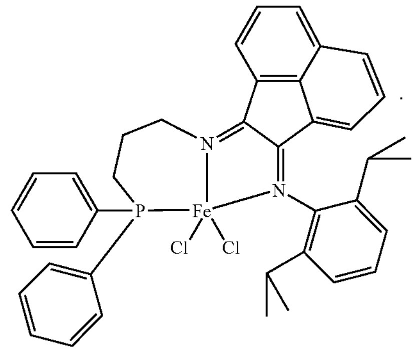
15. The α-diimine metal complex of claim 1 having Structure VI:
Structure VI
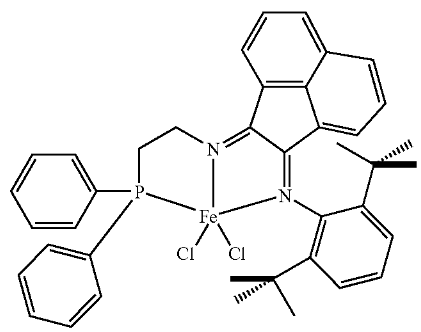
* * * * *

UNITED STATES PATENT AND TRADEMARK OFFICE

CERTIFICATE OF CORRECTION

PATENT NO. : 7,268,096 B2
APPLICATION NO. : 11/186306
DATED : September 11, 2007
INVENTOR(S) : Brooke L. Small et al.

It is certified that error appears in the above-identified patent and that said Letters Patent is hereby corrected as shown below:

Column 16, line 22, replace “2,6-dilsopropylaniline” with --2,6-diisopropylaniline--

Column 16, line 26, replace “2,6-dilsopropylaniline” with --2,6-diisopropylaniline--

Column 37, line 15, replace “α-lacylimine” with --α-acylimine--

Column 44, line 40, replace “having. Structures” with --having Structures--

Column 84, line 37, replace “produces, a” with --produces a--

Column 90, line 62, replace “2,6-diusopropylaniline” with --2,6-diisopropylaniline--

Signed and Sealed this
Second Day of October, 2012

David J. Kappos

David J. Kappos
*Director of the United States Patent and Trademark Office*